United States Patent
Lee et al.

(10) Patent No.: US 9,388,223 B2
(45) Date of Patent: *Jul. 12, 2016

(54) MYOSTATIN INHIBITOR COMPRISING EXTRACELLULAR WATER-SOLUBLE DOMAINS OF DLK1 AS ACTIVE INGREDIENT

(71) Applicant: Antibody and Receptor Therapeutics Co., Ltd., Daejeon (KR)

(72) Inventors: Dong Hee Lee, Gyeonggi-do (KR); Bum Chan Park, Daejeon (KR); Jae Eun Park, Daejeon (KR); Myeong Hee Jang, Daejeon (KR); Seok Ho Yoo, Daejeon (KR); Hye Nan Kim, Daejeon (KR)

(73) Assignee: Antibody and Receptor Therapeutics Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/370,341

(22) PCT Filed: Jan. 3, 2013

(86) PCT No.: PCT/KR2013/000033
§ 371 (c)(1),
(2) Date: Jul. 2, 2014

(87) PCT Pub. No.: WO2013/103248
PCT Pub. Date: Jul. 11, 2013

(65) Prior Publication Data
US 2015/0030595 A1    Jan. 29, 2015

(30) Foreign Application Priority Data
Jan. 5, 2012 (KR) .................. 10-2012-0001460

(51) Int. Cl.
| | |
|---|---|
| A61P 21/00 | (2006.01) |
| A61P 21/06 | (2006.01) |
| A61P 19/08 | (2006.01) |
| A61P 19/10 | (2006.01) |
| A61P 3/04 | (2006.01) |
| A61P 3/10 | (2006.01) |
| A61K 38/17 | (2006.01) |
| C07K 14/47 | (2006.01) |
| A61K 38/16 | (2006.01) |
| C07K 16/18 | (2006.01) |
| C07K 16/28 | (2006.01) |
| C07K 14/475 | (2006.01) |
| C07K 14/71 | (2006.01) |

(52) U.S. Cl.
CPC .............. C07K 14/47 (2013.01); A61K 38/16 (2013.01); A61K 38/17 (2013.01); C07K 14/4703 (2013.01); C07K 14/475 (2013.01); C07K 14/71 (2013.01); C07K 16/18 (2013.01); C07K 16/28 (2013.01); *C07K 2317/52* (2013.01); *C07K 2317/56* (2013.01); *C07K 2317/622* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2013/0202592 A1 *   8/2013   Park et al. .................. 424/134.1

FOREIGN PATENT DOCUMENTS

| KR | 10-0982170 | 9/2010 |
|---|---|---|
| WO | WO 2011115323 A1 * | 9/2011 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
McPherron et al., "Regulation of skeletal muscle mass in mice by a new TGF-β superfamily member," *Nature*, 1997, 387:83-90.
Lee, "Regulation of Muscle Mass by Myostatin," *Annu. Rev. Cell Dev. Biol.*, 2004, 20:61-86.
Lin et al., "Myostatin Knockout in Mice Increases Myogenesis and Decreases Adipogenesis," *Biochemical and Biophysical Research Communications*, 2002, 291:701-706.
Zimmers et al., "Induction of Cachexia in Mice by Systemically Administered Myostatin," *Science*, 2002, 296:1486-1488.
Hadjipavlou et al., "Two single nucleotide polymorphisms in the *myostatin* (GDF8) gene have significant association with muscle depth of commercial Charollais sheep," *Animal Genetics*, 2008, 39:346-353.
McPherron et al., "Double muscling in cattle due to mutations in the myostatin gene," *Proc. Natl. Acad. Sci. USA*, 1997, 94:12457-12461.
Kambadur et al., "Mutations in *myostatin* (GDF8) in Double-Muscled Belgian Blue and Piedmontese Cattle," *Genome Res*, 1997, 7:910-915.

(Continued)

*Primary Examiner* — Zachary Howard
(74) *Attorney, Agent, or Firm* — Riverside Law LLP

(57) ABSTRACT

The present invention relates to a myostatin inhibitor comprising extracellular water-soluble domains of delta-like 1 homolog (DLK1) as active ingredients. More particularly, the present invention relates to a composition for inhibiting myostatin activity, comprising, as active ingredients, extracellular water-soluble domains of DLK1 or a deletion mutant of extracellular water-soluble domains of DLK1. The myostatin inhibitor of the present invention is bonded to the myostatin or activin receptor type IIB so as to inhibit the action mechanism of the myostatin, to thereby promote myogenesis and prevent differentiation into fat cells. Therefore, the myostatin inhibitor of the present invention may be used in preventing and treating diseases such as muscular dysplasia that requires differentiation to muscular cells, or metabolic diseases.

11 Claims, 22 Drawing Sheets

(56) References Cited

OTHER PUBLICATIONS

Lee et al., "Regulation of myostatin activity and muscle growth," *PNAS*, 2001, 98(16):9306-9311.
Rebbapragada et al., "Myostatin Signals through a Transforming Growth Factor β-Like Signaling Pathway to Block Adipogenesis," *Molecular and Cellular Biology*, 2003, 23(20):7230-7242.
Thies et al., "GDF-8 propeptide binds to GDF-8 and antagonizes biological activity by inhibiting GDF-8 receptor binding," *Growth Factors*, 2001, 18(4):251-259 (Abstract only).
Zhu et al., "Myostatin signaling through Smad2, Smad3 and Smad4 is regulated by the inhibitory Smad7 by a negative feedback mechanism," *Cytokine*, 2004, 26:262-272.
Huang et al., "Regulation of myostatin signaling by c-Jun N-terminal kinase in C2C12 cells," *Cellular Signaling*, 2007, 19:2286-2295.
Philip et al., "Regulation of GDF-8 signaling by the p38 MARK," *Cellular Signaling*, 2005,17:365-375.
Steelman et al., "Transcriptional profiling of myostatin-knockout mice implicates Wnt signaling in postnatal skeletal muscle growth and hypertrophy," *The FASEB Journal*, 2006, 20:580-582.
Yang et al., "Extracellular Signal-Regulated Kinase ½ Mitogen-Activated Protein Kinase Pathway is Involved in Myostatin-Regulated Differentiation Repression," *Cancer Res*, 2006, 66:1320-1326.
Allen et al., "Myostatin expression is increased by food deprivation in a muscle-specific manner and contributes to muscle atrophy during prolonged food deprivation in mice," *J Appl Physiol*, 2010, 109:692-701.
Ma et al., "Glucocorticoid-induced skeletal muscle atrophy is associated with upregulation of myostatin gene expression,"*Am J Physiol Endocrinol Metab*, 2003, 285:E363-E371.
Gonzalez-Cadavid et al., "Organization of the human myostatin gene and expression in healthy men and HIV-infected men with muscle wasting," *Proc Natl Acad Sci USA*, 1998, 95:14938-14943.
Reardon et al., "Myostatin, Insulin-Like Growth Factor-1, and Leukemia Inhibitory Factor mRNAs are Upregulated in Chronic Human Disuse Muscle Atrophy," *Muscle Nerve*, 2001, 24:893-899.
Hittel et al., "Increased Secretion and Expression in Myostatin in Skeletal Muscle from Extremely Obese Women," *Diabetes*, 2009, 58:30-38.
Milan et al., "Changes in muscle myostatin expression in obese subjects after weight loss," *The Journal of Clinical Endocrinology& Metabolism*, 2004, 89(6):2724-2727.
Chen et al., "Upregulation of myostatin gene expression in streptozotocin-induced type 1 diabetes mice is attenuated by insulin." *Biochemical and Biophysical Research Communications*, 2009, 388:112-116.
Park et al., "GRB14, GPD1, and GDF9 as potential network collaborators in weight loss-induced improvements in insulin action in human skeletal muscle," *Physiol Genomics*, 2006, 27:114-121.
McPherron et al., "Suppression of body fat accumulation in myostatin-deficient mice," *The Journal of Clinical Investigation*, 2002, 109(5):595-601.
Dilger et al., "Myostatin null mice respond differently to dietary-induced and genetic obesity,"*Animal Science Journal*, 2010, 81:586-593.
Zhao et al., "Transgenic expression of myostatin propeptide prevents diet-induced obesity and insulin resistance," *Biochemical and Biophysical Research Communications*, 2005, 337:248-255.
Guo et al., "Myostatin Inhibition in Muscle, but Not Adipose Tissue, Decreases Fat Mass and Improves Insulin Sensitivity," *PLoS One*, 2009, 4(3):e4937, pp. 1-11.
Wilkes et al., "Loss-of-Function Mutation in Myostatin Reduces Tumor Necrosis Factor α Production and Protects Liver Against Obesity-Induced Insulin Resistance," *Diabetes*, 2009, 58:1133-1143.
Chen et al., "Myostatin regulates glucose metabolism via the AMP-activated protein kinase pathway in skeletal muscle cells," *The International Journal of Biochemistry & Cell Biology*, 2010, 42:2072-2081.

Lee et al., "Regulation of muscle growth by multiple ligands signaling through activin type II receptors," *PNAS*, 2005, 102(50):18117-18122.
Lee et al., "Regulation of Muscle Mass by Follistatin and Activins," *Molecular Endocrinology*, 2010, 24:1998-2008.
Wang et al., "Ectodomain Shedding of Preadipocyte Factor 1 (Pref-1) by Tumor Necrosis Factor Alpha Converting Enzyme (TACE) and Inhibition of Adipocyte Differentiation," *Molecular and Cellular Biology*, 2006, 26(14):5421-5435.
Smas et al., "Pref-1, a protein containing EGF-like repeats, inhibits adipocyte differentiation," *Cell*, 1993, 73(4):725-34, Abstract only.
Smas et al., "Structural characterization and alternate splicing of the gene encoding the preadipocyte EGF-like protein pref-1," *Biochemistry*, 1994, 33(31):9257-65, Abstract only.
Wang et al., "Pref-1, a Preadipocyte Secreted Factor the Inhibits Adipogenesis," *Journal of Nutrition*, 2006, 136:2953-2956.
Jensen et al., "Protein structure of fetal antigen 1 (FA1)—A novel circulating human epidermal-growth-factor-like protein expressed in neuroendocrine tumors and its relation to the gene products of dlk and pG2," *Eur J Biochem*, 1994, 225:83-92.
Kaneta et al., "A Role for Pref-1 and HES-1 in Thymocyte Development," *J lmmunol*, 2000, 164:256-264.
Floridon et al., "Does Fetal antigen 1 (FA1) identify cells with regenerative, endocrine and neuroendocrine potentials? A study of FA1 in embryonic, fetal, and placental tissue and in maternal circulation," *Differentiation*, 2000, 66:49-59.
Carlsson et al., "Growth Hormone and Prolactin Stimulate the Expression of Rate Preadipocyte Factor-1/Δ-Like Protein in Pancreatic Islets: Molecular Cloning and Expression Pattern during Development and Growth of the Endocrine Pancreas," *Endocrinology*, 1997, 138(9):3940-3948.
Halder et al., "Cloning of a Membrane-Spanning Protein with Epidermal Growth Factor-Like Repeat Motifs from Adrenal Glomerulosa Cells," *Endocrinology*, 1998, 139(7):3316-3328.
Schmidt et al., "The *Dlk1* and *Gtl2* genes are linked and reciprocally imprinted," *Genes & Development*, 2000, 14:1997-2002.
Takada et al., "Delta-like and gtl2 are reciprocally expressed, differentially methylated linked imprinted genes on mouse chromosome 12," *Curr Biol*, 2000, 10(18):1135-8, Abstract Only.
Wylie et al., "Novel Imprinted *DLK1/GTL2* Domain on Human Chromosome 14 Contains Motifs that Mimic Those Implicated in *IGF2/H19* Regulation," *Genome Research*, 2000, 10:1711-1718.
Chen et al., "Activin signaling and its role in regulation of cell proliferation, apoptosis, and carcinogenesis," *Exp Biol Med*, 2006, 231(5):534-44, Abstract Only.
Villena et al., "Pref-1 and ADSF/resistin: two secreted factors inhibiting adipose tissue development," *Horm Metab Res.*, 2002, 34(11-12):664-670, Abstract Only.
Sakajiri et al., "Dlk1 in normal and abnormal hematopoiesis," *Leukemia*, 2005, 19:1404-1410.
Li et al., "Expression of DLK1 in hematopoietic cells results in inhibition of differentiation and proliferation," *Oncogene*, 2005, 24:4472-4476.
Bauer et al., "Modulated Expression of the Epidermal Growth Factor-Like Homeotic Protein dlk Influences Stromal-Cell-Pre-B-Cell Interactions, Stromal Cell Adipogenesis, and Pre-B-Cell Interleukin-7 Requirements,"*Molecular and Cellular Biology*, 1998, 18(9):5247-5255.
Samulewicz et al., "Expression of preadipocyte factor-1 (Pref-1), a delta-like protein, in healing mouse ears," *Wound Rep Reg*, 2002, 10:215-221.
Waddell et al., "D1k1 is Necessary for Proper Skeletal Muscle Development and Regeneration," *PLoS One*, 2010, 5(11):e15055, pp. 1-12.
Davis et al., "Ectopic expression of DLK1 protein in skeletal muscle of padumnal heterozygotes causes the callipyge phenotype," *Curr Biol.*, 2004, 14(20):1858-62, Abstract Only.
NCBI GenBank accession No. AAH07741.1.
NCBI GenBank accession No. ABC26875.1.

\* cited by examiner

FIG. 3

Heavy chain

|  | FR1 | CDR1 | FR2 | CDR2 |  |
|---|---|---|---|---|---|
| DLK1 A04 HC | QVQLVESGAEVKKPGASVKVSCKASGYTFK | DYAIH | WVRQAPGQGLEWMG | WINPGSGNTKYSHNFEG | |
| DLK1 A05 HC | CMQLVESGGGLVQPGRSLRLSCAASGFTFD | EHAMH | WVRQAPGKGLEWVS | GINWNSGKIGYADSVKG | |
| DLK1 A10 HC | QVQLVESGGGLVQPGRSLRLSCAASGFTFD | DYAMH | WVRQAPGKGLEWVS | GISWNSGSIGYADSVKG | |
| DLK1 309 HC | CMQLVESGGGRIVRPGGSLRLSCAASGFPFT | SYAMN | WVRQTPGKGLEWVS | TITAISGKTYYADSVKG | |
| DLK1 H06 HC | QVQLVQSGGGLIQPGGSLRLSCAASGFTFS | LYGMS | WVRQAPGKGLEWVS | SIPGSGTRTHYADSVKG | |
| DLK1 H12 HC | QVQLVQSGGGLVKPGGSLRLSCAASEFTFS | DYYMS | WVRQAPGKGLEWLS | YISSGITYYADSVKG | |

|  | FR3 | CDR3 | FR4 |  |  |
|---|---|---|---|---|---|
| DLK1 A04 HC | RVTLTADASANTAYLELPSLRSEDTAVYYCAR | SVSAYG----SNYTDP | WGQGTLVTVSS | A04 HC 89.5(263/294) VH1-3 |  |
| DLK1 A05 HC | RFTISRDNGKNSLYLQMNSLRAEDTAVYYCAK | SGGYGGN---INWYFDL | WGRGTLVTVSS | A05 HC 95.5(277/290) VH3-9 |  |
| DLK1 A10 HC | RFTISRDNAKNSLYLQMNSLRAEDTAVYYCAR | GPGLATG---KGYADY | WGQGTLVTVSS | A10 HC 98.3(287/292) VH3-9 |  |
| DLK1 309 HC | RFTISRDNSRNTLFLQMNSLRAEDTAVYYCVR | GESCSGG---ACSFDFY | WGQGALVTVSS | 309 HC 90.5(266/294) VH3-23 |  |
| DLK1 H06 HC | RFTISRDNSKNTLFLQMNSLRAEDTAVYYCAK | S---------TAYLFDY | WGPGTLVTVSS | H06 HC 91.1(267/293) VH3-23 |  |
| DLK1 H12 HC | RFTISRDNGKKSLYLEMNSLRAEDTAVYYCAR | LQGHCSGGACSNNFDA | WGQGTLVTVSS | H12 HC 94.9(279/294) VH3-11 |  |

Light chain

|  | FR1 | CDR1 | FR2 | CDR2 |
|---|---|---|---|---|
| DLK1 A04 LC | DIQMTQSPSSLSASVGDRVTITC | QASQD---ISNYLN | WYQQKPGKAPKLLIY | STSNLQS |
| DLK1 A05 LC | QFVLTQ-PPSVSGAPGQNVTISC | IGTSSNIGVGYDVH | WYQQVPGTAPKLLIY | GNNNRPS |
| DLK1 A10 LC | DIQMTQSPSSVSASVGDRVTITC | RASQR---ISSNLA | WYQQKPGKAPKLLLH | SASTLHN |
| DLK1 309 LC | QIVLTQ-PASVSGSPGQSVTISC | TGTSSDIGRYNFWS | WYQEHPGKAPKLLIN | DVTKRPS |
| DLK1 H06 LC | DIQMTQSPRTLSLSPGERATLSC | RASQS----ERVHLA | WYQQKPGQAPRLILH | GASSRAT |
| DLK1 H12 LC | DIQMTQSPSSLSASVGDRLTITC | RASQS----IIYLN | WYQCKPGKAPKLLIY | ALSSLQR |

|  | FR3 | CDR3 | FR4 |  |
|---|---|---|---|---|
| DLK1 A04 LC | GVPSRFSGSGSGTDFTLTISSLQPEDFATYYC | QQLNS-YPL | TFGGGKVDIKRGG | A04 LC 93.7(268/286) L8 |
| DLK1 A05 LC | GVPDRFSGSKSGTSASLAITGLQAEDEADYYC | QSIDSRLGV | VFGGGIKLTVLGGG | A05 LC 93.6(276/295) V1-13 |
| DLK1 A10 LC | GVPSRFSGSASGTDFTLTISSLQPEDVAIYYC | QQGHS-FPY | TFGQGTKLEIKRGG | A10 LC 94.4(268/284) L5 |
| DLK1 309 LC | GFSNRFSGSKSGNTASLTITSGLQAEDEADYSC | GSYAGSYTY | VFGTGTKVTVLGGG | 309 LC 92.3(263/285) V1-4 |
| DLK1 H06 LC | GIPDRFSGSGSGTDFTLTISRLEPEDFAVYYC | CHYGS-PLH | SFGPGTKVEIKRGG | H06 LC 94.5(257/272) A27 |
| DLK1 H12 LC | GVPSRFSGSGSGTDFTLTISGLQPEDFATYYC | QQGYG-TPY | TFGQGTKVDIKRGG | H12 LC 95.8(272/284) O12 |

FIG. 8

| | | FR1 | CDR1 | FR2 | CDR2 | |
|---|---|---|---|---|---|---|
| ACVR2B A06 HC | VQLVQSGGGLVQPGRS-LRLSCTASGFTFG | DYAMS | WVRQAPGKGLEWVG | ------EIRSKRYDGTAEYAASVKG | |
| ACVR2B A07 HC | QLVESGGGLVRPGRS-LTLSCTASGFTFN | DYAMH | WVRQAPGKGLEWVS | ------GISWN--TNSKAYADSVKG | |
| ACVR2B A09 HC | VQLVESGGGLVQPGRS-LRLSCAASGFTFD | SYWMS | WVRAPGKGLEWVA | ------NIKTDGS--EKHYMDSVKG | |
| ACVR2B B11 HC | VQLVESGGGLVQPGRS-LRLSCAASGFTFD | NHAMH | WVRAPGKGLEWVS | ------GISWN--GGTTAYADSVKG | |
| ACVR2B B12 HC | VQLVQSGAEVKKPGES-LKISCKTSGYTFT | HYWIG | WVRQMPGKGLEWMG | ------RINPT--DSYADYSPSFQG | |
| ACVR2B B08 HC | VQLVQSGGGLVHPGQS-LRLSCTGSGFPFG | DYSMT | WVRQAPGKGLEWVG | ------LVRSKAYGGTTEYAASVKG | |
| ACVR2B C07 HC | QMQLVQSGGGLVKPGGS-LRLSCAPSGFTER | DYHMS | WIRQAPGKGLEWIS | ------NISNS--GTNIYYADSVKG | |
| ACVR2B C08 HC | VQLVESGGGLVQPGGS-LRLSCSASGFTFS | SYAMH | WVRQAPGKGLEYVS | ------AISSN--GGSTYYADSVKG | |
| ACVR2B D11 HC | MQLVQSGGGLVQPGRS-LGLSCTASGFTFG | DYAMS | WVRQAPGKGLEWVG | ------EIRSKAYGGTTEYAASVKG | |
| ACVR2B D07 HC | QVQLVQSGAEVKKPGAS-VKVSCKASGYTFT | SYYMH | WVRQAPGQGLEWMG | ------IINPS--GGSTSYAQKFQG | |
| ACVR2B F08 HC | VQLVESGGGLVQPGGS-LRLSCAASGFTFS | DHYMD | WVRQAPGKGLEWVG | ------RTRNKANSYTTEYAASVKG | |

| | | FR3 | CDR3 | FR4 | | |
|---|---|---|---|---|---|---|
| ACVR2B A06 HC | RFTISRDDSKNSLYLQMNSLRAEDTAVYYCAR | G-----HYAMDV | WGQGTTVTVSS | A06 HC | 92.3 (277/300) | VH3-49 |
| ACVR2B A07 HC | RFIISRDNAKNSLYLEMNSLRAEDTAVYYCVR | DGG-RFYYGLDV | WGQGTSVTVSS | A07 HC | 93.2 (272/292) | VH3-9 |
| ACVR2B A09 HC | RFTISRDNAKNSVYLQMNSLRAEDTAVYYCAK | G-----AWLDY | WGQGTQVTVSS | A09 HC | 94.2 (277/294) | VH3-7 |
| ACVR2B B11 HC | RFSIFRDNAEKSLYLQMNSLRAEDTAVYYCAR | GSS-SGRYYFDY | WGQGTLVTVSS | B11 HC | 92.8 (271/292) | VH3-9 |
| ACVR2B B12 HC | HVIMSVDKSVSTAYLHWNSLKASDTAMYYCAR | G-----TALGV | WGQGTTVTVSS | B12 HC | 89.1 (261/293) | VH5-51 |
| ACVR2B B08 HC | RFIMSRDDSRSIAYLQMNSLRAEDTAVYYCAR | G-----HYGMDV | WGQGTTVTVSS | B08 HC | 91.7 (275/300) | VH3-49 |
| ACVR2B C07 HC | RFTISRDNAKNSLYLQMNSLRAEDTAVYYCAR | G-----HYGMDI | WGQGTLITVSS | C07 HC | 94.9 (280/295) | VH3-11 |
| ACVR2B C08 HC | RFTISRDNSKNTLYLQMNSLRAEDTAVYYCAK | TYG-GYGNAFDI | WGQGTMITVSS | C08 HC | 96.2 (280/291) | VH3-64 |
| ACVR2B D11 HC | RLTISRDDSKSIAYLQMNSLRAEDTAVYYCAR | G-----HYGMDV | WGQGTLVTVSS | D11 HC | 96.3 (289/300) | VH3-49 |
| ACVR2B D07 HC | RVTMTRDTSTSTVYMELSSLRSEDTAVYYCAK | DQSRGWYSNFDS | WGQGTLVTVSS | D07 HC | 99.7 (295/296) | VH1-46 |
| ACVR2B F08 HC | RFTISRDDSKNSLYLQMNSLRAEDTAVYYCTK | G-----AWLDY | WGQGTLVTVSS | F08 HC | 98.0 (294/300) | VH3-72 |

FIG. 9

|  | FR1 | CDR1 | FR2 | CDR2 |
|---|---|---|---|---|
| ACVR2B A06 LC | DIQMTQSPSSLSASVGDRVTITC | RASRSISN-------YLN | WQQKPGKAPKLLIY | AASSLQS |
| ACVR2B A07 LC | DIVMTQTPSSPVTLGQPASISC | RSSQSLIHS---DGNTYLS | WQQRPGQPPRLLIY | KISNRFS |
| ACVR2B A09 LC | IQMTQSPSAMSASVGDRVTITC | RASQGISN-------YLA | WFQQKPGKVPKRLIY | AASSLQS |
| ACVR2B B11 LC | DIQMTQSPSSVSASVGDRVTITC | RASQGIST-------YLN | WYQHQSGKAPKLLIY | GAFRLQS |
| ACVR2B B12 LC | IQMTQSPSAMSASVGDRVTITC | RASQGISN-------YLA | WFQQKPGKVPKRLIY | AASSLQS |
| ACVR2B B08 LC | DIQMTQSPSSVSASVGDRVTITC | RASQGISN-------WLA | WYQQKPGKAPKLLIY | AASSLQS |
| ACVR2B C07 LC | DIQMTQSPSSLSASVGDRVTITC | RASQGIAN-------YLA | WYQQKPGKAPKLLIY | AASTLQS |
| ACVR2B C08 LC | DIQMTQSPSSVSASVGDRVTITC | RASQGISR-------WLA | WYQQKPGKAPKLLIY | AASNLQS |
| ACVR2B D11 LC | DIQMTQSPSSLSASVGDRVTITC | RASQNISN-------FLN | WYQQKPGKAPKLLIY | SASRLQR |
| ACVR2B D07 LC | DIQMTQSPSTLSASVGDRVTITC | RASQTVSN-------WLA | WYQLKPGKAPKLLIY | KASSLES |
| ACVR2B F08 LC | IQMTQSPSAMSASVGDRVTITC | RASQGISN-------YLA | WFQQKPGKVPKRLIY | GASSLQS |

|  | FR3 | CDR3 | FR4 |  |  |  |
|---|---|---|---|---|---|---|
| ACVR2B A06 LC | GVPSRFSGSGSGGTDFTLTISSLQPEDFATYYC | QQSYDTPF | TFGLGNQLEIK | A06 LC | 98.2 (279/284) | 012 |
| ACVR2B A07 LC | GVPDRFSGSGAGTDFTLKISRVEAEDVGVYYC | AETSQVPH | TFGQGTKVEIK | A07 LC | 95.0 (287/302) | A23 |
| ACVR2B A09 LC | GVPSRFSGSGSGGTDFTLTISSLQPEDFATYYC | LQHKSYPY | TFGQGTKLEIK | A09 LC | 96.5 (274/284) | L14 |
| ACVR2B B11 LC | GVPSRFSGSGSGTEFTLTISNLQPEDFATYYC | QQANNFPL | TFGQGTKVDIK | B11 LC | 89.5 (256/286) | L19 |
| ACVR2B B12 LC | GVPSRFSGSGSGGTDFTLTISSLQPEDFATYYC | LQHKSYPY | TFGQGTKLEIK | B12 LC | 96.8 (275/284) | L14 |
| ACVR2B B08 LC | GVPSRFSGSGSGGTDFTLTISSLQPEDFATYYC | QQAKSYPY | TFGQGTKVEIK | B08 LC | 98.2 (279/284) | L5 |
| ACVR2B C07 LC | GVPSRFSGSGSGGTDFTLTISSLQPEDFATYYC | QQVKSYPL | SFGQGTKVEIK | C07 LC | 95.5 (273/286) | L8 |
| ACVR2B C08 LC | GVPSRFSGSGSGGTDFTLTINSLQPEDFATYFC | QLGKSFPY | TFGPGTKVEIK | C08 LC | 97.2 (276/284) | L5 |
| ACVR2B D11 LC | GVPSRFSGSGSGGTDFTLTISSLQPEDFATYYC | QQSYSTPY | TFGQGTKLEIK | D11 LC | 96.5 (274/284) | O12 |
| ACVR2B D07 LC | GVPSRFSGTGSETEFTLTISSLQPDDFATYYC | QQTHSYPI | TFGQGTRLEIK | D07 LC | 94.3 (266/282) | L12a |
| ACVR2B F08 LC | GVPSRFSGSGSGGTEFTLTITSLQPEDFATYFC | LQHKSYPL | TFGPGTKVEIK | F08 LC | 95.8 (273/285) | L14 |

FIG. 14

|    |                           | A             | B             |
|----|---------------------------|---------------|---------------|
|    |                           | ACVR2B-Fc     | DLK1-Fc       |
|    |                           | Y             | Y             |
| 1  | One site binding (hyperbola) |            |               |
| 2  | Best-fit values           |               |               |
| 3  | BMAX                      | 5.582         | 2.506         |
| 4  | KD                        | 256.2         | 22.77         |
| 5  | Std. Error                |               |               |
| 6  | BMAX                      | 0.8019        | 0.1520        |
| 7  | KD                        | 47.89         | 3.665         |
| 8  | 95% Confidence Intervals  |               |               |
| 9  | BMAX                      | 3.945 to 7.220 | 2.196 to 2.817 |
| 10 | KD                        | 158.4 to 354.0 | 15.29 to 30.25 |
| 11 | Goodness of Fit           |               |               |
| 12 | Degrees of Freedom        | 30            | 30            |
| 13 | R²                        | 0.9908        | 0.9344        |
| 14 | Absolute Sum of Squares   | 0.07600       | 0.9351        |
| 15 | Sy.x                      | 0.05033       | 0.1766        |
| 16 | Constraints               |               |               |
| 17 | BMAX                      | BMAX > 0.0    | BMAX > 0.0    |
| 18 | KD                        | KD > 0.0      | KD > 0.0      |
| 19 | Data                      |               |               |
| 20 | Number of X values        | 8             | 8             |
| 21 | Number of Y replicates    | 1             | 1             |
| 22 | Total number of values    | 8             | 8             |
| 23 | Number of missing values  | 0             | 0             | ed
MYOSTATIN INHIBITOR COMPRISING EXTRACELLULAR WATER-SOLUBLE DOMAINS OF DLK1 AS ACTIVE INGREDIENT

CROSS-REFERENCE TO RELATED APPLICATIONS

This application is the U.S. national phase application filed under 35 U.S.C. §371claiming benefit to International Patent Application No. PCT/KR2013/000033, filed on Jan. 3, 2013, which is entitled to priority under 35 U.S.C. §119(a)-(d) to Korea application no. 10-2012-0001460, filed on Jan. 5, 2012 the disclosure of which is incorporated herein by reference in its entirety.

TECHNICAL FIELD

The present invention relates to a myostatin inhibitor including an extracellular water-soluble domain of a delta-like 1 homolog (DLK1) as an active ingredient, and, more particularly, to a composition for inhibiting myostatin activities including an extracellular water-soluble domain of DLK1 or a deletion mutant of the extracellular water-soluble domain of DLK1 as an active ingredient, and a pharmaceutical composition for preventing or treating a myostatin-related disease.

BACKGROUND ART

Myostatin is a transforming growth factor-β (TGF-β) superfamily member that serves as a very potent autocrine/paracrine inhibitor of muscle growth (A. C. McPherron, A. M. Lawler, S. J. Lee, *Nature.* 387, 83-90, 1997). Myostatin is composed of 376 amino acids, and its precursor protein is activated by 2 cleavages using proteinases. A first cleavage step is to remove a 24-amino acid signal peptide using a purine family of enzymes and a second cleavage step is performed by cleavage by BMP1/Tolloid matrix metalloproteinases. In this case, the cleavage occurs at an Arg-Ser-Arg-Arg (RSRR) site at $240^{th}$ to $243^{rd}$ amino acids to generate an N-terminal myostatin propeptide (27.64 kDa) and a C-terminal fragment (12.4 kDa) (S. J. Lee, *Annu. Rev. Cell. Dev. Biol.* 20, 61-86, 2004). It was known that active types of mature myostatin form dimers through disulfide bonds at the C-terminal region, and shows a 100% homology with those from a mouse, a rat, a pig, a chicken, a turkey, a dog, and the like.

When myostatin is not expressed in mouse cell, a rapid increase in mass of skeletal muscles results in muscle hypertrophy and hyperplasia (A. C. McPherson et al., *Nature.* 387, 83-90, 1997; J. Lin et al., *Biochem. Biophys. Res. Commun.* 291, 701-706, 2002; T. A. Zimmers et al. *Science.* 296, 1486-1488, 2002). In addition to the mice, it was reported that mutations of myostatin in some cattle and sheep results in muscle hypertrophy (G. Hadjipavlou, et. al., *Anim. Genet.* 39, 346-353, 2008; A. C. McPherson and S. J. Lee, *Proc. Natl. Acad. Sci.* 94, 12457-12461, 1997; R. Kambadur et al., *Genome Res.* 7, 910-916, 1997). In recent years, it was reported that myostatin acts by directly binding to activin receptor type IIB (AVR2B) (S. J. Lee, and A. C. McPherron, *Proc. Natl. Acad. Sci. U.S.A.* 98, 9306-9311, 2001; A. Rebbapragada et al., *Mol. Cell. Biol.* 23, 7230-7242, 2003; R. S. Thies et al., *Growth Factors.* 18, 251-259, 2001), and has signaling mechanisms through Smads signaling pathways (S. J. Lee, and A. C. McPherson, *Proc. Natl. Acad. Sci. U.S.A.* 98, 9306-9311, 2001; A. Rebbapragada et al., *Mol. Cell. Biol.* 23, 7230-7242, 2003; X. Zhu et al., *Cytokine.* 26, 262-272, 2004).

It was also reported that myostatin affects a p38 MAPK signaling pathway, an Ras-ERK1/2 pathway and a JNK signaling pathway in addition to the Smads signaling pathway (Z. Q. Huang et al., *Cell. Signal.* 19, 2286-2295, 2007; B. Philip et al., *Cell. Signal.* 17, 365-375, 2005; C. A. Steelman et al., *FASEBJ.* 20, 580-582, 2006; W. Yang et al., *Cancer Res.* 66, 1320-1326, 2006). Further, it was reported that myostatin is expressed at an increased level in muscular dysplasia caused by glucocorticoids (D. L. Allen et al. *J. Appl. Physiol.* 109, 692-701, 2010; K. Ma et al., *Am. J. Physiol.* 285, E363-E371, 2003), skeletal muscle degeneration-related diseases caused by HIV infections (N. F. Gonzalez-Cadavid et al., *Proc. Natl. Acad. Sci. U.S.A.* 95, 14938-14943, 1998), and chronic illnesses (K. A. Reardon et al., *Muscle Nerve.* 24, 893-899, 2001). It was known that an increased expression of myostatin is associated with metabolic disorder such as obesity, diabetes, and the like (D. S. Hittel et al., *Diabetes.* 58, 30-38, 2009; G. Milan et al., *J. Clin. Endocrinol. Metab.* 89, 2724-2727, 2004; Y. W. Chen et al., *Biochem. Biophys. Res. Commun.* 388, 112-116, 2009). The obesity is associated with the metabolic imbalance causing an increase in mass of adipose tissues and enhancing the resistance to insulin. It was reported that mRNA and protein of myostatin are expressed at increased levels in the human muscles with obesity and insulin resistance (D. S. Hittel et al., *Diabetes.* 58, 30-38, 2009; G. Milan et al., *J. Clin. Endocrinol. Metab.* 89, 2724-2727, 2004; J. J. Park et al., *Physiol. Genomics.* 27, 114-121, 2006). It was reported that myostatin-null mice in which myostatin is not expressed show a decrease in body fat mass and high-fat-induced insulin resistance (A. C. McPherron, and S. J. Lee, *J. Clin. Invest.* 109, 595-601. 40, 2002). Also, it was known that a mass of body fats is less increased by the high fat diet in the myostatin-null mice, compared to the wild-type mice (A. C. Dilger et al., *Anim. Sci. J.* 81, 586-593, 2010), and that overexpression of an inhibitory propeptide domain of myostatin suppresses obesity and insulin resistance induced by the high fat diet (B. Zhao et al., *Biochem. Biophys. Res. Commun.* 337, 248-255, 2005). Also, the current in vivo studies showed that the loss of myostatin functions increases the insulin sensitivity, resulting in increased glucose utilization (T. Guo et al., *PloS. ONE.* 4, e4937, 2009; J. J. Wilkes et al., *Diabetes.* 58, 1133-1143, 2009). And it was found that myostatin serves to promote consumption of glucose in muscular cells and regulate the glucose metabolism through an AMPK signaling pathway promoting the intake of glucose (Y. W. Chen et al., *Int. J. Biochem. Cell. Biol.* 42, 2072-2081, 2010).

That is, it was assumed that, when the myostatin mechanism is blocked, myostatin plays important roles in promoting the differentiation of muscles, preventing the obesity by blocking the differentiation into fat cells, and improving metabolic disorders such as diabetes. Therefore, the studies of myostatin inhibitors have been of importance. Up to now, a water-soluble ACVR2B-Fc fusion protein in which a myostatin receptor, ACVR2B, is fused to Fc was reported. And, it was reported that the ACVR2B-Fc fusion protein interferes with the activity of myostatin to inhibit formation of muscles by ACVR2B-Fc (Lee et al., *Proc. Natl. Acad. Sci. U.S.A.* 102, 1817-18122, 2005). As another attempt, there is a case showing an inhibitory effect of myostatin using follistatin which is known to bind to myostatin (Lee et al. *Mol. Endocrinol.* 24(10), 1 998-2008, 2010).

Meanwhile, DLK1 belonging to the notch/delta/serrate family is a transmembrane glucoprotein which is encoded by a dlk1 gene located on the chromosome 14q32, and is composed of 383 amino acids. The glucoprotein is divided into a 280-amino acid extracellular region, two 24-amino acid transmembrane regions, and a 56-amino acid intracellular region. In this case, the glucoprotein has 6 epidermal growth factor-like repeat domains, 3 N-glycosylation sites and 7 O-glycosylation sites, all of which are positioned out of the cell membrane. DLK1 is well known as a membrane protein, and also as a protein shed from the outside of the cell membrane by a tumor necrosis factor-alpha converting enzyme (TACE) to have separate functions (Yuhui Wang and Hei Sook Sul, *Molecular and cellular biology.* 26(14): 5421-5435, 2006).

DLK1 is found in various forms of 50 to 60 kDa by the glycosylations on the cellmembrane (Smas C M and Sul H S, *Cell.* 73: 725-34, 1993), and has 4 splicing variants formed by the alternative splicing (Smas C M et al., *Biochemistry.* 33: 9257-65, 1994). Among these, two larger variants have cleavage sites of proteolytic enzymes, and thus is cleaved by a proteolytic enzyme. TACE, to generate two water-soluble forms of 50 kDa and 25 kDa (Yuhui Wang et al., *Journal of Nutrition.* 136: 2953-2956, 2006).

DLK1 is also widely known as fetal antigen 1 (FA1) (Jensen C H et al., *European Journal of Biochemistry.* 225: 83-92, 1994) since DLK1 is expressed mainly in the embryonic tissues (Smas C M et al., *Cell.* 73: 725-34, 1993; Kaneta M et al., *Journal of Immunology.* 164: 256-64, 2000) and the placenta at a developmental stage, and particularly found in maternal serum at a high concentration. It was reported that DLK1 was also expressed in glandular cells of the pancreas (Kaneta M et al., *Journal of Immunology.* 164: 256-64, 2000), ovary cells, or skeletal myotubes (Floridon C et al., *Differentiation.* 66: 49-59, 2000). DLK1 is not expressed in most tissues after the child birth, but expressed only in certain cells such as preadipocytes (Smas C M et al., *Cell.* 73: 725-34, 1993), pancreatic islet cells (Carlsson C et al., *Endocrinology.* 138: 3940-8, 1997) thymic stromal cells (Kaneta M et al., *Journal of Immunology.* 164: 256-64, 2000), adrenal gland cells (Halder S K et al., *Endocrinology.* 139: 3316-28, 1998), and the like. Further, it was reported that DLK1 is expressed on paternal manoalleles due to the influence of methylation (Schmidt J V et al., *Genes and Development.* 14: 1997-2002, 2000; Takada S et al., *Current Biology* 10: 1135-8, 2000; Wylie A A et al, *Genome Research.* 10: 1711-8, 2000).

Meanwhile, the activin receptor type IIB (ACVR2B) is a protein that is encoded by an ACVR2B gene and is associated with the activin signaling mechanism. It is known that signal transduction by activin is involved in the generation or secretion of follicle-stimulating hormones (FSHs), and the regulation of menstruation cycles, and affects the cell proliferation and differentiation, and the apoptosis (Chen et al., *Exp. Biol. And Med.* 231(5): 534-544, 2006).

DLK1 is widely known as preadipocyte factor-1 (Pref-1) that plays a role of inhibiting differentiation of adipocytes, and its functions are the most widely studied (Smas C M et al., *Cell.* 73: 725-34; Villena J A et al., *Hormone and Metabolic Research.* 34: 664-70, 2002). Beside the ability to inhibit the differentiation of adipocytes, DLK1 is also known as it serves to inhibit the differentiation of hematopoietic stem cells (Sakajiri S et al., *Leukemia.* 19: 1404-10, 2005; Li L et al., *Oncogene.* 24: 4472-6, 2005) and regulate the differentiation of lymphoid progenitor cells (Bauer S R et al., *Molecular and Cellular Biology.* 18: 5247-55, 1998; Kaneta M et al., *Journal of Immunology.* 164: 256-64, 2000) and is involved in the wound healing (Samulewicz S J et al., *Wound Repair and Regeneration.* 10: 215-21, 2002). Further, it was reported that DLK1 is required for the development and regeneration of skeletal muscles (Jolena N. et al., *PLoS One* 5(11), e15055, 2010) and the overexpression of DLK1 causes a callipyge phenotype to generate larges muscles (Erica Davis et al., *Current Biology,* 14, 1858-1862, 2004).

As known so far, it can be seen that DLK1 serves to increase the muscle mass and inhibit the differentiation of adipocytes. Therefore, DLK1 has advantages over the conventional myostatin inhibitors in that it plays two important roles in inhibiting the generation of adipocytes and promoting the generation of muscular cells.

Accordingly, the present inventors have conducted ardent research to elucidate an action mechanism of an extracellular water-soluble domain of DLK1 to promote differentiation of muscular cells and inhibit differentiation of adipocytes, and found that the extracellular water-soluble domain of DLK1 binds to activin receptor type IIB(ACVR2B) serving as myostatin receptor to block binding of ACVR2B to myostatin so that it can inhibit an inhibitory effect of myostatin on muscle differentiation (i.e., myogenesis), and also directly binds to myostatin so that it can affect an inhibitory mechanism of myostatin. Therefore, the present invention has been completed based on these facts.

DISCLOSURE

Technical Problem

The present invention is designed to solve the problems of the prior art, and therefore it is an object of the present invention to provide a novel myostatin inhibitor and a pharmaceutical composition for preventing and treating a disease associated with myostatin using the fact that DLK1 binds to activin receptor type IIB (ACVR2B) and myostatin to promote differentiation of muscular cells.

Technical Solution

To solve the above problem of the prior art, according to an aspect of the present invention, there is provided a composition for inhibiting myostatin activities, which includes an extracellular water-soluble domain of a delta-like 1 homolog (DLK1), a fragment of the extracellular water-soluble domain of DLK1, a mutant of the extracellular water-soluble domain of DLK1, or a fragment of the mutant as an active ingredient.

According to another aspect of the present invention, there is provided a composition for inhibiting myostatin activities, which includes a DLK1-Fc fusion protein, in which an extracellular water-soluble domain of DLK1 or a fragment thereof is conjugated to a human antibody Fc region, as an active ingredient.

According to still another aspect of the present invention, there is provided a pharmaceutical composition for preventing or treating a myostatin-related disease, which includes an extracellular water-soluble domain of DLK1, a fragment of the extracellular water-soluble domain of DLK1, a mutant of the extracellular water-soluble domain of DLK1, or a fragment of the mutant as an active ingredient.

According to still another aspect of the present invention, there is provided a pharmaceutical composition for preventing or treating a myostatin-related disease, which includes a DLK1-Fc fusion protein, in which an extracellular water-soluble domain of DLK1 or a fragment thereof is conjugated to a human antibody Fc region, as an active ingredient.

According to yet another aspect of the present invention, there is provided a kit for diagnosing a myostatin-related disease, which includes an antibody or an aptamer specifically binding to DLK1-myostatin, DLK1-ACVR2B, or a soluble fragment thereof.

Advantageous Effects

The myostatin inhibitor according to one exemplary embodiment of the present invention binds to myostatin or activin receptor type IIB to inhibit an action mechanism of myostatin, and thus can play important roles in promoting myogenesis and preventing differentiation into fat cells, thereby preventing obesity, and also in improving metabolic disorders such as diabetes. Therefore, the myostatin inhibitor according to one exemplary embodiment of the present invention can be useful in preventing and treating diseases such as muscular dysplasia that requires differentiation into muscular cells, or metabolic diseases.

DESCRIPTION OF DRAWINGS

FIG. 3 shows the results obtained by analyzing the following polypeptides in complementarity determining regions (CDRs) of monoclonal phage antibodies against water-soluble DLK1: DLK1 A04 HC (SEQ ID NO: 35), DLK1 A05 HC (SEQ ID NO: 36), DLK1A10 HC (SEQ ID NO: 37), DLK1 B09 HC (SEQ ID NO: 38), DLK1 H06 HC (SEQ ID NO: 39), DLK1 H12 HC (SEQ ID NO: 40), DLK1 A04 LC (SEQ ID NO: 41), DLK1 A 05 LC (SEQ ID NO: 42), DLK1 A10 LC (SEQ ID NO: 43), DLK1 B09 LC (SEQ ID NO: 44), DLK1 H06 LC (SEQ ID NO: 45), and DLK1 H12 LC (SEQ ID NO: 46).

FIG. 8 shows the results obtained by analyzing the following polypeptides in CDRs of heavy chains of monoclonal phage antibodies against water-soluble ACVR2B A06 HC (SEQ ID NO: 47), ACVR2B A07 HC (SEQ ID NO: 48), ACVR2B A09 HC (SEQ ID NO: 49), ACVR2B B11 HC (SEQ ID NO: 50), ACVR2B B12 HC (SEQ ID NO: 51), HC (SEQ ID NO: 54), ACVR2B D11 HC (SEQ ID NO: 55), ACVR2D07 HC (SEQ ID NO: 56), and ACVR2B F08 HC (SEQ ID NO: 57).

FIG. 9 shows the results obtained by analyzing the following polypeptides in CDRs of light chains of the monoclonal phage antibodies against the water-soluble ACVR2B: ACVR2B A06 LC (SEQ ID NO: 58), ACVR2B A07 LC (SEQ ID NO: 59), AVCR2B A09LC (SEQ ID NO: 60), ACVR2B B11 LC (SEQ ID NO: 61), ACVR2B B12 LC (SEQ ID NO: 62), ACVR2B B08 LC (SEQ ID NO: 63), ACVR2B C07 LC (SEQ ID NO: 64), AVR2B C08 LC (SEQ ID NO: 65), ACVR2B D11 LC (SEQ ID NO: 66), ACVR2B D07 LC (SEQ ID NO: 67), and ACVR2B F08 LC (SEQ ID NO: 68).

FIG. 14 shows the results obtained by determining Kd values of myostatin for ACVR2B and DLK1.

BEST MODE

Figure 1:
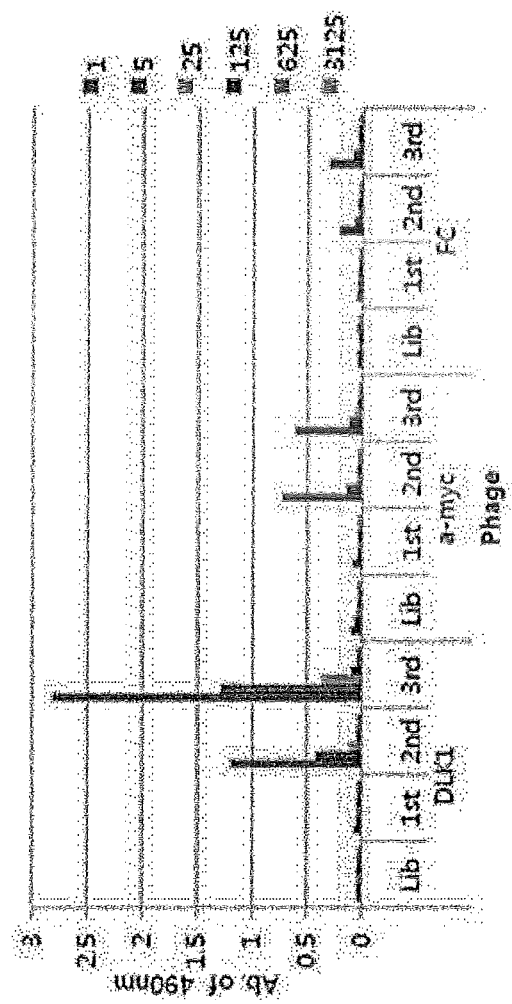
FIG. 1 shows the enzyme-linked immunosorbent assay (ELISA) results of a polyclonal phage antibody against water-soluble DLK1.

To solve the above problem of the prior art, the present invention provides a composition for inhibiting myostatin activities, which includes an extracellular water-soluble domain of a delta-like 1 homolog (DLK1), a fragment of the extracellular water-soluble domain of DLK1, a mutant of the extracellular water-soluble domain of DLK1 or a fragment of the mutant as an active ingredient.

Also, the present invention provides a composition for inhibiting myostatin activities, which includes a DLK1-Fc fusion protein, in which the extracellular water-soluble domain of DLK1 or a fragment thereof is conjugated to a human antibody Fc region, as an active ingredient.

In the present invention, the term "delta-like 1 homolog" or "DLK" refers to a transmembrane glucoprotein which is encoded by a dlk1 gene located on the chromosome 14q32 and is composed of 383 amino acids.

In the present invention, the term "extracellular water-soluble domain of DLK" refers to a water-soluble domain of an extracellular region in a DLK1 protein which is divided into an extracellular region, transmembrane regions, and an intracellular region. An anti-cancer effect of the extracellular water-soluble domain of DLK1 was first elucidated by the present inventors, and effects of the extracellular water-soluble domain of DLK1 on differentiation of muscular cells and fat cells were found in the present invention.

In this specification, the extracellular water-soluble domain of DLK1 and the water-soluble DLK1 may be used interchangeably.

Preferably, the water-soluble DLK1 according to one exemplary embodiment of the present invention may be composed of 200 to 300 amino acids to have water-soluble DLK1 activities, and more preferably may have an amino acid sequence set forth in SEQ ID NO: 29. In this case, amino acid sequences having the water-soluble DLK1 activities may be used without limitation.

In the present invention, the mutant of the extracellular water-soluble domain of DLK1 is characterized in that it is a deletion mutant of the extracellular water-soluble domain of DLK1.

In the present invention, the term "deletion mutant of an extracellular water-soluble domain of DLK" refers to a deletion mutant having an epidermal growth factor-like repeat (EGF-like repeat) or a juxtamembrane sequence, and, more particularly, a deletion mutant obtained by sequentially deleting EGF-like repeat domains of the water-soluble DLK1.

Preferably, the deletion mutant of the extracellular water-soluble domain of DLK1 according to one exemplary embodiment of the present invention may be one selected from the group consisting of $EGF_{3-6}$ in which $1^{st}$ and $2^{nd}$ domains are deleted among 6 EGF-like repeat domains, $EGF_{4-6}$ in which $1^{st}$ to $3^{rd}$ domains are deleted, $EGF_{5-6}$ in which $1^{st}$ to $4^{th}$ domains are deleted, $EGF_6$ in which $1^{st}$ to $5^{th}$ domains are deleted, and a juxtamembrane region (JM) in which the six domains are all deleted. More preferably, the deletion mutant of the extracellular water-soluble domain of DLK1 may have one of amino acid sequences set forth in SEQ ID NOS: 30 to 34, but the present invention is not limited thereto.

In the present invention, the extracellular water-soluble domain of DLK1, the fragment of the extracellular water-soluble domain of DLK1, the mutant of the extracellular water-soluble domain of DLK1, or the fragment of the mutant binds to myostatin or activin receptor type IIB (ACVR2B) to inhibit an action of myostatin, and thus plays parts in the promotion of differentiation of muscular cells and/or the inhibition of differentiation of fat cells.

More particularly, the EGF-like repeat 5 or 6 or the juxtamembrane sequence plays an important role in the relationship between DLK1 and ACVR2B, and the juxtamembrane sequence plays an important role in the relationship between DLK1 and myostatin. These relationships were found in Examples of the present invention.

In the present invention, the term "activin" refers to a type of a peptidic hormone having a molecular weight of approximately 25,000, which includes 3 types of activin A that is a homodimer (βAβA) of β chains of inhibin A, activin B that is a homodimer (βBβB) of β chains of inhibin B, and activin AB that is a heterodimer (βAβB) thereof. Preferably, the activin may be activin A.

In the present invention, the term "activin receptor type IIB" or "ACVR2B" refers to a protein which is encoded by an ACVR2B gene and is known as a representative myostatin receptor. Signal transduction by the binding of myostatin to activin receptor type IIB promotes inhibition of myostatin to inhibit the differentiation of muscular cells and causes the differentiation of fat cells, and thus is known to be involved in various muscle-related diseases and metabolic diseases.

According to another aspect of the present invention, the present invention provides a pharmaceutical composition for preventing or treating a myostatin-related disease, which includes an extracellular water-soluble domain of DLK1, a fragment of the extracellular water-soluble domain of DLK1, a mutant of the extracellular water-soluble domain of DLK1, or a fragment of the mutant as an active ingredient.

Also, the present invention provides a pharmaceutical composition for preventing or treating a myostatin-related disease, which includes a DLK1-Fc fusion protein, in which the extracellular water-soluble domain of DLK1 or a fragment thereof is conjugated to a human antibody Fc region, as an active ingredient.

According to still another aspect of the present invention, the present invention provides a method of treating a disease, which includes administering the pharmaceutical composition according to one exemplary embodiment of the present invention to a subject who has developed a myostatin-related disease or is likely to develop a myostatin-related disease.

In the present invention, the term "preventing" or "prevention" refers to all kinds of actions for inhibiting diseases or delaying the onset of the diseases by administration of the pharmaceutical composition according to one exemplary embodiment of the present invention. And, the term "treating" or "treatment" refers to all kinds of actions for improving diseases or beneficially changing the symptoms of diseases by administration of the pharmaceutical composition according to one exemplary embodiment of the present invention.

In the present invention, the term "subject" refers to an animal, such as a human, a monkey, a dog, a goat, a pig or a mouse, whose symptoms may be improved by administration of the composition according to one exemplary embodiment of the present invention. The composition according to one exemplary embodiment of the present invention may be applied to other commercially available animals, as well as the human beings (for the therapeutic, inhibitory or prophylactic purpose).

The pharmaceutical composition according to one exemplary embodiment of the present invention may be used without limitation as long as it can be used to treat amyostatin-related disease caused by overexpression of myostatin or signal transduction of myostatin/activin receptor type IIB. The myostatin-related disease may include various types of muscle wasting diseases, metabolic diseases, degenerative bone diseases, hypogonadism and cachexia developed by various causes, but the present invention is not limited thereto.

The muscle wasting diseases according to one exemplary embodiment of the present invention may include Duchenne's muscular dystrophy, progressive muscular dystrophy, Becker's type muscular dystrophy, facioscapulohumeral muscular dystrophy (i.e., Dejerine-Landouzy muscular dystrophy), limb girdle muscular dystrophy (i.e., Erb's muscular dystrophy), Emery Dreifuss muscular dystrophy, rigid spine syndromes, muscle-eye-brain diseases, amyotrophic lateral sclerosis (i.e., a Lou Gehrig's disease), congenital muscular dystrophy, infantile neuroaxonal muscular dystrophy, myotonic dystrophy (i.e., a Steinert's disease), nondystrophic myotonia, Charcot-Marie-Tooth diseases, chronic inflammatory neuropathy, distal myopathy, and a variety of other diseases as described in Emery Lancet 359:687-695 (2002) and Khurana et al, *Nat. Rev. Drug Disc* 2: 379-386 (2003), but the present invention is not limited thereto.

The metabolic diseases according to one exemplary embodiment of the present invention may include diabetes mellitus type II, noninsulin-dependent diabetes mellitus, and diabetic complications such as hyperglycemia, obesity and diabetic nephropathy, but the present invention is not limited thereto.

Additional examples of the muscle wasting disorders caused by the chronic diseases may include pulmonary cachexia such as a chronic obstructive pulmonary disease (COPD) and cystic fibrosis, cardiac cachexia, cancer- or tumor-related cachexia, rheumatoid cachexia, and cachexia caused by chemotherapeutic agents, but the present invention is not limited thereto.

In the present invention, the term "cachexia" refers to a condition in which the muscle wasting and the loss of lean body mass are promoted by the various diseases.

In addition to the myostatin inhibitors, the pharmaceutical composition according to one exemplary embodiment of the present invention may include therapeutic active ingredients, other adjuvants, and pharmaceutically available carriers. Proper examples of the carriers, excipients and diluents that may be included in such a composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and a mineral oil. When formulated, the composition may further include a conventional additive such as a filler, a bulking agent, a binder, a disintegrating agent, a surfactant, an anti-coagulating agent, a lubricant, a wetting agent, a flavoring agent, an emulsifying agent, or a preservative.

The pharmaceutical composition may be used in the form of a typical medicinal preparation. When formulated, the pharmaceutical composition may include a pharmaceutically available diluent or excipient. The composition according to one exemplary embodiment of the present invention may be formulated into various forms, for example, oral formulations, such as a powder, granule, tablet, capsule, suspension, emulsion, syrup, or aerosol, and a sterile injectable solution. Also, the composition may be administered through various routes of administration including oral administration or intravenous, intraperitoneal, subcutaneous, rectal or local administration.

The solid preparation for oral administration may include a tablet, a pill, powder, a granule, a capsule, etc. In this case, such a solid preparation is formulated by mixing at least one excipient, for example, starch, calcium carbonate, sucrose, lactose or gelatin, with the composition. Also, lubricants such as magnesium stearate and talc may be used in addition to the simple excipients.

The liquid preparation for oral administration may be a suspension, a liquid for internal use, an emulsion, syrup, etc. Such a liquid preparation may include various excipients, for example, a wetting agent, a sweetening agent, an aromatic, and a preservative, in addition to simple diluents (for example, water, and liquid paraffin) widely used in the related art.

The preparation for parenteral administration includes a sterilized aqueous solution, a water-insoluble solvent, a suspension, an emulsion, a lyophilized preparation, and a suppository. Propylene glycol, polyethylene glycol, a vegetable oil such as olive oil, or an injectable ester such as ethyl oleate may be used as the water-insoluble solvents and the suspension. Bases of the injections may include conventional additives such as a disintegrating agent, an isotonic agent, a suspending agent, an emulsifying agent, a stabilizing agent, and preservative.

According to one exemplary embodiment of the present invention, the term "administering" or "administration" refers to a process of providing a predetermined dose of a material to a patient using any proper methods. The composition according to one exemplary embodiment of the present invention may be administered orally or parenterally through all the typical routes of administration as long as the routes of administration can be used to deliver the composition to target tissues. Also, the composition may be administered using any devices capable of delivering the active ingredient to target cells.

The composition according to one exemplary embodiment of the present invention may be administered at a therapeutically effective dose.

In the present invention, the term "therapeutically effective dose" refers to a sufficient amount to treat a disease at a reasonable benefit/risk ratio at which the composition is applicable to medical treatment. In this case, a level of the effective dose may be determined according to the kind and severity of a patient's disease, the activities and sensitivity of a drug, an administration time, a route of administration, and an excretion rate, a treatment period, elements including drugs used together, and other elements well known in the field of medicine. The composition according to one exemplary embodiment of the present invention may be administered as a separate therapeutic agent, or administered in combination of other therapeutic agents. In this case, the composition may be administered sequentially or simultaneously with conventional therapeutic agents, and administered at a single dose or divided doses. Considering all the above-described elements, it is important to administer the composition at a minimum dose to obtain the maximum effects without any side-effects, and thus the minimum dose may be readily determined by those skilled in the related art.

Further, the dose of the compound according to one exemplary embodiment of the present invention may vary according to an absorption rate into the body, the body weight, age, gender, and health condition of a patient, diet, an administration time, a method of administration, an excretion rate, and severity of a disease. To achieve the desirable effects, however, the compound according to one exemplary embodiment of the present invention may be administered daily at a dose of 0.001 to 150 mg/kg, and preferably a dose of 0.01 to 100 mg/kg. The composition may be administered once a day, or administered in divided doses. The dose is not intended to limit the scope of the present invention in any aspects.

According to yet another aspect of the present invention, the present invention provides a kit for diagnosing a myostatin-related disease, which includes an antibody or an aptamer specifically binding to DLK1-myostatin, DLK1-ACVR2B, or a soluble fragment thereof.

The diagnostic kit according to one exemplary embodiment of the present invention includes an ELISA kit, or a sandwich ELISA kit, but the present invention is not limited thereto. Preferably, the kit for diagnosing a myostatin-related disease may also be configured to further include at least kinds of constitutive compositions, solutions, or devices, which are suitable for analysis methods. Also, the diagnostic kit may be preferably characterized in that it includes an essential element required to perform ELISA. The ELISA kit includes an antibody specific to the protein. The antibody has high specificity and affinity to each marker protein and shows no cross reactivity with other proteins. In this case, the antibody may be a monoclonal antibody, a polyclonal antibody, or a recombinant antibody. Further, the ELISA kit may include an antibody specific to a control protein. In addition, the ELISA kit may include a reagent capable of detecting bound antibodies, for example, labeled secondary antibodies, chromophores, enzymes (e. g., conjugated to antibodies) and substrates thereof, or other substances capable of binding to the antibodies.

[Mode for invention]

Hereinafter, the present invention will be described in further detail with reference to the following preferred Examples. However, it should be understood that the following Examples are given by way of illustration of the present invention only, and are not intended to limit the scope of the present invention, as apparent to those skilled in the art.

EXAMPLE 1

Preparation of Water-Soluble DLK1 and DLK1-Fc Fusion Protein

An extracellular water-soluble domain of DLK1 (hereinafter referred to as "water-soluble DLK1") and a DLK1-Fc fusion protein (hereinafter referred to as "DLK1-Fc") in which a human antibody Fc region was conjugated to water-soluble DLK1 as used herein in these Examples were prepared according to a method as described in Korean Patent No. 10-0982170.

EXAMPLE 2

Preparation of ACVR2B-Fc Fusion Protein

ACVR2B-Fc as used herein in these Examples was prepared by fusing an extracellular domain of ACVR2B set forth in SEQ ID NO: 1 to human antibody Fc, followed by using the same vector and the same expression and purification methods as described in Example 1.

EXAMPLE 3

Construction and Verification of Human Antibody (B09) Specifically Binding to Water-Soluble Region of DLK1

3-1. Construction of Human Antibody Specifically Binding to Water-Soluble Region of DLK1

<3-1-1> Construction of Library Phage $2.7 \times 10^{10}$ scFv library cells derived from a human showing diversities were cultured at a temperature of 37° C. for 2 to 3 hours in a medium (3 L) supplemented with 2×YTCM [tryptone (CONDA, 1612.00) 17 g, yeast extract (CONDA, 1702.00) 10 g, NaCl (Sigma, S7653-5 kg) 5 g, chloramphenicol (Sigma, C0857) 34 µg/ml)], 2% glucose (Sigma, G5400), and 5 mM $MgCl_2$ (Sigma, M2393) ($OD_{600}$=0.5 to 0.7), and infected with a helper phage. Thereafter, the infected scFv library cells were cultured at a temperature of 30° C. for 16 hours in a medium supplemented with 2×YTCMK [2×YT CM, kanamycin (Sigma, K1876) 70 µg/ml, and 1 mM IPTG (ELPISBIO, IPTG025)]. The cultured cells were centrifuged (at 4,500 rpm and 4° C. for 15 minutes), and 4% PEG (Fluka, 81253) 6000 and 3% NaCl (Sigma, S7653) were added to the supernatant, which was then thoroughly dissolved. Then, the resulting mixture was reacted on ice for an hour. The mixture was again centrifuged (at 8,000 rpm and 4° C. for 20 minutes), and the pellet was dissolved in PBS, and centrifuged (at 12,000 rpm and 4° C. for 10 minutes) to obtain a supernatant including a library phage, which was then transferred to a new tube and stored at 4° C.

<3-1-2> Preparation of Monoclonal Antibodies (1) Panning Procedure

30 µg of the purified DLK1-Fc obtained in Example 1 was put into an Immunosorb tube (Nunc 470319), coated at 4° C. for approximately 16 hours in 4 ml of a coating buffer [$Na_2CO_3$ (Sigma, S7795) 1.59 g, $NaHCO_3$ (Sigma, S8875) 2.93 g, and $NaN_3$ (Sigma, S2002), 0.2 g] using a rotator, dissolved in PBS at room temperature for 2 hours, and then blocked with skim milk [(BD,232100)-4% in 1×PBS] in an immunotube. 2 ml of the resulting library phage was put into the immunotube, reacted at room temperature for 2 hours, and washed five times with PBST (0.05%) and twice with PBS. After the washing, only the scFv phages specifically binding to the immunotube were eluted with 100 mM TEA (Sigma T-0886), and E. coli (XL-Blue, Stratagene, 200249) was then infected with the eluted phages, which were then amplified. The second and third panning procedures were performed on the phages amplified in the first panning procedure in the same manner in increasing numbers (washing 13 times in the second panning and 23 times in the third panning).

As a result, the increases in titers of the antibodies in the panning procedure are listed in the following Table 1.

TABLE 1

| Target antigen | No. of panning cycles | Initial No. of phages | No. of bound phages |
|---|---|---|---|
| DLK1-Fc | $1^{st}$ | $4.6 \times 10^{13}$ | $6 \times 10^7$ |
| | $2^{nd}$ | $2 \times 10^{12}$ | $1.4 \times 10^6$ |
| | $3^{rd}$ | $1.49 \times 10^{14}$ | $6.93 \times 10^9$ |

(2) Search for Phage Antibodies Using Phage Enzyme-Linked Immunosorbent Assay (ELISA)

A. Determination of Panning Results

Each of the frozen cell stocks obtained in the first to third panning procedures was added to 5 ml of a medium containing 2×YTCM, 2% glucose, and 5 mM $MgCl_2$ so that the optical density reached $OD_{600}$=0.1, and cultured at 37° C. for 2 to 3 hours ($OD_{600}$=0.5 to 0.7). Thereafter, the cultured cells were infected with an M1 helper phage, and cultured at a temperature of 30° C. for 16 hours in a medium containing 2×YTCMK, 5 mM $MgCl_2$, and 1 mM IPTG. The cultured cells were centrifuged (at 4,500 rpm and 4° C. for 15 minutes), and the supernatant (with panned poly scFv phages) was transferred to a new tube. A 96-well immunoplate (NUNC 439454) was coated with antigens at a concentration of 100 ng per well by treating the immunoplate with the antigens at 4° C. for approximately 16 hours in a coating buffer, and each well was blocked with skim milk (4%) dissolved in PBS. Each well was washed with 0.2 ml of PBS-Tween 20 (0.05%), and an undiluted solution of the panned poly scFV phages, and solutions obtained by diluting the undiluted solution of the panned poly scFV phages at 1:5, 1:25, 1:125, 1:625, and 1:3,125 were added to each well at a concentration of 100 µl, and reacted at room temperature for 2 hours. Each well was washed four times with 0.2 ml of PBS-Tween 20 (0.05%), and a secondary antibody, anti-M13-HRP (Amersham 27-9421-01), was diluted at 1:2000, added to each well, and then reacted at room temperature for an hour. Each well was washed with 0.2 ml of PBS-Tween 20 (0.05%), and a substrate solution in which an OPD tablet (Sigmap 8787-TAB) was dissolved in a PC buffer [$C_6H_8O_7 \cdot H_2O$ (Sigma, C0706) 5.1 g, and $Na_2HPO_4$ (Sigma, S7907) 7.3 g] was prepared, added to each well at a concentration of 100 µl per well to perform a chromogenic reaction for 10 minutes. Then, the cells were measured for optical density at 490 nm using a spectrophotometer (Molecular Device, USA).

Accordingly, as shown in FIG. 1, it could be seen that the binding capacity to the antigens started to increase from the secondary polyclonal scFv-phage pools and was saturated in the tertiary polyclonal scFv-phage pools (FIG. 1).

B. Screening of Monoclonal Antibodies

Colonies obtained from a group of the polyclonal phage antibodies having high binding capacity were cultured at a temperature of 37° C. for 16 hours in a 96-deep well plate (Bioneer 90030) containing 1 ml of a medium supplemented with 2×YTCM, 2% glucose, and 5 mM $MgCl_2$. 100 to 200 µl of the cultured cells were taken, and diluted with 1 ml of a medium supplemented with 2×YTCM, 2% glucose, and 5 mM $MgCl_2$ so that the $OD_{600}$ value of the cultured cells reached 1. Thereafter, the cells were cultured at a temperature of 37° C. for 2 to 3 hours in a 96-deep well plate so that the $OD_{600}$ value reached 0.5 to 0.7. Then, the cells were infected with an M helper phage so that a multiplicity of infection (MOI) value became 1:20, and then cultured at a temperature of 30° C. for 16 hours in a medium supplemented with 2×YTCMK, 5 mM MgCl$_2$, and 1 mM IPTG. The cultured cells were centrifuged (at 4,500 rpm and 4° C. for 15 minutes) to collect a supernatant. Then, the supernatant was thoroughly dissolved in 4% PEG 6000 and 3% NaCl, and reacted on ice for an hour. The resulting reaction mixture was centrifuged again (at 8,000 rpm and 4° C. for 20 minutes), and the pellet was dissolved in PBS, and then centrifuged (at 12,000 rpm and 4° C. for 10 minutes) to obtain a supernatant, which was transferred to a new tube and stored at 4° C. Subsequently, a 96-well immunoplate was coated with antigens at a concentration of 100 ng per well by treating the immunoplate with the antigens at 4° C. for 16 hours, and each well was then blocked with skim milk (4%) dissolved in PBS. Each well was washed with 0.2 ml of PBS-Tween 20 (0.05%), and 100 μl of the monoclonal scFv-phages obtained by the above-described method were added to each well, and then reacted at room temperature for 2 hours. Each well was again washed four times with 2 ml of PBS-Tween 20 (0.05%), and a secondary antibody, anti-M13-HRP, was diluted at 1:2000, added to each well, and then reacted at room temperature for an hour. Each well was washed with 2 ml of PBS-Tween 20, colorimetrically developed, and then measured for optical density at 490 nm. As a result, it was revealed that the 27 single phage clones having a binding capacity of 2 or more to the antigens were screened, as listed in the following Table 2.

3'), 3 μl of a 10× buffer, 0.6 μl of a 10 mM dNTP mix, and 24.8 μl of distilled water were mixed, and the resulting mixture was subjected to colony PCR (iCycler iQ, BIO-RAD). The PCR programming conditions are listed in the following Table 3.

TABLE 3

| Temperature | Time | Cycle |
|---|---|---|
| 95° C. | 5 minutes | |
| 95° C. | 30 seconds | 30 cycles |
| 56° C. | 30 seconds | |
| 72° C. | 1 minute | |
| 72° C. | 10 minutes | |
| 4° C. | | |

The colony PCR products were determined on 1% agarose gel (Seakem LE, CAMERES 50004), and digested with 0.2 μl of Bst NI (Roche 11288075001, 10 U/μl) at 37° C. for 2 to 3 hours. The reaction conditions are listed in the following Table 4. The digested products were determined on 8% DNA polyacrylamide gel.

TABLE 4

| 10× Buffer | 3 μl |
|---|---|
| Colony PCR product | 10 μl |
| Bst NI (10 U/μl) | 0.2 μl |
| Distilled water | 16.8 μl |

TABLE 2

| | 1 | 2 | 3 | 4 | 5 | 6 | 7 | 8 | 9 | 10 | 11 | 12 |
|---|---|---|---|---|---|---|---|---|---|---|---|---|
| DLK1 | | | | | | | | | | | | |
| A | 0.1129 | 0.0716 | 0.0482 | 3.1152 | 2.9859 | 0.4549 | 0.3612 | 2.92 | 0.0469 | 2.8295 | 0.2175 | 1.0026 |
| B | 0.8858 | 0.8553 | 2.0914 | 0.788 | 2.762 | 2.6351 | 2.8837 | 0.1342 | 2.3259 | 0.1396 | 2.5018 | 3.501 |
| C | 0.4976 | 0.2852 | 2.466 | 0.2239 | 0.1128 | 1.2413 | 2.9255 | 2.1548 | 0.2169 | 0.0608 | 0.2132 | 0.1591 |
| D | 0.2025 | 0.1882 | 0.1109 | 0.0586 | 0.8865 | 0.0749 | 0.0849 | 0.1145 | 0.8514 | 0.0572 | 0.1653 | 2.4751 |
| E | 0.0907 | 0.1001 | 0.0418 | 0.047 | 2.2329 | 2.3476 | 2.3778 | 0.7165 | 0.0919 | 0.7527 | 0.1737 | 0.2233 |
| F | 0.1659 | 0.2324 | 0.4055 | 2.9152 | 0.2405 | 0.933 | 0.3682 | 0.1608 | 0.2258 | 0.1668 | 2.8944 | 2.9681 |
| G | 0.0433 | 0.3815 | 0.2245 | 2.8355 | 2.5814 | 3.0216 | 0.752 | 0.3455 | 0.0609 | 0.4363 | 0.1964 | 0.0504 |
| H | 0.1044 | 2.8427 | 2.7085 | 0.296 | 0.2403 | 2.1306 | 2.8803 | 1.6389 | 3.033 | 0.5009 | 2.7793 | 3.1994 |
| MYC | | | | | | | | | | | | |
| A | 0.2003 | 0.0474 | 0.0487 | 0.5068 | 0.7838 | 1.4922 | 0.4492 | 0.5538 | 0.0557 | 1.2823 | 0.1523 | 0.2432 |
| B | 1.357 | 0.7667 | 1.4038 | 1.1973 | 0.5932 | 0.8478 | 0.5129 | 0.1191 | 0.0918 | 0.7688 | 0.316 | 0.0526 |
| C | 0.2966 | 0.0741 | 0.2871 | 0.1538 | 0.0683 | 0.6353 | 0.5938 | 0.3595 | 0.6692 | 0.1009 | 0.1206 | 0.2206 |
| D | 0.1631 | 0.4308 | 0.078 | 0.045 | 0.5783 | 0.0632 | 0.0538 | 0.052 | 2.1443 | 0.0511 | 0.106 | 0.0889 |
| E | 0.0856 | 0.6073 | 0.0465 | 0.0435 | 0.1722 | 0.1883 | 0.4694 | 0.0867 | 0.0639 | 0.272 | 0.3112 | 0.1566 |
| F | 0.1285 | 0.4057 | 0.1421 | 1.0637 | 0.1115 | 1.1193 | 0.0898 | 1.0797 | 0.1751 | 0.1401 | 0.4419 | 0.524 |
| G | 0.0662 | 0.3396 | 0.0844 | 0.9974 | 2.9974 | 0.6732 | 0.6083 | 0.2278 | 0.0496 | 0.5198 | 0.0561 | 0.0551 |
| H | 0.0479 | 0.5654 | 1.1204 | 0.4634 | 0.066 | 0.8632 | 1.0213 | 0.6574 | 0.8562 | 0.1146 | 0.9677 | 0.6741 |
| FC | | | | | | | | | | | | |
| A | 0.0535 | 0.0726 | 0.0731 | 0.0791 | 0.0704 | 0.1111 | 0.0748 | 0.0709 | 0.0535 | 0.0828 | 0.0591 | 0.2558 |
| B | 0.1375 | 0.4065 | 0.0851 | 0.0702 | 0.0575 | 0.0472 | 2.8291 | 0.0717 | 0.0786 | 0.0743 | 0.0548 | 0.0451 |
| C | 0.0524 | 0.0555 | 0.0521 | 0.0745 | 0.0455 | 0.0825 | 2.8824 | 0.0559 | 0.0772 | 0.0485 | 0.0663 | 0.061 |
| D | 0.0519 | 0.0686 | 0.0447 | 0.0722 | 0.0431 | 0.0455 | 0.0482 | 0.0528 | 0.0498 | 0.1141 | 0.0651 | 0.0831 |
| E | 0.0496 | 0.0543 | 0.0419 | 0.0587 | 0.0472 | 0.0481 | 0.0558 | 0.2673 | 0.0492 | 0.1508 | 0.0601 | 0.0577 |
| F | 0.0614 | 0.0584 | 0.0528 | 0.0879 | 0.0553 | 0.1223 | 0.0792 | 0.0756 | 0.0661 | 0.0922 | 0.0658 | 0.0757 |
| G | 0.0456 | 0.0687 | 0.0521 | 0.1171 | 2.079 | 0.0689 | 0.547 | 0.0991 | 0.0874 | 0.2255 | 0.1894 | 0.0457 |
| H | 0.0594 | 0.0642 | 0.049 | 0.0705 | 0.0608 | 0.0766 | 0.1107 | 0.0819 | 0.0701 | 0.1204 | 0.0592 | 0.0539 |

(3) Classification and Inspection of Monoclonal Phages

A. Verification by Fingerprinting

Figure 2:
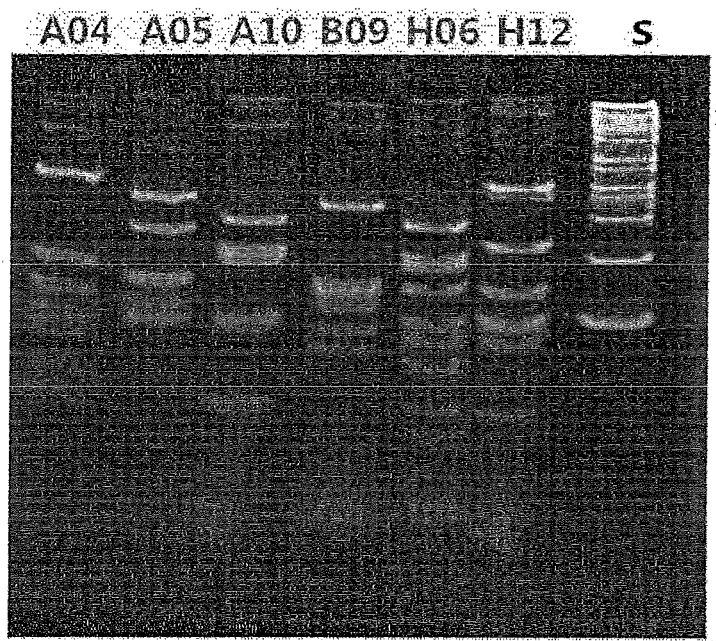
FIG. 2 shows the results obtained by determining the diversity of a monoclonal antibody against water-soluble DLK1 through DNA fingerprinting.

1 μl of the 27 monoclonal colonies against the primarily screened DLK1-Fc, 0.2 μl of Taq DNA polymerase (GenDocs Inc., 5 U/μl), 0.2 μl of 50 p/μl forward primer (SEQ ID NO: 2: 5'-CTAGATAACGAGGGCAAATCATG-3') and reverse primer (SEQ ID NO: 3: 5'-CGTCACCAATGAAACCATC- As a result, it was revealed that the fragments of the monoclonal phage antibodies digested by Bst NI showed the diversities, as shown in FIG. 2, deducing that the 6 different antibodies were screened.

B. Verification by DNA Sequence Analysis

Six types of the monoclonal phages against the water-soluble DLK1 were cultured at a temperature of 37° C. for 16 hours in a medium (5 ml) supplemented with 2×YTCM, 2% glucose, and 5 mM MgCl$_2$. DNA was obtained from the cultured monoclonal phages using a DNA purification kit (Nuclogen 5112), and sequenced using a primer set forth in SEQ ID NO: 2 (SolGent, Korea). As a result, the CDR regions of VH and VL of the screened antibodies were identified, as listed in Table 5 and shown in FIG. 3, and the sequences of heavy chains (SEQ ID NOS: 35 to 40) and light chains (SEQ ID NOS: 41 to 46) of the respective antibodies are listed in the Sequence Listing.

TABLE 5

Grouping of Mono Phage for DLK1

| Clone Name | VH | Identities | CDR3-a.a seq | VL | Identities | CDR3-a.a seq | Group | DLK1 | a-myc | Fc | Ratio |
|---|---|---|---|---|---|---|---|---|---|---|---|
| DLK1 A04 | VH1-3 | 263/294 (89.5%) | SVSAYG----SNYFDP | L8 | 268/286 (93.7%) | QQLNS-YPL | 1 | 3.1152 | 0.5068 | 0.0791 | 6.146803473 |
| DLK1 A05 | VH3-9 | 277/290 (95.5%) | SGGYGGN--TNWYFDL | V1-13 | 276/295 (93.6%) | QSYDSRLGV | 2 | 2.9859 | 0.7838 | 0.0704 | 3.809517734 |
| DLK1 A10 | VH3-9 | 287/292 (98.3%) | GPGLATG---KGYADY | L5 | 268/284 (94.4%) | QQGHS-FPY | 3 | 2.8295 | 1.2823 | 0.0828 | 2.206581923 |
| DLK1 B09 | VH3-23 | 266/294 (90.5%) | GESCSGG--ACSDFDY | V1-4 | 263/285 (92.3%) | GSYAGSYTY | 4 | 2.3259 | 0.0918 | 0.0786 | 25.33660131 |
| DLK1 H06 | VH3-23 | 267/293 (91.1%) | S--------TAYLFDY | A27 | 257/272 (94.5%) | QHYGS-PLH | 5 | 2.1306 | 0.8632 | 0.0766 | 2.468257646 |
| DLK1 H12 | VH3-11 | 279/294 (94.9%) | LQGHCSGGACSNWFDA | O12 | 272/284 (95.8%) | QQGYG-TPY | 6 | 3.1994 | 0.6741 | 0.0539 | 4.746180092 |

The homologies beTween these antibodies and a group of germ line antibodies were examined using a NCBI's Ig BLAST program (www.ncbi.nlm.nih.gov/igblast/). As a result, the six phage antibodies specific to the water-soluble DLK1 were obtained. In this case, each heavy chain included two copies of VH3-9 and VH3-23, and one copy of each of VH3-11 and VH1-3. The amino acid sequences for the CDR3 of the heavy and light chains of the antibodies were analyzed, and it was confirmed that the phage antibodies had different sequences (FIG. 3).

(4) Characterization of Human Antibodies Against Water-Soluble DLK1

A. Analysis of Full-Length IgG Conversion

To convert the monoclonal phage antibodies against the water-soluble DLK into a full-length IgG vector in phages, the heavy chain was mixed with 1 µl of monoclonal DNA, 10 pmole/µl of forward and reverse primers of the heavy chain listed in Table 6, 5 µl of a 10× buffer, 1 µl of a 10 mM dNTP mix, 0.5 µl of a pfu DNA polymerase (SolGent, 2.5 U/µl), and distilled water, and the resulting mixture was subjected to colony PCR (iCycler iQ, BIO-RAD). The light chain was also subjected to colony PCR in the same manner using the forward and reverse primers of the light chain listed in Table 6.

TABLE 6

| Clone name | Forward primer | Reverse primer |
|---|---|---|
| | HC | |
| A04 HC | NATVH3-2 SEQ ID NO: 5 | NATJH-ALL SEQ ID NO: 8 |
| A05 HC | NATVH7-1 SEQ ID NO: 6 | |
| A10 HC | NATVH3-2 SEQ ID NO: 5 | |
| B09 HC | NATVH7-1 SEQ ID NO: 6 | |

TABLE 6-continued

| Clone name | Forward primer | Reverse primer |
|---|---|---|
| H06 HC | NATVH1-1 SEQ ID NO: 7 | |
| H12 HC | | |
| | LC | |
| A04 HC | NATVK6 SEQ ID NO: 9 | NATJK-R7 SEQ ID NO: 12 |

TABLE 6-continued

| Clone name | Forward primer | Reverse primer |
|---|---|---|
| A05 HC | NATVL13 SEQ ID NO: 10 | NATJL2-R SEQ ID NO: 13 |
| A10 HC | HATVK6 SEQ ID NO: 9 | NATJK-R5 SEQ FD NO: 14 |
| B09 HC | NATVL10 SEQ ID NO: 11 | NATJL1-R SEQ ID NO: 15 |
| H06 HC | NATVK6 SEQ ID NO: 9 | NATJK-R4 SEQ ID NO: 16 |
| H12 HC | | NATJK-R7 SEQ ID NO: 12 |

Figure 4:
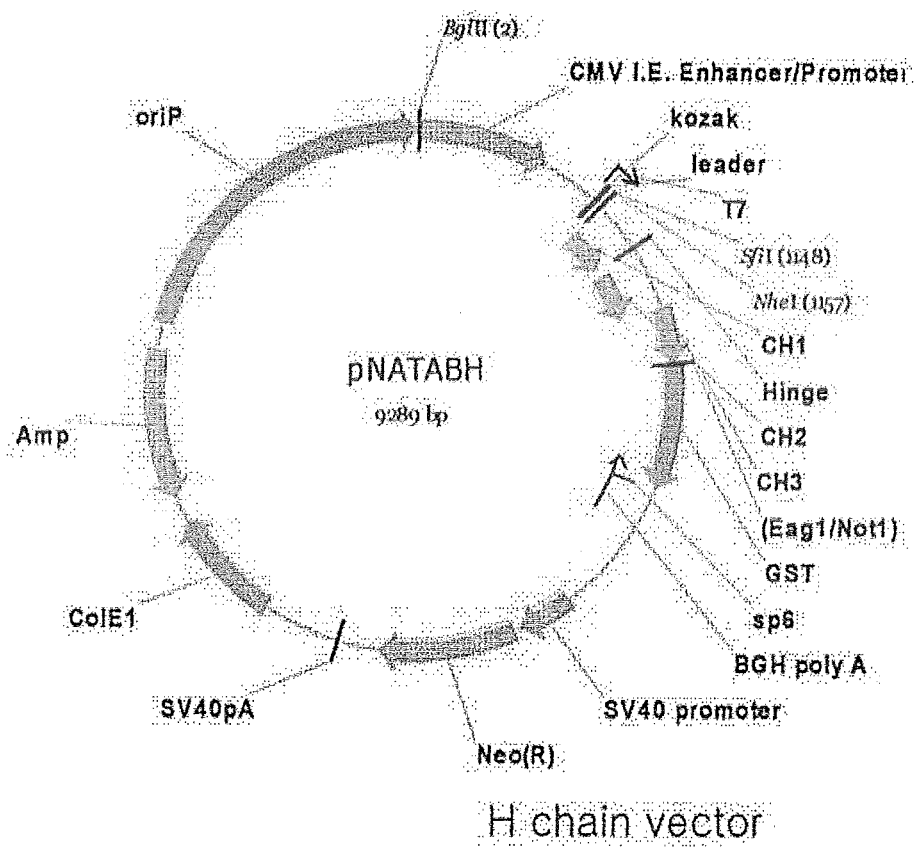
FIG. 4 shows a cleavage map of a pNATAB H vector.
Figure 5:
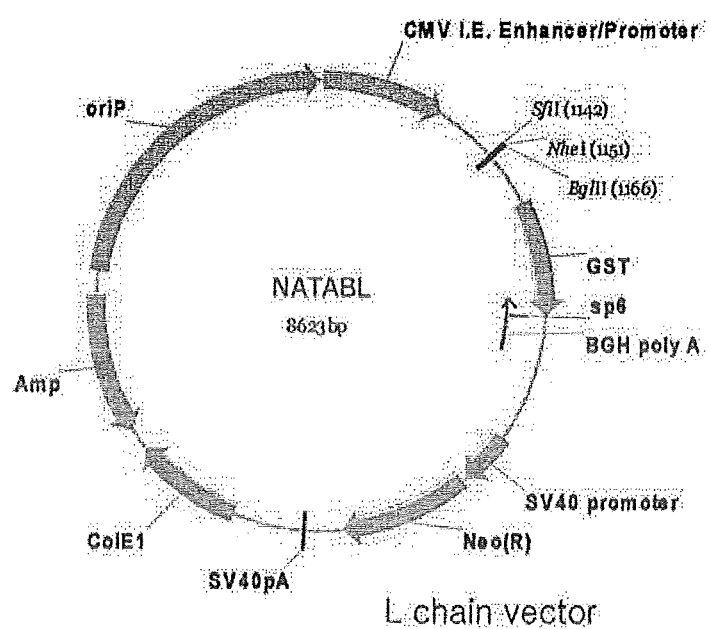
FIG. 5 shows a cleavage map of a pNATAB L vector.

A gene coding for the heavy chain obtained by PCR was purified using a DNA-gel extraction kit (Qiagen), mixed with 1 µl (10 ng) of a pNATAB H vector (FIG. 4), 15 µl of the heavy chain (100 to 200 ng), 2 µl of a 10× buffer, a ligase (1 U/µl), and distilled water, and then ligated with the vector while being kept at room temperature for 1 to 2 hours. The vector was kept on ice together with transformant cells (XL1-blue) for 30 minutes, and then transformed by applying heat shock to the cells at 42° C. for 90 seconds. The transformed cells were kept on ice for 5 minutes, and 1 ml of a LB medium was added to the cells, which were then cultured at 37° C. for an hour. Thereafter, the cells were spread on a solid LB Amp medium, and then cultured at 37° C. for 16 hours. Single colonies were seeded in 5 ml of a liquid LB Amp medium, and then cultured at 37° C. for 16 hours. DND was extracted from the culture broth using a DNA-preparative kit (Nuclogen). Also, the light chain was extracted in the same manner using a pNATAB L vector (FIG. 5).

The obtained DNAs were sequenced using a CMV-proF primer (SEQ ID NO: 4: AAA TGG GCG GTA GGC GTG) (SolGent). As a result, it was confirmed that the sequences of the heavy and light chains of the six clonal phages against the DLK1-Fc converted into the full-length IgG matched the sequences of the phage antibodies.

3-2. Verification of Human Antibodies Specifically Binding to Water-Soluble Region of DLK1

Figure 6:
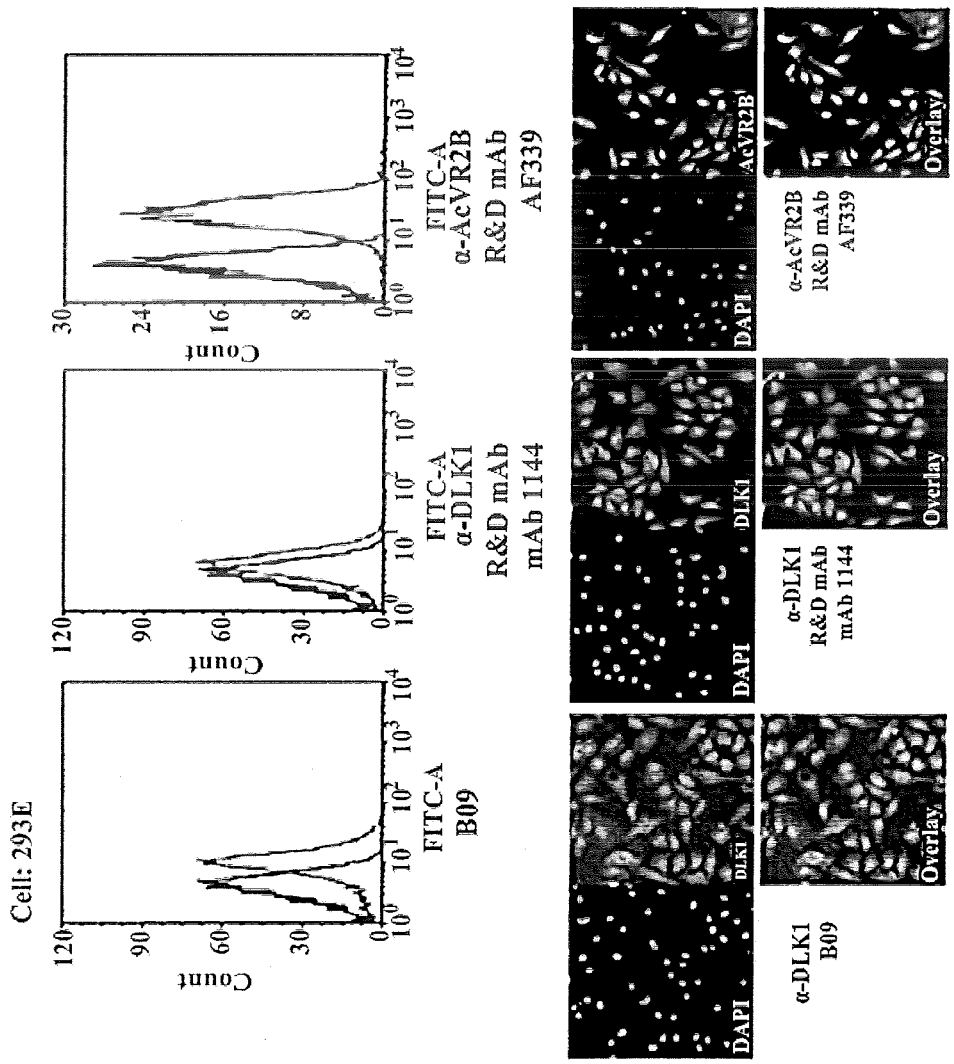
FIG. 6 shows the flow cytometry results (upper panels) and the immunofluorescent staining results (lower panels) showing that a B09 antibody is specifically bound to a water-soluble moiety of DLK1.

To determine the binding affinity of human antibodies specifically binding to a water-soluble region of DLK1 constructed in Example 3-1, 293E cells expressing DLK1 were subjected to flow cytometry using a representative B09 antibody among the six human antibodies. The flow cytometry results are shown in FIG. 6. In this case, the binding affinities of DLK1 monoclonal antibody and ACVR2B antibody purchased from R&D were measured.

As a result, it could be seen that the B09 antibody was specifically bound to the water-soluble region of DLK1, as shown in FIG. 6. Also, it could be seen that the DLK1 monoclonal antibody and the ACVR2B antibody purchased from R&D were also bound to the DLK1 and the ACVR2B, respectively.

EXAMPLE 4

Construction and Verification of Human Antibodies (F08) Specifically Binding to Water-Soluble Region of ACVR2B 4-1. Construction of Human Antibodies (F08) Specifically Binding to Water-Soluble Region of ACVR2B <4-1-1> Construction of Library Phage $2.7 \times 10^{10}$ scFv library cells derived from a human showing diversities were cultured at a temperature of 37° C. for 2 to 3 hours in a medium (3 L) supplemented with 2×YTCM [tryptone (CONDA, 1612.00) 17 g, yeast extract (CONDA, 1702.00) 10 g, NaCl (Sigma, S7653-5 kg) 5 g, and chloramphenicol (Sigma, C0857) 34 µg/ml)], 2% glucose (Sigma, G5400), and 5 mM $MgCl_2$(Sigma, M2393) ($OD_{600}$=0.5 to 0.7), and infected with a helper phage. Thereafter, the infected scFv library cells were cultured at a temperature of 30° C. for 16 hours in a medium supplemented with 2×YTCMK [2×YT CM, kanamycin (Sigma, K1876) 70 µg/ml, and 1 mM IPTG (ELPISBIO, IPTG025)]. The cultured cells were centrifuged (at 4,500 rpm and 4° C. for 15 minutes), and 4% PEG (Fluka, 81253) 6000 and 3% NaCl (Sigma, S7653) were added to the supernatant, which was then thoroughly dissolved. Then, the resulting mixture was reacted on ice for an hour. The mixture was again centrifuged (at 8,000 rpm and 4° C. for 20 minutes), and the pellet was dissolved in PBS, and centrifuged (at 12,000 rpm and 4° C. for 10 minutes) to obtain a supernatant including a library phage, which was then transferred to a new tube and stored at 4° C.

<4-1-2> Preparation of Monoclonal Antibodies (1) Panning Procedure

30 µg of the ACVR2B-Fc prepared in Example 2 was put into an Immunosorb tube (Nunc 470319), coated at 4° C. for approximately 16 hours in 4 ml of a coating buffer [$Na_2CO_3$ (Sigma, S7795) 1.59 g, $NaHCO_3$ (Sigma, S8875) 2.93 g, and $NaN_3$ (Sigma, S2002), 0.2 g] using a rotator, dissolved in PBS at room temperature for 2 hours, and then blocked with skim milk [(BD,232100)-4% in 1×PBS] in an immunotube. 2 ml of the resulting library phage was put into the immunotube, reacted at room temperature for 2 hours, and washed five times with PBST (0.05%) and twice with PBS. After the washing, only the scFv phages specifically binding to the immunotube were eluted with 100 mM TEA (Sigma T-0886), and E. coli (XL-Blue, Stratagene, 200249) was then infected with the eluted phages, which were then amplified. The second and third panning procedures were performed on the phages amplified in the first panning procedure in the same manner in increasing numbers (washing 13 times in the second panning and 23 times in the third panning).

As a result, the increases in titers of the antibodies in the panning procedure are listed in the following Table 7.

TABLE 7

| Target antigen | Panning cycles | Initial No. of phages | No. of bound phages |
|---|---|---|---|
| ACVR2B-Fc | $1^{st}$ | $4.6 \times 10^{13}$ | $1.4 \times 10^8$ |
| | $2^{nd}$ | $3.64 \times 10^{13}$ | $9.8 \times 10^5$ |
| | $3^{rd}$ | $5.83 \times 10^{13}$ | $4.4 \times 10^7$ |

(2) Search for Phage Antibodies Using ELISA

A. Determination of Panning Results

Each of the frozen cell stocks obtained in the first to third panning procedures was added to 5 ml of a medium containing 2×YTCM, 2% glucose, and 5 mM $MgCl_2$ so that the optical density reached $OD_{600}$=0.1, and cultured at 37° C. for 2 to 3 hours ($OD_{600}$=0.5 to 0.7). Thereafter, the cultured cells were infected with an M1 helper phage, and cultured at a temperature of 30° C. for 16 hours in a medium containing 2×YTCMK, 5 mM $MgCl_2$, and 1 mM IPTG. The cultured cells were centrifuged (at 4,500 rpm and 4° C. for 15 minutes), and the supernatant (with panned poly scFv phages) was transferred to a new tube. A 96-well immunoplate (NUNC 439454) was coated with antigens at a concentration of 100 ng per well by treating the immunoplate with the antigens at 4° C. for approximately 16 hours in a coating buffer, and each well was blocked with skim milk (4%) dissolved in PBS. Each well was washed with 0.2 ml of PBS-Tween 20 (0.05%), and an undiluted solution of the panned poly scFV phages, and solutions obtained by diluting the undiluted solution of the panned poly scFV phages at 1:5, 1:25, 1:125, 1:625, and 1:3,125 were added to each well at a concentration of 100 µl, and reacted at room temperature for 2 hours. Each well was washed four times with 0.2 ml of PBS-Tween 20 (0.05%), and a secondary antibody, anti-M13-HRP (Amersham 27-9421-01), was diluted at 1:2000, added to each well, and then reacted at room temperature for an hour. Each well was washed with 0.2 ml of PBS-Tween 20 (0.05%), and a substrate solution in which an OPD tablet (Sigmap 8787-TAB) was dissolved in a PC buffer [$C_6H_8O_7 \cdot H_2O$ (Sigma, C0706) 5.1 g, and $Na_2HPO_4$ (Sigma, S7907) 7.3 g] was prepared, added to each well at a concentration of 100 µl per well to perform a chromogenic reaction for 10 minutes. Then, the cells were measured for optical density at 490 nm using a spectrophotometer (Molecular Device, USA).

B. Screening of Monoclonal Antibodies

Colonies obtained from a group of the polyclonal phage antibodies having high binding capacity were cultured at a temperature of 37° C. for 16 hours in a 96-deep well plate (Bioneer 90030) containing 1 ml of a medium supplemented with 2×YTCM, 2% glucose, and 5 mM $MgCl_2$. 100 to 200 µl of the cultured cells were taken, and diluted with 1 ml of a medium supplemented with 2×YTCM, 2% glucose, and 5 mM $MgCl_2$ so that the $OD_{600}$ value of the cultured cells reached 1. Thereafter, the cells were cultured at a temperature of 37° C. for 2 to 3 hours in a 96-deep well plate so that the $OD_{600}$ value reached 0.5 to 0.7. Then, the cells were infected with an M1 helper phage so that an MOI value became 1:20, and then cultured at a temperature of 30° C. for 16 hours in a medium supplemented with 2×YTCMK, 5 mM $MgCl_2$, and 1 mM IPTG. The cultured cells were centrifuged (at 4,500 rpm and 4° C. for 15 minutes) to collect a supernatant. Then, the supernatant was thoroughly dissolved in 4% PEG 6000 and 3% NaCl, and reacted on ice for an hour. The resulting reaction mixture was centrifuged again (at 8,000 rpm and 4° C. for 20 minutes), and the pellet was dissolved in PBS, and then centrifuged (at 12,000 rpm and 4° C. for 10 minutes) to obtain a supernatant, which was transferred to a new tube and stored at 4° C. Subsequently, a 96-well immunoplate was coated with antigens at a concentration of 100 ng per well by treating the immunoplate with the antigens at 4° C. for 16 hours, and each well was then blocked with skim milk (4%) dissolved in PBS. Each well was washed with 0.2 ml of PBS-Tween 20 (0.05%), and 100 µl of the monoclonal scFv-phages obtained by the above-described method were added to each well, and then reacted at room temperature for 2 hours. Each well was again washed four times with 2 ml of PBS-Tween 20 (0.05%), and a secondary antibody, anti-M13-HRP, was diluted at 1:2000, added to each well, and then reacted at room temperature for an hour. Each well was washed with 2 ml of PBS-Tween 20, colorimetrically developed, and then measured for optical density at 490 nm. As a result, it was revealed that the 36 single phage clones having a binding capacity of 2 or more to the antigens were screened, as listed in the following Table 8.

CATC-3'), 3 µl of a 10× buffer, 0.6 µl of a 10 mM dNTP mix, and 24.8 µl of distilled water were mixed, and the resulting mixture was subjected to colony PCR (iCycler iQ, BIO-RAD). The PCR programming conditions are listed in the following Table 9.

TABLE 9

| Temperature | Time | Cycle |
| --- | --- | --- |
| 95° C. | 5 minutes | |
| 95° C. | 30 seconds | 30 cycles |
| 56° C. | 30 seconds | |
| 72° C. | 1 minute | |
| 72° C. | 10 minutes | |
| 4° C. | | |

The colony PCR products were determined on 1% agarose gel (Seakem LE, CAMERES 50004), and digested with 0.2 µl of Bst NI (Roche 11288075001, 10 U/µl) at 37° C. for 2 to 3 hours. The reaction conditions are listed in the following Table 10. The digested products were determined on 8% DNA polyacrylamide gel.

TABLE 10

| 10× Buffer | 3 µl |
| --- | --- |
| Colony PCR product | 10 µl |
| Bst NI (10 U/µl) | 0.2 µl |
| Distilled water | 16.8 µl |

TABLE 8

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| ACVR2B | | | | | | | | | | | | |
| A | 0.0446 | 0.0443 | 0.0451 | 0.0555 | 0.0507 | 2.9605 | 2.6546 | 0.0484 | 2.1802 | 2.948 | 0.0656 | 2.6826 |
| B | 0.0576 | 2.9014 | 0.0447 | 0.0446 | 0.0427 | 0.043 | 0.0447 | 2.6446 | 0.0489 | 1.5 | 2.9913 | 2.7552 |
| C | 0.0467 | 0.0456 | 2.9853 | 0.0834 | 0.0414 | 0.0627 | 2.9773 | 2.8572 | 2.3586 | 3.1073 | 1.8795 | 0.0439 |
| D | 2.6399 | 0.0625 | 0.0683 | 0.0438 | 2.906 | 0.0497 | 2.661 | 0.0521 | 2.3111 | 3.0192 | 3.0518 | 0.0524 |
| E | 0.0427 | 0.0452 | 0.0428 | 0.0573 | 0.0438 | 0.3144 | 0.0429 | 0.0418 | 2.0538 | 0.5258 | 3.2316 | 0.043 |
| F | 0.0444 | 0.0471 | 3.0313 | 0.0478 | 0.3107 | 0.0454 | 2.9075 | 2.9418 | 0.0421 | 0.0444 | 3.0727 | 3.2044 |
| G | 3.3126 | 0.0512 | 0.047 | 0.0448 | 0.0438 | 3.0064 | 0.0465 | 2.7927 | 2.2111 | 2.5613 | 0.0462 | 3.157 |
| H | 0.0453 | 1.2824 | 0.0442 | 0.0454 | 0.0463 | 0.0478 | 2.6954 | 0.3632 | 3.2283 | 1.9535 | 3.1269 | 3.1271 |
| a-MYC | | | | | | | | | | | | |
| A | 0.0447 | 0.0454 | 0.0428 | 0.0433 | 0.3051 | 0.7035 | 0.2132 | 0.044 | 1.1704 | 0.7631 | 0.0459 | 0.2891 |
| B | 0.0441 | 1.0609 | 0.0432 | 0.1338 | 0.0423 | 0.1197 | 0.0882 | 1.1603 | 0.0448 | 1.0292 | 0.6575 | 1.4565 |
| C | 0.0792 | 0.1558 | 1.2127 | 0.0464 | 0.0416 | 0.0419 | 0.4409 | 1.1703 | 0.231 | 0.8069 | 0.1634 | 0.0426 |
| D | 0.3254 | 0.0425 | 0.0449 | 0.0421 | 0.8795 | 0.0471 | 0.2409 | 0.0788 | 0.2134 | 0.5607 | 0.8336 | 0.0439 |
| E | 0.0533 | 0.0445 | 0.0427 | 0.0423 | 0.0419 | 0.1865 | 0.0794 | 0.045 | 0.1745 | 0.0822 | 0.8914 | 0.0417 |
| F | 0.0441 | 0.0423 | 1.9176 | 0.0589 | 0.0412 | 0.0974 | 1.2268 | 0.7833 | 0.0419 | 0.0432 | 0.9633 | 0.9558 |
| G | 1.2456 | 0.0421 | 0.0434 | 0.046 | 0.0436 | 0.6495 | 0.0415 | 1.4576 | 0.1575 | 0.6495 | 0.0418 | 1.0425 |
| H | 0.0443 | 1.7385 | 0.0423 | 0.0428 | 0.1027 | 0.043 | 0.2578 | 0.1527 | 1.6451 | 1.2449 | 1.3433 | 1.2197 |
| FC | | | | | | | | | | | | |
| A | 0.0439 | 0.0437 | 0.0447 | 0.046 | 0.049 | 0.046 | 0.0443 | 0.0471 | 0.0482 | 0.0451 | 0.0451 | 0.0434 |
| B | 0.0487 | 0.0516 | 0.0433 | 0.0454 | 0.0432 | 0.0473 | 0.0461 | 0.0455 | 0.0462 | 0.048 | 0.0477 | 0.0447 |
| C | 0.0441 | 0.0462 | 0.0479 | 0.0724 | 0.0449 | 0.0545 | 0.0435 | 0.0721 | 0.0441 | 2.9692 | 0.0422 | 0.0431 |
| D | 0.0439 | 0.0579 | 0.1039 | 0.0746 | 0.0458 | 0.0433 | 0.0428 | 0.0478 | 0.0449 | 0.0501 | 0.0429 | 0.0411 |
| E | 0.0422 | 0.0421 | 0.0609 | 0.0588 | 0.0477 | 0.3069 | 0.0445 | 0.0444 | 0.0427 | 0.0438 | 0.0439 | 0.0411 |
| F | 0.0444 | 0.0593 | 0.2979 | 0.0452 | 0.0436 | 0.0444 | 0.087 | 0.1167 | 0.0445 | 0.0415 | 0.05 | 0.0436 |
| G | 0.0478 | 0.0444 | 0.0427 | 0.043 | 0.0437 | 0.0403 | 0.0436 | 0.0464 | 0.0447 | 0.0633 | 0.0438 | 0.0455 |
| H | 0.0451 | 0.0458 | 0.0495 | 0.0455 | 0.0514 | 0.0425 | 0.049 | 0.045 | 0.2415 | 0.0658 | 0.046 | 0.1125 |

Figure 7:
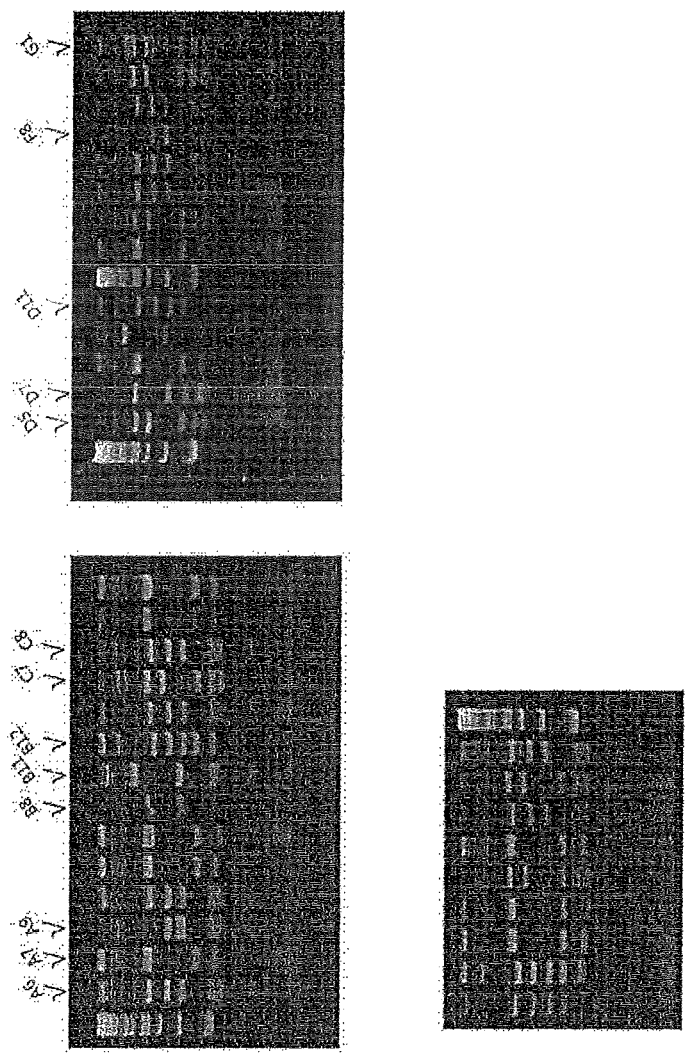
FIG. 7 shows the PCR results of fragments of monoclonal phage antibodies digested by Bst NI.

(3) Classification and Inspection of Monoclonal Phages
A. Verification by Fingerprinting 1 µl of the 36 monoclonal colonies against the primarily screened ACVR2B-Fc, 0.2 µl of Taq DNA polymerase (Gen-Docs Inc., 5 U/µl), 0.2 µl of 50 p/µl forward primer (SEQ ID NO: 2: 5'-CTAGATAACGAGGGCAAATCATG-3') and reverse primer (SEQ ID NO: 3: 5'-CGTCACCAATGAAAC- As a result, it was revealed that the fragments of the monoclonal phage antibodies digested by Bst NI showed the diversities, as shown in FIG. 7, deducing that the 13 different antibodies were screened.

B. Verification by DNA Sequence Analysis

Thirteen types of the monoclonal phages against the water-soluble ACVR2B were cultured at a temperature of 37° C. for 16 hours in a medium (5 ml) supplemented with 2×YTCM, 2% glucose, and 5 mM MgCl$_2$. DNA was obtained from the cultured monoclonal phages using a DNA purification kit (Nuclogen 5112), and sequenced (SolGent, Korea). As a result, the CDR regions of VH and VL of the screened antibodies were identified, as listed in Table 11, and the sequences of heavy chains (SEQ ID NOS: 47 to 47) and light chains (SEQ ID NOS: 58 to 68) of the respective antibodies are listed in the Sequence Listing.

DNA, 10 pmole/µl of forward and reverse primers of the heavy chain listed in Table 12, 5 µl of a 10× buffer, 1 µl of a 10 mM dNTP mix, 0.5 µl of a pfu DNA polymerase (SolGent, 2.5 U/µl), and distilled water, and the resulting mixture was subjected to colony PCR (iCycler iQ, BIO-RAD). The light chain was also subjected to colony PCR in the same manner using the forward and reverse primers of the light chain listed in Table 12.

TABLE 11

Grouping of Mono Phage for ACVR2B

| Clone Name | VH | Identities | CDR3-a.a seq | VL | Identities | CDR3-a.a seq | Group | ACVR2B | a-myc | Fc | Ratio |
|---|---|---|---|---|---|---|---|---|---|---|---|
| ACVR2B A06 | VH3-49 | 277/300 (92.3%) | G-----HYAMDV | O12 | 279/284 (98.2%) | QQSYDTPF | 1 | 2.960 | 0.703 | 0.046 | 4.208 |
| ACVR2B A07 | VH3-9 | 272/292 (93.2%) | DGG-RFYYGLDV | A23 | 287/302 (95.0%) | AETSQVPH | 2 | 2.664 | 0.213 | 0.044 | 12.498 |
| ACVR2B A09 | VH3-7 | 277/294 (94.2%) | G------AWLDY | L14 | 274/284 (96.5%) | LQHKSYPY | 3 | 2.180 | 1.170 | 0.048 | 1.862 |
| ACVR2B B11 | VH3-9 | 271/292 (92.8%) | GSS-SGRYYFDY | L19 | 256/286 (89.5%) | QQAKNFPL | 4 | 2.991 | 0.657 | 0.047 | 4.549 |
| ACVR2B B12 | VH5-51 | 261/293 (89.1%) | G------TALGV | L14 | 275/284 (96.8%) | LQHKSYPY | 5 | 2.755 | 1.456 | 0.044 | 1.891 |
| ACVR2B B08 | VH3-49 | 275/300 (91.7%) | G-----HYGMDV | L5 | 279/284 (98.2%) | QQAKSYPY | 6 | 2.644 | 1.160 | 0.045 | 2.279 |
| ACVR2B C07 | VH3-11 | 280/295 (94.9%) | G-----HYGMDI | L8 | 273/286 (95.5%) | QQVKSYPL | 7 | 2.977 | 0.440 | 0.043 | 6.752 |
| ACVR2B C08 | VH3-64 | 280/291 (96.2%) | TYG-GYGNAFDI | L5 | 276/284 (97.2%) | QQGKSFPY | 8 | 2.867 | 1.170 | 0.072 | 2.449 |
| ACVR2B D11 | VH3-49 | 289/300 (96.3%) | G-----HYGMDV | O12 | 274/284 (96.5%) | QQSYSTPY | 9 | 3.051 | 0.833 | 0.042 | 3.660 |
| ACVR2B D07 | VH1-46 | 295/296 (99.7%) | DQSRGWYSNFDS | L12a | 266/282 (94.3%) | QQYHSYPI | 10 | 2.661 | 0.240 | 0.042 | 11.046 |
| ACVR2B F08 | VH3-72 | 294/300 (98.0%) | G------AWLDY | L14 | 273/285 (95.8%) | LQHKSYPL | 11 | 2.941 | 0.783 | 0.116 | 3.755 |

The homologies between these antibodies and a group of germ line antibodies were examined using a NCBI's Ig BLAST program (www.ncbi.nlm.nih.gov/igblast/). As a result, the 11 phage antibodies specific to the water-soluble ACVR2B were obtained. In this case, each heavy chain included two copies of VH3-9, three copies of VH3-49, and one copy of each of H3-7, VH5-51, VH3-11, VH3-64, VH1-46 and VH3-72. The amino acid sequences for the CDR3 of the heavy and light chains of the antibodies were analyzed, and it was confirmed that the phage antibodies had different sequences (FIGS. 8 and 9).

(4) Characterization of Human Antibodies Against Water-Soluble ACVR2B

A. Analysis of Full-Length IgG Conversion

To convert the monoclonal phage antibodies against the water-soluble ACVR2B into a full-length IgG vector in phages, the heavy chain was mixed with 1 µl of monoclonal

TABLE 12

| Clone name | Forward primer | Reverse Primer | |
|---|---|---|---|
| | | HC | |
| A06 | NATVH1-1 | SEQ ID NO: 7 | NATJH-ALL SEQ ID NO: 8 |
| A07 | NATVH7-1 | SEQ ID NO: 6 | |
| A09 | NATVH3-2 | SEQ ID NO: 5 | |
| B11 | NATVH3-2 | SEQ ID NO: 5 | |
| B12 | NATVH1-1 | SEQ ID NO: 7 | |
| B08 | NATVH1-1 | SEQ ID NO: 7 | |
| C07 | NATVH1-2 | SEQ ID NO: 17 | |

TABLE 12-continued

| Clone name | Forward primer | Reverse Primer | |
|---|---|---|---|
| C08 | NATVH3-2 | SEQ ID NO: 5 | |
| D11 | NATVH1-2 | SEQ ID NO: 17 | |
| D07 | NATVH1-1 | SEQ ID NO: 7 | |
| F08 | NATVH3-2 | SEQ ID NO: 5 | |
| LC | | | |
| A06 | NATVK1-1 | SEQ ID NO: 18 | NATJK-R5 | SEQ ID NO: 14 |
| A07 | NATVK3 | SEQ ID NO: 19 | NATJK-R4 | SEQ ID NO: 16 |
| A09 | NATVK1-1 | SEQ ID NO: 18 | NATJK-R5 | SEQ ID NO: 14 |
| B11 | | | NATJK-R7 | SEQ ID NO: 12 |
| B12 | | | NATJK-R5 | SEQ ID NO: 14 |
| B08 | | | NATJK-R4 | SEQ ID NO: 16 |
| C07 | | | NATJK-R4 | SEQ ID NO: 16 |
| C08 | | | NATJK-R2 | SEQ ID NO: 19 |
| D11 | | | NATJK-R5 | SEQ ID NO: 14 |
| D07 | | | NATJK-R3 | SEQ ID NO: 20 |
| F08 | | | NATJK-R4 | SEQ ID NO: 16 |

A gene coding for the heavy chain obtained by PCR was purified using a DNA-gel extraction kit (Qiagen), mixed with 1 μl (10 ng) of a pNATAB H vector (FIG. 4), 15 μl of the heavy chain (100 to 200 ng), 2 μl of a 10× buffer, a ligase (1 U/μl), and distilled water, and then ligated with the vector while being kept at room temperature for 1 to 2 hours. The vector was kept on ice together with transformant cells (XL1-blue) for 30 minutes, and then transformed by applying heat shock to the cells at 42° C. for 90 seconds. The transformed cells were kept on ice for 5 minutes, and 1 ml of a LB medium was added to the cells, which were then cultured at 37° C. for an hour. Thereafter, the cells were spread on a solid LB Amp medium, and then cultured at 37° C. for 16 hours. Single colonies were seeded in 5 ml of a liquid LB Amp medium, and then cultured at 37° C. for 16 hours. DND was extracted from the culture broth using a DNA-preparative kit (Nuclogen). Also, the light chain was extracted in the same manner using a pNATAB L vector (FIG. 5).

The obtained DNAs were sequenced using a CMV-proF primer (SEQ ID NO: 4: AAA TGG GCG GTA GGC GTG) (SolGent). As a result, it was confirmed that the sequences of the heavy and light chains of the 11 clonal phages against the ACVR2B-Fc converted into the full-length IgG matched the sequences of the phage antibodies (FIGS. 8 and 9).

EXAMPLE 5

Determination of Effects of DLK1 on Differentiation of Myoblast C2C12

An extracellular domain of a DLK1 protein, which was known to play a part in inhibition of adipogenesis at developmental and differentiation stages while systemically circulating in human blood, was expressed and purified in the form of a Fc fusion protein as described in Example 1, and myoblasts were treated with the Fc fusion protein to determine an effect of the water-soluble DLK1 on differentiation of myoblasts.

More particularly, when the myoblasts C2C12 amounted for approximately 90% of the medium, the medium was replaced with a fresh differentiation medium (DM) to replenish 2% horse serum (HS), and divided into six experimental groups. Thereafter, each of the experimental groups was treated with ACVR2B-Fc (0.5 μM), DLK1-Fc (0.5 μM) and/or myostatin (8 μg/ml), as follows. Then, the differentiation stages were observed for 72 hours under a microscope. In this Example, the myostatin was purchased from R&D Systems, and used.

1) DM
2) DM+ACVR2B-Fc (0.5 μM)
3) DM+DLK1-Fc (0.5 μM)
4) DM+myostatin (8 μg/ml)
5) DM+myostatin (8 μg/ml)+ACVR2B-Fc (0.5 μM)
6) DM+myostatin (8 μg/ml)+DLK1-Fc (0.5 μM)

Figure 10:
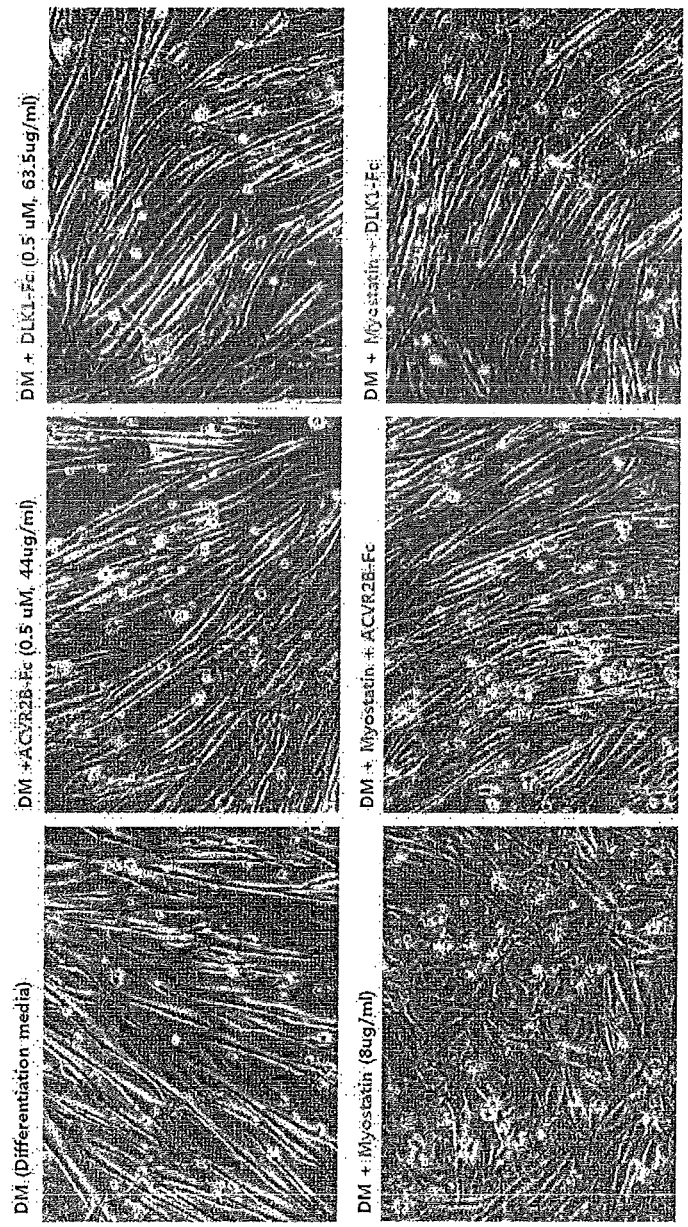
FIG. 10 shows the experimental results showing that DLK1-Fc has an inhibitory effect on myogenesis of myostatin in a myoblast C2C12 cell line.

As a result, it could be seen that the myogenesis was inhibited when the myoblast C2C12 cell line was treated with 8 μg/ml myostatin, as shown in FIG. 10, indicating that the differentiation of muscular cells was promoted by preventing an inhibitory effect of myostatin on myogenesis when the myoblast C2C12 cell line was treated with ACVR2B-Fc or DLK1-Fc.

EXAMPLE 6

Determination of Binding of DLK1 to ACVR2B

To determine whether DLK1 binds to a myostatin receptor, ACVR2B, immunoprecipitation analyses were performed. For this purpose, the myoblast C2C12 cell line was harvested, and sonicated in an RIPA buffer (50 mM TrisHCl, pH7.4, 150 mM NaCl, 2 mM EDTA, and 1% NP-40) to obtain a cell lysate. Then, the cell lysate was precleared at 4° C. for 3 hours using a normal goat serum (Vector Lab. Inc.) and a protein A resin (GE, Sweden). Thereafter, only a protein A resin was added to the resulting reaction mixture, and reacted at 4° C. for 3 hours to remove the remaining antibodies. Then, the reaction mixture was immunoprecipitated overnight at 4° C. using the human ACVR2B antibody F08 prepared in Example 3 and the DLK1 antibody B09 prepared in Example 4.

The human antibody F08 used in this Example was an antibody having a very high binding capacity (Kd=4.05 pM) to ACVR2B, and the human antibody B09 was an antibody which bound to the first and second EGF-like repeats of DLK1 to remarkably increase the binding of DLK1 to ACVR2B.

The immunoprecipitated pellet was washed three times with an RIPA buffer, and re-suspended in 80 μl of an RIPA buffer. Thereafter, 20 μl of a 5× sample buffer was added to the resulting suspension, and reacted at 95° C. for 5 minutes. Subsequently, the resulting reaction mixture was centrifuged to collect a supernatant. Then, the supernatant was subjected to a western blot test. 25 μl of each of the samples was loaded, and 5% by weight of the cell lysate used for immunoprecipitation was loaded and used as the control. Then, the loaded samples were transferred to a nitrocellulose (NC) membrane (Bio-Rad), blocked with 5% skim milk/0.05% TBST Tween 20 for 30 minutes, and then reacted overnight at 4° C. using DLK1 (R&D mAb1144), ACVR2B (R&D AF339), myostatin (Millipore), and α-tubulin (Santa Cruz) antibodies. In this case, the α-tubulin was used as the negative control. Thereafter, the samples were washed three times with 0.05% TBST Tween 20 for 10 minutes, reacted with the corresponding secondary antibody-HRPs (mouse-, goat- and rabbit-IgG-HRPs) at 1:1000 for an hour, and again washed three times with 0.05% TBST Tween 20 for 10 minutes. The color development was analyzed by exposing the samples to a film (Agfa) in an ECL solution (Intron) for one minute. The results are shown in FIG. 11.

Figure 11:
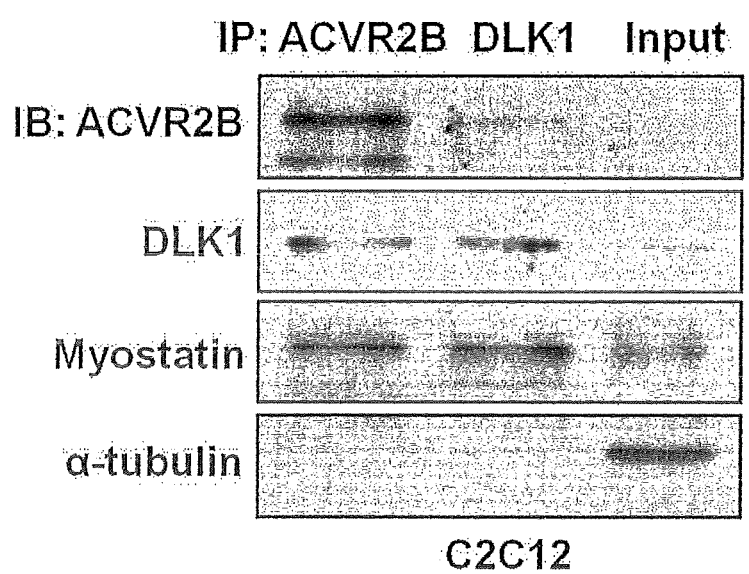
FIG. 11 shows the experimental results of immunoprecipitation analysis performed to determine the binding of myostatin or ACVR2B to DLK1.

As shown in FIG. 11, the immunoprecipitated pellet was western-blotted. As a result, it could be seen that myostatin was bound to DLK1 in the samples precipitated by ACV2B, and that a band in which myostatin was bound to DLK1 was observed in the samples precipitated by DLK1. Accordingly, it was confirmed that the myostatin receptor, ACVR2B, was able to be used as a novel receptor for DLK1, which had not been found as an intracellular receptor so far.

EXAMPLE 7

ELISA Experiment for Analysis of Binding Capacity of DLK1 to Myostatin

An immunoplate was coated overnight with 1 μg/ml of C-terminally active myostatin (R&D systems) at 4° C., washed three times with 0.05% PBST Tween 20, and then blocked with 4% skim milk/0.05% PBST Tween 20 at room temperature for 30 minutes. Thereafter, the immunoplate was washed with 0.05% PBST Tween 20, and a DLK1-Fc protein to be bound to each well was serially diluted starting from a concentration of 1 M, and reacted at room temperature for 2 hours. Then, the immunoplate was washed three times with 0.05% PBST Tween 20, reacted with Fc-HRP (Pierce) at 1:500 at room temperature for an hour, washed three times with 0.05% PBST Tween 20, and then reacted with TMB (Sigma) for 10 minutes in a dark room. Finally, when the reaction was blocked with 2.5 M $H_2SO_4$, the optical densities were measured and analyzed at 420 nm. The results are shown in FIG. 12.

Figure 12:
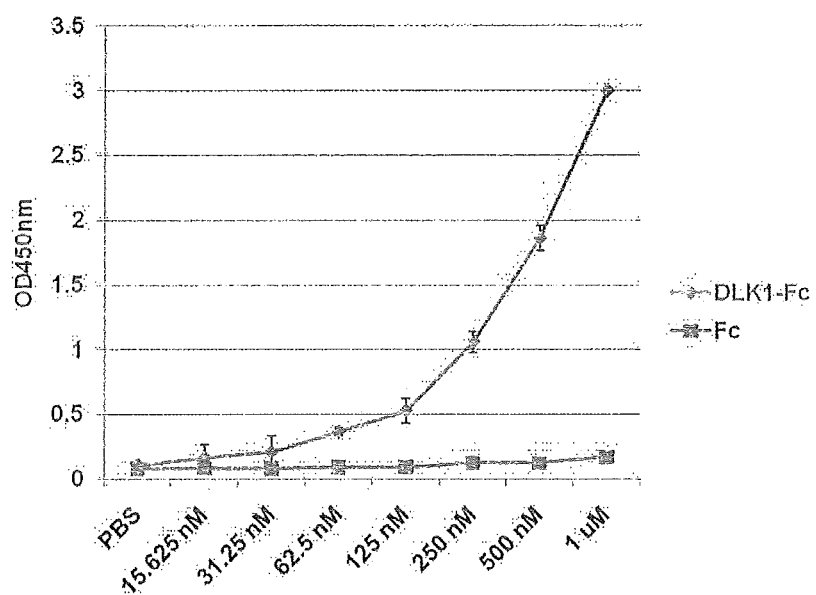
FIG. 12 shows the results of ELISA analysis performed to determine the binding affinity of myostatin to DLK1.

As shown in FIG. 12, it could be seen that the binding of myostatin increased according to the concentration of DLK1-Fc, and that myostatin specifically bound to DLK1 regardless of Fc since Fc used as the negative control did not bind to myostatin.

EXAMPLE 8

Experiment of Comparison of Binding Capacities of Myostatin and ACVR2B or DLK1

Figure 13:
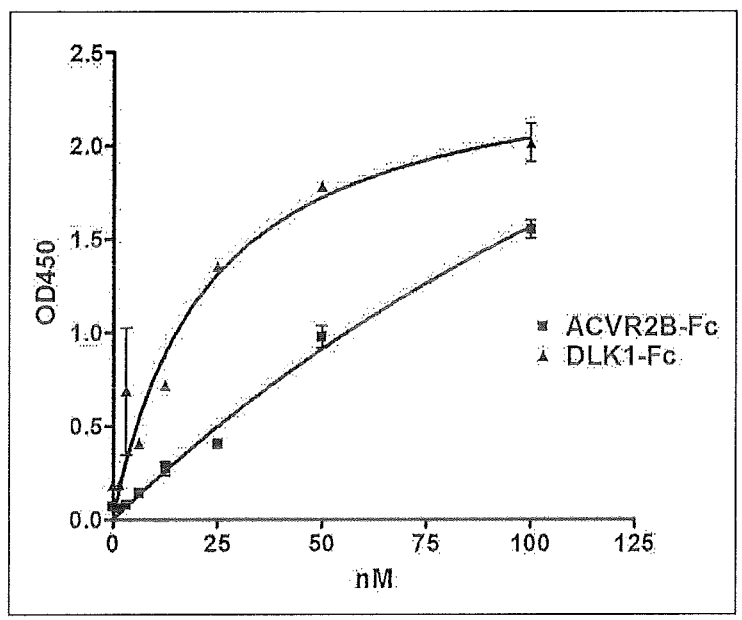
FIG. 13 shows the results of ELISA analysis performed to determine the binding affinity of DLK1 or ACVR2B to myostatin.

An immunoplate was coated overnight with 1 μg/ml of C-terminally active myostatin (R&D systems) at 4° C. in the same manner as in Example 7. Then, ACVR2B-Fc and DLK1-Fc were serially diluted starting from a concentration of 100 nM, and reacted at room temperature for 2 hours to determine the binding affinities. The results are shown in FIG. 13. As shown in FIG. 13, it could be seen that DLK1 showed higher binding affinity to myostatin than ACVR2B.

Based on the experiment, a KD value was also determined by analyzing one site binding (hyperbola) using a GraphPad Reism 4 program. The results are shown in FIG. 14. As shown in FIG. 14, it could be seen that the KD value for myostatin was 256.2 nM±4.897 in the case of ACVR2B, and 22.77 nM±3.665 in the case of DLK1, indicating that DLK1 had a higher binding affinity to myostatin than ACVR2B.

From these results, it was expected that DLK1 was more effective than water-soluble ACVR2B-Fc as an inhibitor for the conventional mechanism in which myogenesis was inhibited by binding of ACVR2B to myostatin.

EXAMPLE 9

Competitive ELISA Analysis

To determine whether the water-soluble DLK1 and myostatin competitively bound to the ACVR2B receptor, a competitive ELISA was performed. An immunoplate was coated overnight with 1 μg/ml of C-terminally active myostatin (R&D systems) at 4° C., and ACVR2B-Fc and FLAG-DLK1 were reacted together, and measured. In this case, ACVR2B was treated at a fixed concentration of 1 nM, and FLAG-DLK1 was treated at different concentrations of 1 nM to 1 μM to measure a competitive binding degree.

ACVR1A-Fc which was not bound to myostatin was used as the control, and Fc-HRP was used as the secondary antibody in the case of the control to which only 1 μM FLAG-DLK1 was bound. In this case, the control was used to determine whether the binding of pure myostatin to ACVR2B was inhibited by DLK1 since a signal occurring by the binding was not measured.

Figure 15:
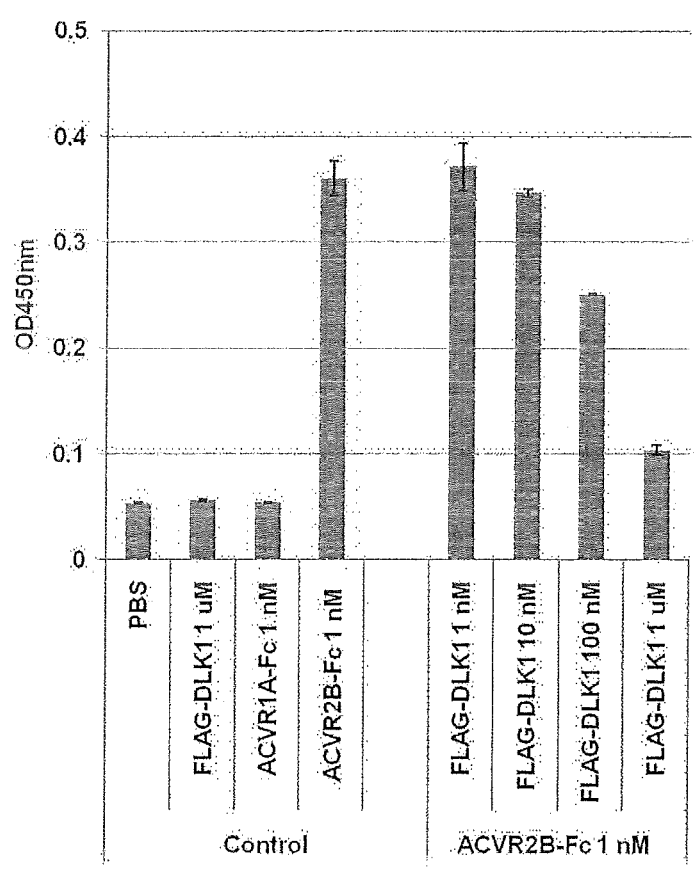
FIG. 15 shows the results of competitive ELISA analysis performed to measures binding affinities of DLK1 and ACVR2B to myostatin.

The measurement results using the competitive ELISA are shown in FIG. 15. As shown in FIG. 15, it was revealed that myostatin was readily bound to ACVR2B-Fc. In this case, it could be seen that the binding of myostatin to ACVR2B was prevented when myostatin was reacted with an increasing concentration of FLAG-tagged DLK1 together with ACVR2B.

EXAMPLE 10

Construction of DLK1-Fc Deletion Mutants

Figure 16:
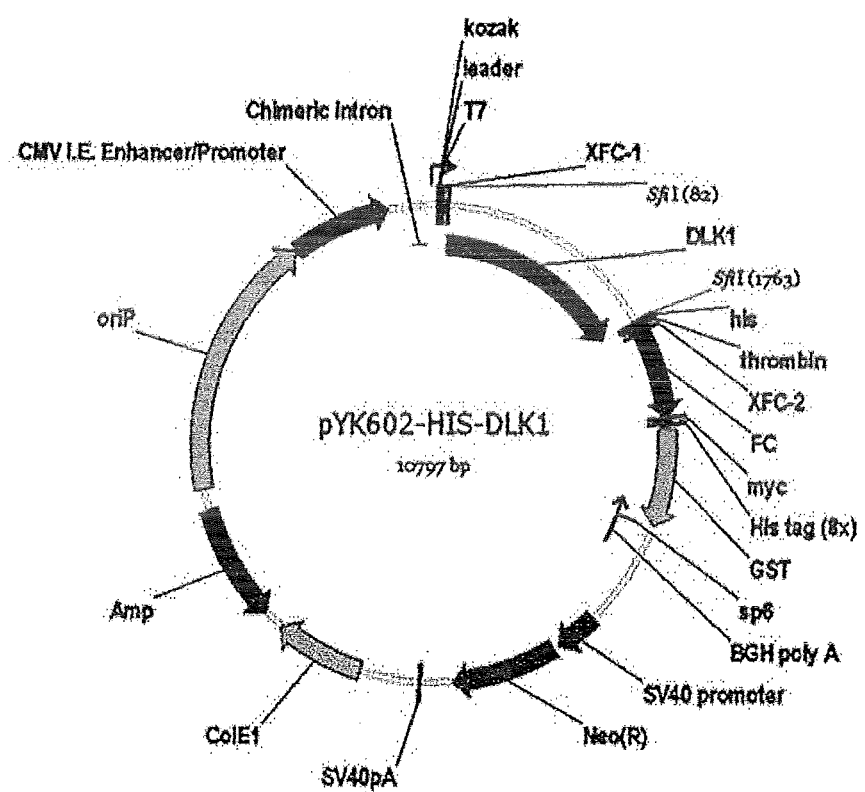
FIG. 16 shows a pYK602-DLK1-Fc construct.
Figure 17:
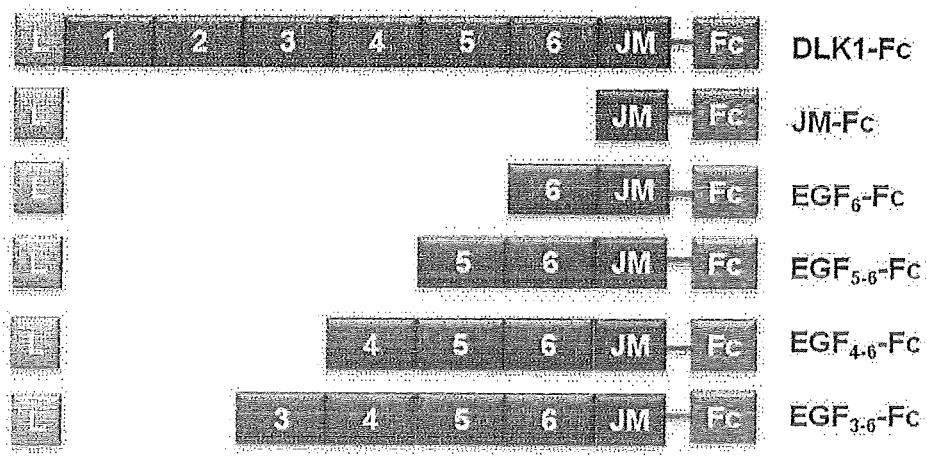
FIG. 17 is a schematic diagram showing structures of EGF-like repeat deletion mutants of DLK1.

To determine the binding sites of DLK1 and ACVR2B, EGF-like repeat deletion mutants of DLK1 were constructed. More particularly, deletion mutants were constructed by sequentially deleting the EGF-like repeat domains using a pYK602-DLK1-Fc construct (FIG. 16) as a template. Then, the constructs of the obtained deletion mutants are shown in FIG. 17, and their amino acid sequences are set forth in SEQ ID NOS: 28 to 34, respectively, (Table 14). In this Example, sets of primers used for PCR to construct the deletion mutants are listed in the following Table 13.

TABLE 13

| Sequence name | DNA sequence | SEQ ID NO |
|---|---|---|
| Reverse primer D-R | gctagcggccgacgcggccaagccctcggtgaggagagg | SEQ ID NO: 22 |
| Forward primer 3M-Fc | aaaaaaggccgtgggggccgatgttcgggcctgctcctc | SEQ ID NO: 23 |
| Forward primer 4M-Fc | aaaaaaggccgtgggggccaaggacgggccctgtgtgatc | SEQ ID NO: 24 |
| Forward primer 5M-Fc | aaaaaaggccgtgggggccgtggccaacagctgcacccc | SEQ ID NO: 25 |
| Forward primer 6M-Fc | aaaaaaggccgtgggggccccggtgaccaactgcgccag | SEQ ID NO: 26 |
| Forward primer JM-Fc | aaaaaaggccgtgggggccaagaagcgcgcgctgagccc | SEQ ID NO: 27 |

TABLE 14

| Sequence name | DNA/amino acid sequence | SEQ ID NO |
|---|---|---|
| Water-soluble DLK1 DNA sequence | atgaccgcgaccgaagccctcctgcgcgtcctcttgctcctgctggctttcgg<br>ccacagcacctatgggctgaatgcttcccggcctgcaaccccaaaatggat<br>tctgcgaggatgacaatgtttgcaggtgccagcctggctggcagggtcccctt<br>tgtgaccagtgcgtgacctctcccggctgccttcacggactctgtggagaacc<br>cgggcagtgcatttgcaccgacggctgggacggggagctctgtgatagagatg<br>ttcgggcctgctcctcggcccctgtgccaacaacgggacctgcgtgagcctg<br>gacgatggcctctatgaatgctcctgtgcccccgggtactcgggaaaggactg<br>ccagaaaaaggacgggcctgtgtgatcaacggctcccctgccagcacggag<br>gcacctgcgtggatgatgagggccgggcctcccatgcctcctgcctgtgcccc<br>cctggcttctcaggcaatttctgcgagatcgtggccaacagctgcacccccaa<br>cccatgcgagaacgacggcgtctgcactgacattgggggcgacttccgctgcc<br>ggtgcccagccggcttcatcgacaagacctgcagccgcccggtgaccaactgc<br>gccagcagcccgtgccagaacgggggcacctgcctgcagcacacccaggtgag<br>ctacgagtgtctgtgcaagcccgagttcacaggtctcacctgtgtcaagaagc<br>gcgcgctgagccccagcaggtcacccgtctgcccagcgcgctatgggctggcc<br>taccgcctgaccctggggtgcacgagctgccggtgcagcagccggagcaccg<br>catcctgaaggtgtccatgaaagagctcaacaagaaaacccctctcctcaccg<br>agggc | SEQ ID NO: 28 |
| Water-soluble DLK1 amino acid sequence | MTATEALLRVLLLLLAFGHSTYGAECFPACNPQNGFCEDDNVCRCQPGWQGPL<br>CDQCVTSPGCLHGLCGEPGQCICTDGWDGELCDRDVRACSSAPCANNGTCVSL<br>DDGLYECSCAPGYSGKDCQKKDGPCVINGSPCQHGGTCVDDEGRASHASCLCP<br>PGFSGNFCEIVANSCTPNPCENDGVCTDIGGDFRCRCPAGFIDKTCSRPVTNC<br>ASSPCQNGGTCLQHTQVSYECLCKPEFTGLTCVKKRALSPQQVTRLPSGYGLA<br>YRLTPGVHELPVQQPEHRILKVSMKELNKKTPLLTEG | SEQ ID NO: 29 |
| EGF3-6 amino acid sequence | DVRACSSAPCANNGTCVSLDDGLYECSCAPGYSGKDCQKKDGPCVINGSPCQH<br>GGTCVDDEGRASHASCLCPPGFSGNFCEIVANSCTPNPCENDGVCTDIGGDFR<br>CRCPAGFIDKTCSRPVTNCASSPCQNGGTCLQHTQVSYECLCKPEFTGLTCVK<br>KRALSPQQVTRLPSGYGLAYRLTPGVHELPVQQPEHRILKVSMKELNKKTPLL<br>TEG | SEQ ID NO: 30 |
| EGF4-6 amino acid sequence | KDGPCVINGSPCQHGGTCVDDEGRASHASCLCPPGFSGNFCEIVANSCTPNPC<br>ENDGVCTDIGGDFRCRCPAGFIDKTCSRPVTNCASSPCQNGGTCLQHTQVSYE<br>CLCKPEFTGLTCVKKRALSPQQVTRLPSGYGLAYRLTPGVHELPVQQPEHRIL<br>KVSMKELNKKTPLLTEG | SEQ ID NO: 31 |
| EGF5-6 amino acid sequence | VANSCTPNPCENDGVCTDIGGDFRCRCPAGFIDKTCSRPVTNCASSPCQNGGT<br>CLQHTQVSYECLCKPEFTGLTCVKKRALSPQQVTRLPSGYGLAYRLTPGVHEL<br>PVQQPEHRILKVSMKELNKKTPLLTEG | SEQ ID NO: 32 |
| EGF6 amino acid sequence | PVTNCASSPCQNGGTCLQHTQVSYECLCKPEFTGLTCVKKRALSPQQVTRLPS<br>GYGLAYRLTPGVHELPVQQPEHRILKVSMKELNKKTPLLTEG | SEQ ID NO: 33 |
| Juxtamembrane region (JM) amino acid sequence | KKRALSPQQVTRLPSGYGLAYRLTPGVHELPVQQPEHRILKVSMKELNKKTPL<br>LTEG | SEQ ID NO: 34 |

A PCR mix was prepared using 10 µl of a 10× buffer, 10 µl of dNTP mixes, 1 unit of pfu (Stratagene), 5 µl of a forward primer, 5 µl of an reverse primer, a template pYK602-DLK1-Fc, and 68 µl of sterile deionized water, and the PCR conditions were as follows: one cycle of denaturing at 94° C. for 30 seconds, 30 cycles of amplification at 94° C. for 30 seconds and 68° C. for one minute, and one cycle of additional extension at 72° C. for 5 minutes. PCR products were washed using a PCR clean up kit (Qiagen), and then digested with a restriction enzyme SfiI (NEB) at 50° C. for 2 hours. The digested DNA fragments were purely purified using a gel elution kit (Qiagen). A ligation reaction was performed using the prepared insert and vector. In this case, the composition for the ligation reaction included 1 µl of a 10× ligase buffer, 1 µl of pYK602-Fc vector/SfiI, 3 µl of an insert PCR product/SfiI, 1 µl of a ligase (Roche), and 4 µl of sterile deionized water. The ligation composition was reacted overnight at 4° C. to ligate the insert into the vector, and DH5α competent cells was transformed with the vector. Thereafter, the transformed cells were spread on an LB/ampicillin plate, and cultured at 37° C. in an incubator. The next day, the growing colonies were picked into 5 ml of an LB/ampicillin medium, and cultured for 18 hours. Then, plasmids were separated using a plasmid mini-preparative kit (NucleoGen), and the separated plasmids were sequenced.

EXAMPLE 11

Expression of DLK1-Fc and Deletion Mutants

Figure 18:
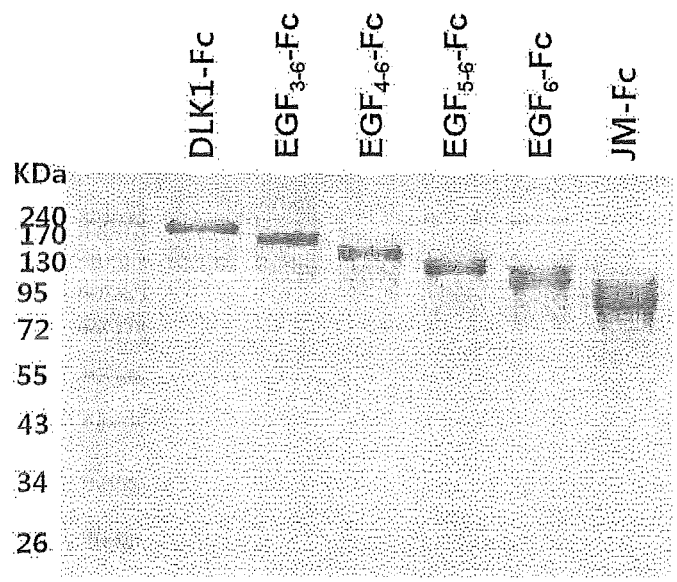
FIG. 18 shows the results obtained by determining expression of DLK1-Fc and respective deletion mutant proteins using an SDS-PAGE assay.

To express the cloned DLK1-Fc and deletion mutants, 293E cells were used. More particularly, 10 µg of DNA and 20 µg of PEI (#23966, Polysciences, USA) were mixed at a cell level in 70% of a 100 mm plate, and reacted at room temperature for 20 minutes to prepare a fusion. Then, the cells were treated with fusion. After 16 to 10 hours, the medium used was replaced with a serum-free DMEM medium, and recovered every other day while the medium used was replaced with a fresh medium. The cells which were likely to remain in the medium were completely removed through centrifugation, and sifted through a 0.22 µm filter (#PR02890 Millipore, USA). Subsequently, the cells were purified through a Protein A column. The 10 ml column was filled with 500 µl of Protein A beads (#17-1279-03 GE, Sweden), and washed with PBS, and the medium in which DLK1-Fc was expressed was allowed to flow through the column. A peristaltic pump was used in this procedure, and set so that an eluent flowed at a rate of 0.5 ml per minute. Then, after the medium was allowed to flow completely through the column, the column was washed with PBS, and the purified DLK1-Fc protein was recovered in 0.1 M glycine-HCl (pH 3.5; (#G7126, Sigma, USA). The pH of the recovered protein was neutralized using IM Tris (pH 9.0; #T-1503, Sigma, USA), and then dialyzed through PBS. The purified protein was quantified through BCA analysis, and subjected to SDS-PAGE to determine whether the protein was purified (FIG. 18). In this procedure, the purified DLK1-Fc and the DLK1 deletion mutant protein were obtained.

EXAMPLE 12

Surface Plasmon Resonance Spectroscopy (SPR) Analysis

To determine the binding sites of the DLK1-Fc and DLK1 deletion mutant proteins prepared and purified in Example 11 to ACVR2B, SPR analyses were performed. This experiment was performed using a ProteOn XPR36 instrument (Bio-Rad). First, a sensor chip (GLC) was activated by reacting 0.1 M EDC and 0.025 M sulfo-NHS (Bio-Rad) for 60 seconds. Then, the chip was coated with ACVR2B-Fc by allowing the ACVR2B-Fc mixed with 10 mM sodium acetate (pH 5.0) to flow at a rate of 30 μl/min for 240 seconds. One channel was coated with a solution obtained by mixing Fc with 10 mM sodium acetate (pH 4.5) for use as a reference. The coating procedure was completed by allowing 1 M ethanolamine-HCl) (pH 8.5) to flow at the coated chip for 200 seconds. To test the bound proteins, the chip was rotated at an angle of 90°, and stabilized by allowing DPBST (PBS with 0.005% Tween 20) to flow on the chip for 30 minutes. Then, DLK-Fc or each of the purified deletion mutant proteins to be reacted was allowed to flow at a rate of 30 μl/min for 120 seconds to determine an association constant, and DPBST (PBS with 0.005% Tween 20) was allowed to flow for 240 seconds to determine a dissociation constant.

Figure 19:
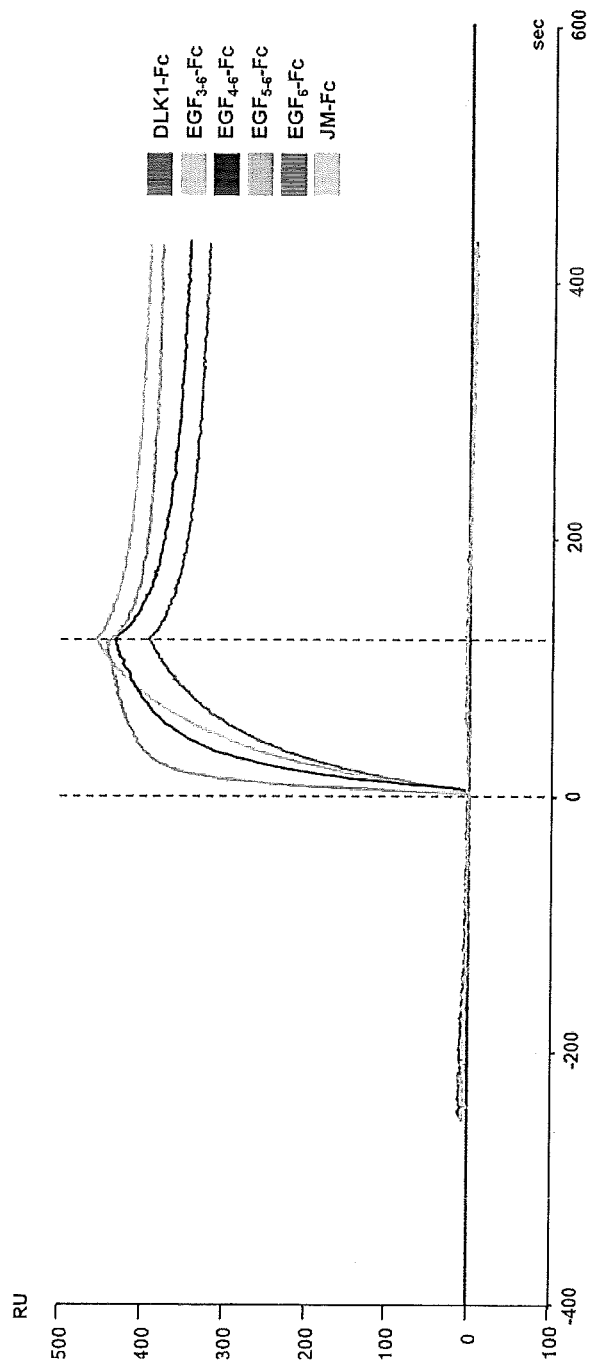
FIG. 19 shows the results obtained by performing SPR experiments to determine a binding site of DLK1 to ACVR2B.

The results are listed in the following Table 15 and shown in FIG. 19. The binding capacities of ACVR2B to the respective samples were measured. From the fact that DLK1 and ACVR2B were bound to $EGF_{5-6}$-Fc, it could be seen that ACVR2B was bound to the fifth EGF-like repeat domain of DLK1 (Kd=1.3 nM), and that the binding capacities of DLK1 and ACVR2B increased when the first and second repeat domains were deleted.

TABLE 15

| | ka ($M^{-1}s^{-1}$) | kd ($s^{-1}$) | Kd (M) | $Chi^2$ |
|---|---|---|---|---|
| B09 to DLK1-Fc | 3.41E+6 | 6.49E−5 | 1.09E−11 | 2.98 |
| F08 to ACVR2B | 3.25E+6 | 1.32E−5 | 4.05E−12 | 5.58 |
| DLK1-Fc to ACVR2B | 3.31E+5 | 4.34E−5 | 1.31E−9 | 5.26 |
| DLK1-Fc to ACVR2B In the presence of B09 | 6.26E+5 | 2.55E−4 | 4.07E−10 | 8.74 | ka: association rate constant;
kd: dissodation rate constant;
Kd: equilibrium dissodation constant;
$Chi^2$: a statistical measure of how closely the model fits the experimental data

EXAMPLE 13

Experiments of Measurement of Binding Sites Using DLK1 Deletion Mutants

The binding sites of DLK1 and myostatin were determined using the DLK1 deletion mutants. An immunoplate was coated overnight with 1 μg/ml of C-terminally active myostatin (R&D systems) at 4° C., and 10 nM DLK1-Fc or each of the DLK1 deletion mutants was bound to myostatin at room temperature for 2 hours. Fc and ACVR2A-Fc which were not bound to myostatin were used as the negative controls. The immunoplate was washed three times with PBST, reacted with anti-human Fc HRP (1:1000, Pierce) at room temperature for an hour, and colorimetrically developed using a TMB solution (Sigma). Then, when the reaction was completed using a 2.5M $H_2SO_4$ solution, the binding affinities of the DLK1-Fc and DLK1 deletion mutants to myostatin were measured at an optical density of 450 nm. The results are shown in FIG. 20.

Figure 20:
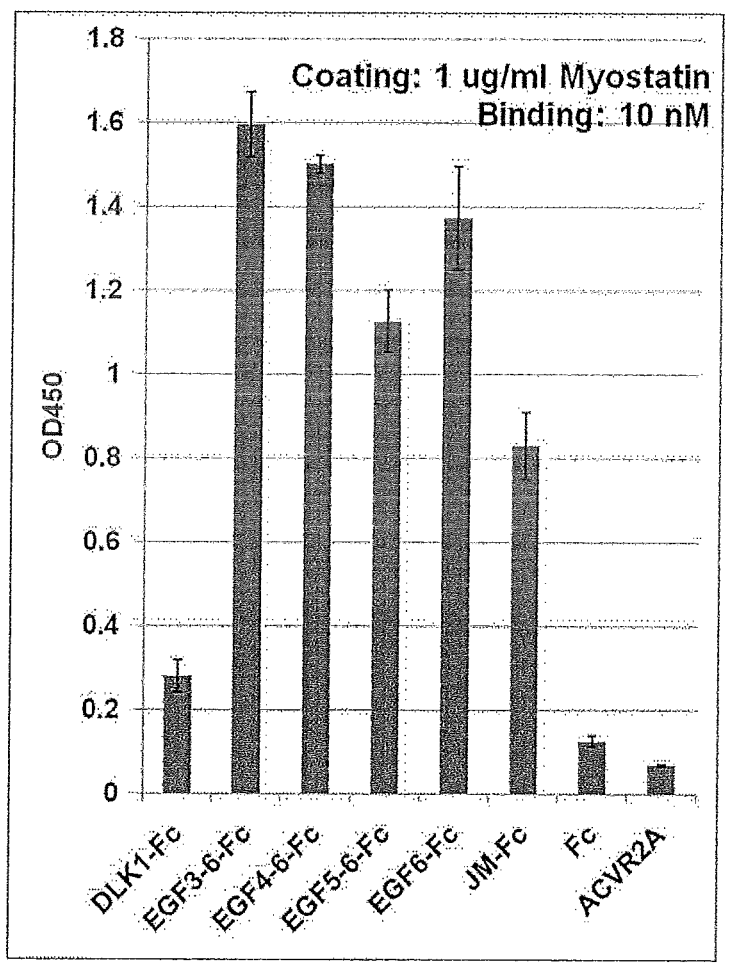
FIG. 20 shows the experimental results obtained by determining binding sites of DLK1 and myostatin using DLK1 deletion mutants.

As shown in FIG. 20, it could be seen that myostatin bound to DLK1 from the JM region of DLK1, and that the first and second EGF-like repeat domains of DLK1 rather inhibited the binding to myostatin.

EXAMPLE 14

Determination of Effect of DLK1 on Smad Signaling

It was well known that myostatin had a mechanism of inhibiting myogenesis by increasing an expression level of pSmad2/3 and reducing an expression of MyoD when myostatin bound to ACVR2B to activate Smad signaling. Accordingly, it was confirmed through CAGA reporter analyses whether the Smad signaling was able to be inhibited when myostatin was treated with DLK1.

Cells were transfected with pTAL-SBE-SEAP (CAGA) containing a Smad binding element (SBE) using Lipofectamine™ 2000 (Invitrogen). Next day, the cells were transferred to a 96-well plate, and cultured in a FBS-free medium for 16 hours (serum starvation). Before activated with myostatin, the cells were treated with DLK1 at serial dilutions from 10 μg/ml, pre-treated with B09 antibody serving to increase the binding of DLK1 to ACVR2B, DLK1 antibody mAb1144 (R&D), and antibodies for ACVR2B, AF339 and F08, for 2 hours, and then treated with 1 nM myostatin to activate the Smad signaling. After 36 hours, the reporter analyses on the culture broth were performed using an SEAP assay kit (Applied Biosystems). The results are shown in FIG. 21.

Figure 21:
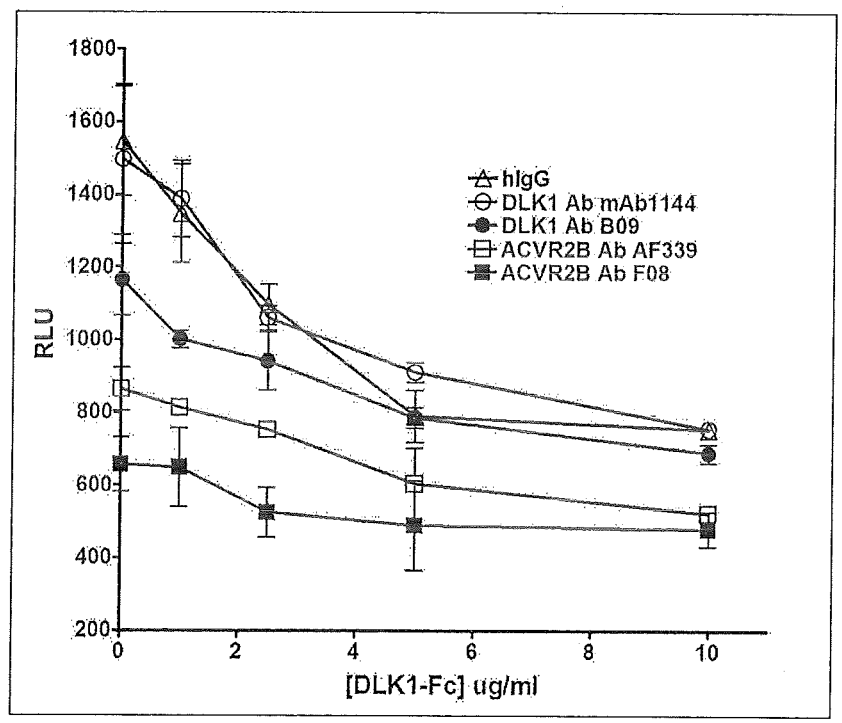
FIG. 21 shows the analytic results using a CAGA (pTAL-SBE-SEAP) reporter to determine an inhibitory effect of DLK1 on myostatin.

As shown in FIG. 21, it could be seen that the Smad signaling by myostatin decreased as the cells were treated with an increasing concentration of DLK1 in the case of the IgG-treated group in which human IgG was used as the negative control for antibodies. In the case of the co-treated group in which the cells were co-treated with human IgG and B09 antibodies, it could be seen that a higher inhibitory effect was expressed by promoting the binding of ACVR2B to DLK1, compared to the single DLK1-treated group. On the other hand, it could be seen that the ACVR2B antibodies (Ab AF339 and F08) also showed the very high binding capacity to ACVR2B, and thus effectively inhibited the Smad signaling by myostatin, but an inhibitory effect by DLK1 rather decreased.

EXAMPLE 15

Determination of Increase in Smad7 by DLK1

Cells were cultured for 24 hours in a 60 mm petri dish until the cells converged to approximately 70% of the dish surface. The medium used was replaced with a fresh serum-free medium, and the cells were cultured for 16 hours. Before the harvest, the cells were treated with 10 μg/ml DLK1-Fc, reacted for 2 hours, and washed twice with cold DPBS (Welgene). Thereafter, the cells were sonicated in an RIPA buffer to yield a cell lysate. The concentration of the cell lysate was determined through quantification using a BCA assay kit (Thermo.), and the cell lysate was loaded on SDS-PAGE at a volume of 30 μg. The samples were transferred to a NC membrane (Bio-Rad), blocked with 5% skim milk/0.05% TBST Tween 20 for 30 minutes, and then reacted overnight with Smad7 (Cell signaling) and β-actin (Sigma) antibodies at 4° C. Thereafter, the samples were washed three times with 0.05% TBST Tween 20 for 10 minutes, reacted with the corresponding secondary antibody-HRPs (rabbit-, and mouse-IgG-HRPs) at 1:1000 for an hour, and again washed three times with 0.05% TBST Tween 20 for 10 minutes. The color development was analyzed by exposing the samples to a film (Agfa) in an ECL solution (Intron) for one minute. The results are shown in FIG. 22.

Figure 22:
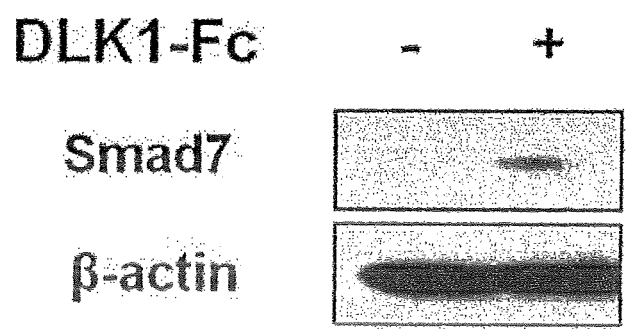
FIG. 22 shows the western blot results obtained by determining an increase in expression of Smad7 by DLK1.

As shown in FIG. 22, it could be seen that DLK1 increased Smad7 inhibiting the Smad signaling. From these facts, it was confirmed that DLK1 was a very effective inhibitor which inhibited the Smad signaling through Smad7 as well as simply reducing an expression level of pSmad2/3 to inhibit the Smad signaling.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

INDUSTRIAL APPLICABILITY

The composition including an extracellular water-soluble domain of DLK1 as an active ingredient according to one exemplary embodiment of the present invention can inhibit an action mechanism of myostatin, thereby enabling development of drugs for preventing or treating metabolic diseases such as diabetes or muscle wasting disease such as muscular dysplasia. Also, the extracellular water-soluble domain of DLK1 can be modified into various forms including fragments or mutants of the extracellular water-soluble domain of DLK1, or fusion proteins in which a human antibody Fc region is bound to the fragments or mutants thereof, and thereby enabling development of prophylactic or therapeutic drugs.

The invention claimed is:

1. A method for treating a myostatin-related disease, comprising administering to a subject having a myostatin-related disease, an extracellular water-soluble domain of a delta-like 1 homolog (DLK1) comprising the sequence of SEQ ID NO: 34, a fragment of the extracellular water-soluble domain of DLK1, wherein the fragment comprises the sequence of SEQ ID NO: 34, a mutant of the extracellular water-soluble domain of DLK1, wherein the mutant comprises the sequence of SEQ ID NO: 34, or a fragment of the mutant, wherein the fragment comprises the sequence of SEQ ID NO: 34, as an active ingredient.

2. The method of claim 1, wherein the extracellular water-soluble domain of DLK1 consists of an amino acid sequence beginning at, and including, residue 25, and ending at, and including, residue 302 of the amino acid sequence set forth in SEQ ID NO: 29.

3. The method of claim 1, wherein the mutant of the extracellular water-soluble domain of DLK1 is a deletion mutant of the extracellular water-soluble domain of DLK1.

4. The method of claim 3, wherein the deletion mutant of the extracellular water-soluble domain of DLK1 is a deletion mutant including an epidermal growth factor-like repeat (EGF-like repeat) sequence.

5. The method of claim 3, wherein the deletion mutant of the extracellular water-soluble domain of DLK1 has one of the amino acid sequences set forth in SEQ ID NO: 30 to SEQ ID NO: 34.

6. The method of claim 1, wherein the extracellular water-soluble domain of DLK1, the fragment of the extracellular water-soluble domain of DLK1, the mutant of the extracellular water-soluble domain of DLK1, or the fragment of the mutant binds to a myostatin or activin receptor type IIB (ACVR2B) to inhibit the action of myostatin.

7. The method of claim 1, wherein the extracellular water-soluble domain of DLK1 or a fragment thereof is conjugated to a human antibody Fc region.

8. The method of claim 1, wherein, the myostatin-related disease is a at least one selected from the group consisting of a muscle wasting disease, a metabolic disease, a degenerative bone disease, hypogonadism, and cachexia.

9. The method of claim 8, wherein the muscle wasting disease is at least one selected from the group consisting of muscular dystrophy, a rigid spine syndrome, a muscle-eye-brain disease, amyotrophic lateral sclerosis (Lou Gehrig's disease), a Charcot-Marie-Tooth disease, chronic inflammatory neuropathy, and distal myopathy.

10. The method of claim 8, wherein the metabolic disease is at least one selected from the group consisting of type 2 diabetes, noninsulin-dependent diabetes mellitus, hyperglycemia, obesity, and diabetic complications.

11. The method of claim 8, wherein the degenerative bone disease is osteoporosis.

* * * * *

SEQUENCE LISTING

```
<160> NUMBER OF SEQ ID NOS: 68

<210> SEQ ID NO 1
<211> LENGTH: 119
<212> TYPE: PRT
<213> ORGANISM: Artificial Sequence
<220> FEATURE:
<223> OTHER INFORMATION: Extracellular domain of ACVR2B

<400> SEQUENCE: 1

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Leu Leu Thr
        115

<210> SEQ ID NO 2
<211> LENGTH: 23
<212> TYPE: DNA
<213> ORGANISM: Artificial Sequence
<220> FEATURE:
<223> OTHER INFORMATION: forward primer

<400> SEQUENCE: 2
ctagataacg agggcaaatc atg                                          23
```

<210> SEQ ID NO 3
<211> LENGTH: 19
<212> TYPE: DNA
<213> ORGANISM: Artificial Sequence
<220> FEATURE:
<223> OTHER INFORMATION: reverse primer

<400> SEQUENCE: 3
cgtcaccaat gaaaccatc                                                19

<210> SEQ ID NO 4
<211> LENGTH: 18
<212> TYPE: DNA
<213> ORGANISM: Artificial Sequence
<220> FEATURE:
<223> OTHER INFORMATION: CMV-proF primer

<400> SEQUENCE: 4
aaatgggcgg taggcgtg                                                 18

<210> SEQ ID NO 5
<211> LENGTH: 50
<212> TYPE: DNA
<213> ORGANISM: Artificial Sequence
<220> FEATURE:
<223> OTHER INFORMATION: NATVH3-2

<400> SEQUENCE: 5
ttggtggcca cagcggccga tgtccactcg caggtgcagc tggtggagtc              50

<210> SEQ ID NO 6
<211> LENGTH: 50
<212> TYPE: DNA
<213> ORGANISM: Artificial Sequence
<220> FEATURE:
<223> OTHER INFORMATION: NATVH7-1

<400> SEQUENCE: 6
ttggtggcca cagcggccga tgtccactcg cagatgcagc tggtggagtc              50

<210> SEQ ID NO 7
<211> LENGTH: 50
<212> TYPE: DNA
<213> ORGANISM: Artificial Sequence
<220> FEATURE:
<223> OTHER INFORMATION: NATVH1-1

<400> SEQUENCE: 7
ttggtggcca cagcggccga tgtccactcg caggtgcagc tggtgcagtc              50

<210> SEQ ID NO 8
<211> LENGTH: 26
<212> TYPE: DNA
<213> ORGANISM: Artificial Sequence
<220> FEATURE:
<223> OTHER INFORMATION: NATJH-ALL

<400> SEQUENCE: 8
gaggaggcta gctgaggaga cggtga                                        26

<210> SEQ ID NO 9
<211> LENGTH: 53
<212> TYPE: DNA
<213> ORGANISM: Artificial Sequence
<220> FEATURE:
<223> OTHER INFORMATION: NATVK6

-continued

<400> SEQUENCE: 9
ttggtggcca cagcggccga tgtccactcg gacatccaga tgacccagtc tcc        53

<210> SEQ ID NO 10
<211> LENGTH: 50
<212> TYPE: DNA
<213> ORGANISM: Artificial Sequence
<220> FEATURE:
<223> OTHER INFORMATION: NATVL13

<400> SEQUENCE: 10
ttggtggcca cagcggccga tgtccactcg cagttcgtgc tgactcagcc             50

<210> SEQ ID NO 11
<211> LENGTH: 50
<212> TYPE: DNA
<213> ORGANISM: Artificial Sequence
<220> FEATURE:
<223> OTHER INFORMATION: NATJK-R7

<400> SEQUENCE: 11
ttggtggcca cagcggccga tgtccactcg cagctcgtgc tgactcagcc             50

<210> SEQ ID NO 12
<211> LENGTH: 30
<212> TYPE: DNA
<213> ORGANISM: Artificial Sequence
<220> FEATURE:
<223> OTHER INFORMATION: NATJK-R7

<400> SEQUENCE: 12
gaggagagat cttttgatat ccaccttggt                                   30

<210> SEQ ID NO 13
<211> LENGTH: 33
<212> TYPE: DNA
<213> ORGANISM: Artificial Sequence
<220> FEATURE:
<223> OTHER INFORMATION: NATJL2-R

<400> SEQUENCE: 13
gaggagagat cttaggacgg tcagcttggt ccc                               33

<210> SEQ ID NO 14
<211> LENGTH: 30
<212> TYPE: DNA
<213> ORGANISM: Artificial Sequence
<220> FEATURE:
<223> OTHER INFORMATION: NATJK-R5

<400> SEQUENCE: 14
gaggagagat cttttgattt ccagcttggt                                   30

<210> SEQ ID NO 15
<211> LENGTH: 33
<212> TYPE: DNA
<213> ORGANISM: Artificial Sequence
<220> FEATURE:
<223> OTHER INFORMATION: NATJL1-R

<400> SEQUENCE: 15
gaggagagat cttaggacgg tgaccttggt ccc                               33

<210> SEQ ID NO 16
<211> LENGTH: 30

<212> TYPE: DNA
<213> ORGANISM: Artificial Sequence
<220> FEATURE:
<223> OTHER INFORMATION: NATJK-R4

<400> SEQUENCE: 16
gaggagagat cttttgattt ccaccttggt         30

<210> SEQ ID NO 17
<211> LENGTH: 50
<212> TYPE: DNA
<213> ORGANISM: Artificial Sequence
<220> FEATURE:
<223> OTHER INFORMATION: NATVH1-2

<400> SEQUENCE: 17
ttggtggcca gcgggccga tgtccactcg cagatgcagc tggtgcagtc         50

<210> SEQ ID NO 18
<211> LENGTH: 50
<212> TYPE: DNA
<213> ORGANISM: Artificial Sequence
<220> FEATURE:
<223> OTHER INFORMATION: NATVK1-1

<400> SEQUENCE: 18
ttggtggcca gcgggccga tgtccactcg gacatccaga tgacccagtc         50

<210> SEQ ID NO 19
<211> LENGTH: 53
<212> TYPE: DNA
<213> ORGANISM: Artificial Sequence
<220> FEATURE:
<223> OTHER INFORMATION: NATVK3

<400> SEQUENCE: 19
ttggtggcca gcgggccga tgtccactcg gatattgtga tgacccagac tcc         53

<210> SEQ ID NO 20
<211> LENGTH: 30
<212> TYPE: DNA
<213> ORGANISM: Artificial Sequence
<220> FEATURE:
<223> OTHER INFORMATION: NATJK-R2

<400> SEQUENCE: 20
gaggagagat cttttgatct ccactttggt         30

<210> SEQ ID NO 21
<211> LENGTH: 30
<212> TYPE: DNA
<213> ORGANISM: Artificial Sequence
<220> FEATURE:
<223> OTHER INFORMATION: NATJK-R3

<400> SEQUENCE: 21
gaggagagat cttttgatct ccagtcgtgt         30

<210> SEQ ID NO 22
<211> LENGTH: 39
<212> TYPE: DNA
<213> ORGANISM: Artificial Sequence
<220> FEATURE:
<223> OTHER INFORMATION: Reverse primer D-R

<400> SEQUENCE: 22
gctagcggcc gacgcggcca agccctcggt gaggagagg                                   39

<210> SEQ ID NO 23
<211> LENGTH: 39
<212> TYPE: DNA
<213> ORGANISM: Artificial Sequence
<220> FEATURE:
<223> OTHER INFORMATION: forward primer 3M-Fc

<400> SEQUENCE: 23
aaaaaaggcc gtgggggccg atgttcgggc ctgctcctc                                   39

<210> SEQ ID NO 24
<211> LENGTH: 40
<212> TYPE: DNA
<213> ORGANISM: Artificial Sequence
<220> FEATURE:
<223> OTHER INFORMATION: forward primer 4M-Fc

<400> SEQUENCE: 24
aaaaaaggcc gtgggggcca aggacgggcc ctgtgtgatc                                  40

<210> SEQ ID NO 25
<211> LENGTH: 39
<212> TYPE: DNA
<213> ORGANISM: Artificial Sequence
<220> FEATURE:
<223> OTHER INFORMATION: forward primer 5M-Fc

<400> SEQUENCE: 25
aaaaaaggcc gtgggggccg tggccaacag ctgcacccc                                   39

<210> SEQ ID NO 26
<211> LENGTH: 39
<212> TYPE: DNA
<213> ORGANISM: Artificial Sequence
<220> FEATURE:
<223> OTHER INFORMATION: forward primer 6M-Fc

<400> SEQUENCE: 26
aaaaaaggcc gtgggggccc cggtgaccaa ctgcgccag                                   39

<210> SEQ ID NO 27
<211> LENGTH: 39
<212> TYPE: DNA
<213> ORGANISM: Artificial Sequence
<220> FEATURE:
<223> OTHER INFORMATION: forward primer JM-Fc

<400> SEQUENCE: 27
aaaaaaggcc gtgggggcca agaagcgcgc gctgagccc                                   39

<210> SEQ ID NO 28
<211> LENGTH: 906
<212> TYPE: DNA
<213> ORGANISM: Artificial Sequence
<220> FEATURE:
<223> OTHER INFORMATION: gene sequence of DLK1

<400> SEQUENCE: 28
atgaccgcga ccgaagccct cctgcgcgtc ctcttgctcc tgctggcttt cggccacagc            60
acctatgggg ctgaatgctt cccggcctgc aaccccaaa atggattctg cgaggatgac            120
aatgtttgca ggtgccagcc tggctggcag ggtcccctt tgtgaccagtg cgtgacctct           180 cccggctgcc ttcacggact ctgtggagaa cccgggcagt gcatttgcac cgacggctgg           240

```
gacggggagc tctgtgatag agatgttcgg gcctgctcct cggcccctg tgccaacaac    300 gggacctgcg tgagcctgga cgatggcctc tatgaatgct cctgtgcccc cgggtactcg    360
ggaaaggact gccagaaaaa ggacgggccc tgtgtgatca acggctcccc ctgccagcac    420
ggaggcacct gcgtggatga tgagggccgg gcctcccatg cctcctgcct gtgcccccct    480
ggcttctcag gcaatttctg cgagatcgtg gccaacagct gcaccccaa cccatgcgag    540 aacgacggcg tctgcactga cattgggggc gacttccgct gccggtgccc agccggcttc    600
atcgacaaga cctgcagccg cccggtgacc aactgcgcca gcagcccgtg ccagaacggg    660
ggcacctgcc tgcagcacac ccaggtgagc tacgagtgtc tgtgcaagcc cgagttcaca    720
ggtctcacct gtgtcaagaa gcgcgcgctg agccccagc aggtcacccg tctgcccagc    780
ggctatgggc tggcctaccg cctgacccct ggggtgcacg agctgccggt gcagcagccg    840
gagcaccgca tcctgaaggt gtccatgaaa gagctcaaca gaaaaccccc tctcctcacc    900
gagggc                                                               906
```

```
<210> SEQ ID NO 29
<211> LENGTH: 302
<212> TYPE: PRT
<213> ORGANISM: Artificial Sequence
<220> FEATURE:
<223> OTHER INFORMATION: amino acid sequence of DLK1

<400> SEQUENCE: 29

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
                20                  25                  30

Gln Asn Gly Phe Cys Glu Asp Asp Asn Val Cys Arg Cys Gln Pro Gly
            35                  40                  45

Trp Gln Gly Pro Leu Cys Asp Gln Cys Val Thr Ser Pro Gly Cys Leu
        50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95

Cys Ala Asn Asn Gly Thr Cys Val Ser Leu Asp Asp Gly Leu Tyr Glu
                100                 105                 110

Cys Ser Cys Ala Pro Gly Tyr Ser Gly Lys Asp Cys Gln Lys Lys Asp
            115                 120                 125

Gly Pro Cys Val Ile Asn Gly Ser Pro Cys Gln His Gly Gly Thr Cys
        130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240
```

```
Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly
    290                 295                 300

<210> SEQ ID NO 30
<211> LENGTH: 215
<212> TYPE: PRT
<213> ORGANISM: Artificial Sequence
<220> FEATURE:
<223> OTHER INFORMATION: amino acid sequence of EGF3-6

<400> SEQUENCE: 30

Asp Val Arg Ala Cys Ser Ser Ala Pro Cys Ala Asn Asn Gly Thr Cys
1               5                   10                  15

Val Ser Leu Asp Asp Gly Leu Tyr Glu Cys Ser Cys Ala Pro Gly Tyr
            20                  25                  30

Ser Gly Lys Asp Cys Gln Lys Lys Asp Gly Pro Cys Val Ile Asn Gly
        35                  40                  45

Ser Pro Cys Gln His Gly Gly Thr Cys Val Asp Asp Glu Gly Arg Ala
    50                  55                  60

Ser His Ala Ser Cys Leu Cys Pro Pro Gly Phe Ser Gly Asn Phe Cys
65                  70                  75                  80

Glu Ile Val Ala Asn Ser Cys Thr Pro Asn Pro Cys Glu Asn Asp Gly
                85                  90                  95

Val Cys Thr Asp Ile Gly Gly Asp Phe Arg Cys Arg Cys Pro Ala Gly
            100                 105                 110

Phe Ile Asp Lys Thr Cys Ser Arg Pro Val Thr Asn Cys Ala Ser Ser
        115                 120                 125

Pro Cys Gln Asn Gly Gly Thr Cys Leu Gln His Thr Gln Val Ser Tyr
    130                 135                 140

Glu Cys Leu Cys Lys Pro Glu Phe Thr Gly Leu Thr Cys Val Lys Lys
145                 150                 155                 160

Arg Ala Leu Ser Pro Gln Gln Val Thr Arg Leu Pro Ser Gly Tyr Gly
                165                 170                 175

Leu Ala Tyr Arg Leu Thr Pro Gly Val His Glu Leu Pro Val Gln Gln
            180                 185                 190

Pro Glu His Arg Ile Leu Lys Val Ser Met Lys Glu Leu Asn Lys Lys
        195                 200                 205

Thr Pro Leu Leu Thr Glu Gly
    210                 215

<210> SEQ ID NO 31
<211> LENGTH: 176
<212> TYPE: PRT
<213> ORGANISM: Artificial Sequence
<220> FEATURE:
<223> OTHER INFORMATION: amino acid sequence of EGF4-6

<400> SEQUENCE: 31

Lys Asp Gly Pro Cys Val Ile Asn Gly Ser Pro Cys Gln His Gly Gly
1               5                   10                  15

Thr Cys Val Asp Asp Glu Gly Arg Ala Ser His Ala Ser Cys Leu Cys
```

```
                  20                  25                  30
Pro Pro Gly Phe Ser Gly Asn Phe Cys Glu Ile Val Ala Asn Ser Cys
            35                  40                  45

Thr Pro Asn Pro Cys Glu Asn Asp Gly Val Cys Thr Asp Ile Gly Gly
        50                  55                  60

Asp Phe Arg Cys Arg Cys Pro Ala Gly Phe Ile Asp Lys Thr Cys Ser
65                  70                  75                  80

Arg Pro Val Thr Asn Cys Ala Ser Ser Pro Cys Gln Asn Gly Gly Thr
                85                  90                  95

Cys Leu Gln His Thr Gln Val Ser Tyr Glu Cys Leu Cys Lys Pro Glu
            100                 105                 110

Phe Thr Gly Leu Thr Cys Val Lys Lys Arg Ala Leu Ser Pro Gln Gln
        115                 120                 125

Val Thr Arg Leu Pro Ser Gly Tyr Gly Leu Ala Tyr Arg Leu Thr Pro
    130                 135                 140

Gly Val His Glu Leu Pro Val Gln Gln Pro Glu His Arg Ile Leu Lys
145                 150                 155                 160

Val Ser Met Lys Glu Leu Asn Lys Lys Thr Pro Leu Leu Thr Glu Gly
                165                 170                 175

<210> SEQ ID NO 32
<211> LENGTH: 133
<212> TYPE: PRT
<213> ORGANISM: Artificial Sequence
<220> FEATURE:
<223> OTHER INFORMATION: amino acid sequence of EGF5-6

<400> SEQUENCE: 32

Val Ala Asn Ser Cys Thr Pro Asn Pro Cys Glu Asn Asp Gly Val Cys
1               5                   10                  15

Thr Asp Ile Gly Gly Asp Phe Arg Cys Arg Cys Pro Ala Gly Phe Ile
            20                  25                  30

Asp Lys Thr Cys Ser Arg Pro Val Thr Asn Cys Ala Ser Ser Pro Cys
        35                  40                  45

Gln Asn Gly Gly Thr Cys Leu Gln His Thr Gln Val Ser Tyr Glu Cys
    50                  55                  60

Leu Cys Lys Pro Glu Phe Thr Gly Leu Thr Cys Val Lys Lys Arg Ala
65                  70                  75                  80

Leu Ser Pro Gln Gln Val Thr Arg Leu Pro Ser Gly Tyr Gly Leu Ala
                85                  90                  95

Tyr Arg Leu Thr Pro Gly Val His Glu Leu Pro Val Gln Gln Pro Glu
            100                 105                 110

His Arg Ile Leu Lys Val Ser Met Lys Glu Leu Asn Lys Lys Thr Pro
        115                 120                 125

Leu Leu Thr Glu Gly
    130

<210> SEQ ID NO 33
<211> LENGTH: 95
<212> TYPE: PRT
<213> ORGANISM: Artificial Sequence
<220> FEATURE:
<223> OTHER INFORMATION: amino acid sequence of EGF6

<400> SEQUENCE: 33

Pro Val Thr Asn Cys Ala Ser Ser Pro Cys Gln Asn Gly Gly Thr Cys
1               5                   10                  15
```

```
Leu Gln His Thr Gln Val Ser Tyr Glu Cys Leu Cys Lys Pro Glu Phe
                20                  25                  30

Thr Gly Leu Thr Cys Val Lys Lys Arg Ala Leu Ser Pro Gln Gln Val
         35                  40                  45

Thr Arg Leu Pro Ser Gly Tyr Gly Leu Ala Tyr Arg Leu Thr Pro Gly
     50                  55                  60

Val His Glu Leu Pro Val Gln Gln Pro Glu His Arg Ile Leu Lys Val
 65                  70                  75                  80

Ser Met Lys Glu Leu Asn Lys Lys Thr Pro Leu Leu Thr Glu Gly
                 85                  90                  95

<210> SEQ ID NO 34
<211> LENGTH: 57
<212> TYPE: PRT
<213> ORGANISM: Artificial Sequence
<220> FEATURE:
<223> OTHER INFORMATION: amino acid sequence of Juxtamembrane region
      (JM)

<400> SEQUENCE: 34

Lys Lys Arg Ala Leu Ser Pro Gln Gln Val Thr Arg Leu Pro Ser Gly
1               5                   10                  15

Tyr Gly Leu Ala Tyr Arg Leu Thr Pro Gly Val His Glu Leu Pro Val
             20                  25                  30

Gln Gln Pro Glu His Arg Ile Leu Lys Val Ser Met Lys Glu Leu Asn
         35                  40                  45

Lys Lys Thr Pro Leu Leu Thr Glu Gly
     50                  55

<210> SEQ ID NO 35
<211> LENGTH: 121
<212> TYPE: PRT
<213> ORGANISM: Artificial Sequence
<220> FEATURE:
<223> OTHER INFORMATION: DLK1 A04 HC

<400> SEQUENCE: 35

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Lys Asp Tyr
             20                  25                  30

Ala Ile His Trp Val Arg Gln Ala Pro Gly Gln Arg Leu Glu Trp Met
         35                  40                  45

Gly Trp Ile Asn Pro Gly Ser Gly Asn Thr Lys Tyr Ser His Asn Phe
     50                  55                  60

Glu Gly Arg Val Ile Leu Thr Arg Asp Ala Ser Ala Asn Thr Ala Tyr
 65                  70                  75                  80

Leu Glu Leu Pro Ser Leu Arg Ser Glu Asp Thr Ala Val Tyr Tyr Cys
                 85                  90                  95

Ala Arg Ser Val Ser Ala Tyr Gly Ser Asn Tyr Phe Asp Pro Trp Gly
            100                 105                 110

Gln Gly Thr Leu Ile Thr Val Ser Ser
        115                 120

<210> SEQ ID NO 36
<211> LENGTH: 123
<212> TYPE: PRT
<213> ORGANISM: Artificial Sequence
<220> FEATURE:
<223> OTHER INFORMATION: DLK1 A05 HC
```

<400> SEQUENCE: 36

Gln Met Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu His
            20                  25                  30

Ala Met His Trp Val Arg Gln Ala Pro Gly Lys Gly Leu Glu Trp Val
        35                  40                  45

Ser Gly Ile Asn Trp Asn Ser Gly Lys Thr Gly Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Gly Tyr Gly Gly Asn Thr Asn Trp Tyr Phe Asp Leu
            100                 105                 110

Trp Gly Arg Gly Thr Leu Val Thr Val Ser Ser
        115                 120

<210> SEQ ID NO 37
<211> LENGTH: 122
<212> TYPE: PRT
<213> ORGANISM: Artificial Sequence
<220> FEATURE:
<223> OTHER INFORMATION: DLK1 A10 HC

<400> SEQUENCE: 37

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Leu Ala Thr Gly Lys Gly Tyr Ala Asp Tyr Trp
            100                 105                 110

Gly Gln Gly Thr Leu Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: DLK1 B09 HC

<400> SEQUENCE: 38

Gln Met Gln Leu Val Glu Ser Gly Gly Arg Leu Val Arg Pro Gly Gly
1               5                   10                  15

Ser Leu Arg Leu Ser Cys Ala Ala Ser Gly Phe Pro Phe Thr Ser Tyr
            20                  25                  30

Ala Met Asn Trp Val Arg Gln Thr Pro Gly Lys Gly Leu Glu Trp Val
        35                  40                  45

Ser Thr Ile Thr Ala Thr Ser Gly Lys Thr Tyr Tyr Ala Asp Ser Val
        50                  55                  60

Lys Gly Arg Phe Thr Ile Ser Arg Asp Asn Arg Asn Thr Leu Phe
 65                  70                  75                  80

Leu Gln Met Asn Ser Leu Arg Ala Glu Asp Thr Ala Val Tyr Tyr Cys
                85                  90                  95

Val Arg Gly Glu Ser Cys Ser Gly Gly Ala Cys Ser Asp Phe Asp Tyr
                100                 105                 110

Trp Gly Gln Gly Ala Leu Val Thr Val Ser Ser
            115                 120

<210> SEQ ID NO 39
<211> LENGTH: 117
<212> TYPE: PRT
<213> ORGANISM: Artificial Sequence
<220> FEATURE:
<223> OTHER INFORMATION: DLK1 H06 HC

<400> SEQUENCE: 39

Gln Val Gln Leu Val Gln Ser Gly Gly Gly Leu Ile Gln Pro Gly Gly
 1               5                  10                  15

Ser Leu Arg Leu Ser Cys Ala Ala Ser Gly Phe Thr Phe Ser Leu Tyr
                20                  25                  30

Gly Met Ser Trp Val Arg Gln Ala Pro Gly Lys Gly Leu Glu Trp Val
            35                  40                  45

Ser Ser Ile Pro Gly Ser Gly Thr Arg Thr His Tyr Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                85                  90                  95

Ala Lys Ser Thr Ala Tyr Leu Phe Asp Tyr Trp Gly Pro Gly Thr Leu
                100                 105                 110

Val Thr Val Ser Ser
        115

<210> SEQ ID NO 40
<211> LENGTH: 125
<212> TYPE: PRT
<213> ORGANISM: Artificial Sequence
<220> FEATURE:
<223> OTHER INFORMATION: DLK1 H12 HC

<400> SEQUENCE: 40

Gln Val Gln Leu Val Gln Ser Gly Gly Gly Leu Val Lys Pro Gly Gly
 1               5                  10                  15

Ser Leu Arg Leu Ser Cys Ala Ala Ser Glu Phe Thr Phe Ser Asp Tyr
                20                  25                  30

Tyr Met Ser Trp Val Arg Gln Ala Pro Gly Lys Gly Leu Glu Trp Leu
            35                  40                  45

Ser Tyr Ile Ser Gly Ser Gly Ile Thr Thr Tyr Ala Asp Ser Val
        50                  55                  60

Lys Gly Arg Phe Thr Ile Ser Arg Asp Asn Gly Lys Lys Ser Leu Tyr
 65                  70                  75                  80

Leu Glu Met Asn Ser Leu Arg Ala Glu Asp Thr Ala Val Tyr Tyr Cys
                85                  90                  95

Ala Arg Leu Gln Gly His Cys Ser Gly Gly Ala Cys Ser Asn Trp Phe

```
            100                 105                 110
Asp Ala Trp Gly Gln Gly Thr Leu Ile Thr Val Ser Ser
        115                 120                 125

<210> SEQ ID NO 41
<211> LENGTH: 110
<212> TYPE: PRT
<213> ORGANISM: Artificial Sequence
<220> FEATURE:
<223> OTHER INFORMATION: DLK1 A04 LC

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ser Thr Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Asp Ile Lys Arg Gly Gly
            100                 105                 110

<210> SEQ ID NO 42
<211> LENGTH: 113
<212> TYPE: PRT
<213> ORGANISM: Artificial Sequence
<220> FEATURE:
<223> OTHER INFORMATION: DLK1 A05 LC

<400> SEQUENCE: 42

Gln Phe Val Leu Thr Gln Pro Pro Ser Val Ser Gly Ala Pro Gly Gln
1               5                   10                  15

Asn Val Thr Ile Ser Cys Ile Gly Thr Ser Ser Asn Ile Gly Val Gly
            20                  25                  30

Tyr Asp Val His Trp Tyr Gln Gln Val Pro Gly Thr Ala Pro Lys Leu
        35                  40                  45

Leu Val Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Gly Val Val Phe Gly Gly Gly Thr Lys Leu Thr Val Leu Gly Gly
            100                 105                 110

Gly

<210> SEQ ID NO 43
<211> LENGTH: 110
<212> TYPE: PRT
<213> ORGANISM: Artificial Sequence
<220> FEATURE:
<223> OTHER INFORMATION: DLK1 A10 LC

<400> SEQUENCE: 43
```

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Arg Ile Ser Ser Trp
            20                  25                  30

Leu Ala Trp Tyr Gln Gln Lys Pro Gly Arg Ala Pro Lys Leu Leu Ile
        35                  40                  45

His Ser Ala Ser Thr Leu His Asn Gly Val Pro Ser Arg Phe Ser Gly
    50                  55                  60

Ser Ala Ser Gly Thr Asp Phe Thr Leu Thr Ile Ser Ser Leu Gln Pro
65                  70                  75                  80

Glu Asp Tyr Ala Ile Tyr Tyr Cys Gln Gln Gly His Ser Phe Pro Tyr
                85                  90                  95

Thr Phe Gly Gln Gly Thr Lys Leu Glu Ile Lys Arg Gly Gly
                100                 105                 110
```

<210> SEQ ID NO 44
<211> LENGTH: 113
<212> TYPE: PRT
<213> ORGANISM: Artificial Sequence
<220> FEATURE:
<223> OTHER INFORMATION: DLK1 B09 LC

<400> SEQUENCE: 44

```
Gln Leu Val Leu Thr Gln Pro Ala Ser Val Ser Gly Ser Pro Gly Gln
1               5                   10                  15

Ser Val Thr Ile Ser Cys Thr Gly Thr Ser Ser Asp Ile Gly Arg Tyr
            20                  25                  30

Asn Arg Val Ser Trp Tyr Gln His Pro Gly Lys Ala Pro Lys Leu
        35                  40                  45

Ile Leu Asn Asp Val Thr Thr Arg Pro Ser Gly Phe Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Ser Cys Gly Ser Tyr Ala Gly Ser
                85                  90                  95

Tyr Thr Tyr Val Phe Gly Thr Gly Thr Lys Val Thr Val Leu Gly Gly
                100                 105                 110

Gly
```

<210> SEQ ID NO 45
<211> LENGTH: 110
<212> TYPE: PRT
<213> ORGANISM: Artificial Sequence
<220> FEATURE:
<223> OTHER INFORMATION: DLK1 H06 LC

<400> SEQUENCE: 45

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Ile Arg His Tyr
            20                  25                  30

Leu Ala Trp Tyr Gln Gln Lys Pro Gly Gln Ala Pro Arg Leu Leu Ile
        35                  40                  45

His Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80
```

```
Glu Asp Phe Ala Val Tyr Tyr Cys Gln His Tyr Gly Ser Pro Leu His
                85                  90                  95

Ser Phe Gly Pro Gly Thr Lys Val Glu Ile Lys Arg Gly Gly
            100                 105                 110

<210> SEQ ID NO 46
<211> LENGTH: 110
<212> TYPE: PRT
<213> ORGANISM: Artificial Sequence
<220> FEATURE:
<223> OTHER INFORMATION: DLK1 H12 LC

<400> SEQUENCE: 46

Asp Ile Gln Met Thr Gln Ser Pro Ser Ser Leu Ser Ala Ser Val Gly
1               5                   10                  15

Asp Arg Leu Thr Ile Thr Cys Arg Ala Ser Gln Ser Ile Leu Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Gly Tyr Gly Thr Pro Tyr
                85                  90                  95

Thr Phe Gly Gln Gly Thr Lys Val Asp Ile Lys Arg Gly Gly
            100                 105                 110

<210> SEQ ID NO 47
<211> LENGTH: 117
<212> TYPE: PRT
<213> ORGANISM: Artificial Sequence
<220> FEATURE:
<223> OTHER INFORMATION: ACVR2B A06 HC

<400> SEQUENCE: 47

Val Gln Leu Val Gln Ser Gly Gly Gly Leu Val Gln Pro Gly Arg Ser
1               5                   10                  15

Leu Arg Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
        35                  40                  45

Phe Ile Arg Ser Lys Arg Tyr Asp Gly Thr Ala Glu Tyr Ala Ala Ser
50                  55                  60

Val Lys Gly Arg Phe Thr Ile Ser Arg Asp Asp Ser Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly His Tyr Ala Met Asp Val Trp Gly Gln Gly Thr Thr
            100                 105                 110

Val Thr Val Ser Ser
        115

<210> SEQ ID NO 48
<211> LENGTH: 118
<212> TYPE: PRT
<213> ORGANISM: Artificial Sequence
<220> FEATURE:
<223> OTHER INFORMATION: ACVR2B A07 HC
```

```
<400> SEQUENCE: 48

Gln Leu Val Glu Ser Gly Gly Leu Val Arg Pro Gly Arg Ser Leu
1               5                   10                  15

Thr Leu Ser Cys Thr Ala Ser Gly Phe Thr Phe Asn Asp Tyr Ala Met
            20                  25                  30

His Trp Val Arg Gln Ala Pro Gly Lys Gly Leu Glu Trp Val Ser Gly
        35                  40                  45

Ile Ser Trp Asn Thr Asn Ser Lys Ala Tyr Ala Asp Ser Val Lys Gly
50                  55                  60

Arg Phe Ile Ile Ser Arg Asp Asn Ala Lys Asn Ser Leu Tyr Leu Glu
65                  70                  75                  80

Met Asn Ser Leu Arg Ala Glu Asp Thr Ala Val Tyr Tyr Cys Val Arg
                85                  90                  95

Asp Gly Gly Arg Phe Tyr Tyr Gly Leu Asp Val Trp Gly Gln Gly Thr
            100                 105                 110

Ser Val Thr Val Ser Ser
        115

<210> SEQ ID NO 49
<211> LENGTH: 114
<212> TYPE: PRT
<213> ORGANISM: Artificial Sequence
<220> FEATURE:
<223> OTHER INFORMATION: ACVR2B A09 HC

<400> SEQUENCE: 49

Val Gln Leu Val Glu Ser Gly Gly Gly Leu Val Gln Pro Gly Arg Ser
1               5                   10                  15

Leu Arg Leu Ser Cys Ala Ala Ser Gly Phe Thr Phe Asp Ser Tyr Trp
            20                  25                  30

Met Ser Trp Val Arg Gln Ala Pro Gly Lys Gly Leu Glu Trp Val Ala
        35                  40                  45

Asn Ile Lys Tyr Asp Gly Ser Glu Lys His Tyr Met Asp Ser Val Lys
50                  55                  60

Gly Arg Phe Thr Ile Ser Arg Asp Asn Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Lys Gly Ala Trp Leu Asp Tyr Trp Gly Gln Gly Thr Gln Val Thr Val
            100                 105                 110

Ser Ser

<210> SEQ ID NO 50
<211> LENGTH: 119
<212> TYPE: PRT
<213> ORGANISM: Artificial Sequence
<220> FEATURE:
<223> OTHER INFORMATION: ACVR2B B11 HC

<400> SEQUENCE: 50

Val Gln Leu Val Glu Ser Gly Gly Gly Leu Val Gln Pro Gly Arg Ser
1               5                   10                  15

Leu Arg Leu Ser Cys Ala Ala Ser Gly Phe Thr Phe Asp Asn His Ala
            20                  25                  30

Met His Trp Val Arg Arg Ala Pro Gly Lys Gly Leu Glu Trp Val Ser
        35                  40                  45

Gly Ile Ser Trp Asn Gly Gly Thr Thr Ala Tyr Ala Asp Ser Val Lys
```

```
                    50                  55                  60
Gly Arg Phe Ser Ile Phe Arg Asp Asn Ala Glu Lys Ser Leu Tyr Leu
 65                  70                  75                  80

Gln Met Asn Ser Leu Arg Ala Glu Asp Thr Ala Val Tyr Tyr Cys Ala
                 85                  90                  95

Arg Gly Ser Ser Ser Gly Arg Tyr Tyr Phe Asp Tyr Trp Gly Gln Gly
                100                 105                 110

Thr Leu Val Thr Val Ser Ser
            115

<210> SEQ ID NO 51
<211> LENGTH: 114
<212> TYPE: PRT
<213> ORGANISM: Artificial Sequence
<220> FEATURE:
<223> OTHER INFORMATION: ACVR2B B12 HC

<400> SEQUENCE: 51

Val Gln Leu Val Gln Ser Gly Ala Glu Val Lys Lys Pro Gly Glu Ser
 1               5                  10                  15

Leu Lys Ile Ser Cys Lys Thr Ser Gly Tyr Thr Phe Thr His Tyr Trp
                20                  25                  30

Ile Gly Trp Val Arg Gln Met Pro Gly Lys Gly Leu Glu Trp Met Gly
            35                  40                  45

Arg Ile Asn Pro Thr Asp Ser Tyr Ala Asp Tyr Ser Pro Ser Phe Gln
 50                  55                  60

Gly His Val Ile Met Ser Val Asp Lys Ser Val Ser Thr Ala Tyr Leu
 65                  70                  75                  80

His Trp Asn Ser Leu Lys Ala Ser Asp Thr Ala Met Tyr Tyr Cys Ala
                 85                  90                  95

Arg Gly Thr Ala Leu Gly Val Trp Gly Gln Gly Thr Thr Val Thr Val
                100                 105                 110

Ser Ser

<210> SEQ ID NO 52
<211> LENGTH: 117
<212> TYPE: PRT
<213> ORGANISM: Artificial Sequence
<220> FEATURE:
<223> OTHER INFORMATION: ACVR2B B08 HC

<400> SEQUENCE: 52

Val Gln Leu Val Gln Ser Gly Gly Gly Leu Val His Pro Gly Gln Ser
 1               5                  10                  15

Leu Arg Leu Ser Cys Thr Gly Ser Gly Phe Pro Phe Gly Asp Tyr Ser
                20                  25                  30

Met Thr Trp Val Arg Gln Ala Pro Gly Lys Gly Leu Glu Trp Val Gly
            35                  40                  45

Leu Val Arg Ser Lys Ala Tyr Gly Gly Thr Thr Glu Tyr Ala Ala Ser
 50                  55                  60

Val Lys Gly Arg Phe Ile Met Ser Arg Asp Asp Ser Arg Ser Ile Ala
 65                  70                  75                  80

Tyr Leu Gln Met Asn Ser Leu Arg Ala Glu Asp Thr Ala Val Tyr Tyr
                 85                  90                  95

Cys Ala Arg Gly His Tyr Gly Met Asp Val Trp Gly Gln Gly Thr Thr
                100                 105                 110

Val Thr Val Ser Ser
```

<210> SEQ ID NO 53
<211> LENGTH: 116
<212> TYPE: PRT
<213> ORGANISM: Artificial Sequence
<220> FEATURE:
<223> OTHER INFORMATION: ACVR2B C07 HC

<400> SEQUENCE: 53

```
Gln Met Gln Leu Val Gln Ser Gly Gly Gly Leu Val Lys Pro Gly Gly
1               5                   10                  15

Ser Leu Arg Leu Ser Cys Ala Pro Ser Gly Phe Thr Phe Arg Asp Tyr
            20                  25                  30

His Met Ser Trp Ile Arg Gln Ala Pro Gly Lys Gly Leu Glu Trp Ile
        35                  40                  45

Ser Asn Ile Ser Asn Ser Gly Thr Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Gly Met Asp Ile Trp Gly Gln Gly Thr Thr Ile
            100                 105                 110

Thr Val Ser Ser
        115
```

<210> SEQ ID NO 54
<211> LENGTH: 119
<212> TYPE: PRT
<213> ORGANISM: Artificial Sequence
<220> FEATURE:
<223> OTHER INFORMATION: ACVR2B C08 HC

<400> SEQUENCE: 54

```
Val Gln Leu Val Glu Ser Gly Gly Gly Leu Val Gln Pro Gly Gly Ser
1               5                   10                  15

Leu Arg Leu Ser Cys Ser Ala Ser Gly Phe Thr Phe Ser Ser Tyr Ala
            20                  25                  30

Met His Trp Val Arg Gln Ala Pro Gly Lys Gly Leu Glu Tyr Val Ser
        35                  40                  45

Ala Ile Ser Ser Asn Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Tyr Gly Gly Tyr Gly Asn Ala Phe Asp Ile Trp Gly Gln Gly
            100                 105                 110

Thr Met Ile Thr Val Ser Ser
        115
```

<210> SEQ ID NO 55
<211> LENGTH: 117
<212> TYPE: PRT
<213> ORGANISM: Artificial Sequence
<220> FEATURE:
<223> OTHER INFORMATION: ACVR2B D11 HC

<400> SEQUENCE: 55

Met Gln Leu Val Gln Ser Gly Gly Leu Val Gln Pro Gly Arg Ser
1               5                   10                  15

Leu Gly Leu Ser Cys Thr Ala Ser Gly Phe Thr Phe Gly Asp Tyr Ala
            20                  25                  30

Met Ser Trp Val Arg Gln Ala Pro Gly Lys Gly Leu Glu Trp Val Gly
        35                  40                  45

Phe Ile Arg Ser Lys Ala Tyr Gly Gly Thr Thr Glu Tyr Ala Ala Ser
    50                  55                  60

Val Lys Gly Arg Leu Thr Ile Ser Arg Asp Asp Ser Lys Ser Ile Ala
65                  70                  75                  80

Tyr Leu Gln Met Asn Ser Leu Arg Ala Glu Thr Ala Val Tyr Tyr
                85                  90                  95

Cys Ala Arg Gly His Tyr Gly Met Asp Val Trp Gly Gln Gly Thr Thr
                100                 105                 110

Val Thr Val Ser Ser
            115

<210> SEQ ID NO 56
<211> LENGTH: 121
<212> TYPE: PRT
<213> ORGANISM: Artificial Sequence
<220> FEATURE:
<223> OTHER INFORMATION: ACVR2B D07 HC

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Asp Gln Ser Arg Gly Trp Tyr Ser Asn Phe Asp Ser Trp Gly
                100                 105                 110

Gln Gly Thr Leu Val Thr Val Ser Ser
            115                 120

<210> SEQ ID NO 57
<211> LENGTH: 116
<212> TYPE: PRT
<213> ORGANISM: Artificial Sequence
<220> FEATURE:
<223> OTHER INFORMATION: ACVR2B F08 HC

<400> SEQUENCE: 57

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Asp His Tyr
            20                  25                  30

Met Asp Trp Val Arg Gln Ala Pro Gly Lys Gly Leu Glu Trp Val Gly
        35                  40                  45

Arg Thr Arg Asn Lys Ala Asn Ser Tyr Thr Thr Glu Tyr Ala Ala Ser

```
            50                   55                   60
Val Lys Gly Arg Phe Thr Ile Ser Arg Asp Asp Ser Lys Asn Ser Leu
 65                  70                  75                  80

Tyr Leu Gln Met Asn Ser Leu Arg Ala Glu Asp Thr Ala Val Tyr Tyr
                 85                  90                  95

Cys Thr Lys Gly Ala Trp Leu Asp Tyr Trp Gly Gln Gly Thr Leu Val
                100                 105                 110

Thr Val Ser Ser
            115

<210> SEQ ID NO 58
<211> LENGTH: 107
<212> TYPE: PRT
<213> ORGANISM: Artificial Sequence
<220> FEATURE:
<223> OTHER INFORMATION: ACVR2B A06 LC

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Ser Ile Ser Asn Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Thr Pro Phe
                 85                  90                  95

Thr Phe Gly Leu Gly Asn Gln Leu Glu Ile Lys
                100                 105

<210> SEQ ID NO 59
<211> LENGTH: 112
<212> TYPE: PRT
<213> ORGANISM: Artificial Sequence
<220> FEATURE:
<223> OTHER INFORMATION: ACVR2B A07 LC

<400> SEQUENCE: 59

Asp Ile Val Met Thr Gln Thr Pro Val Ser Pro Val Thr Leu Gly
 1               5                  10                  15

Gln Pro Ala Ser Ile Ser Cys Arg Ser Ser Gln Ser Leu Ile His Ser
             20                  25                  30

Asp Gly Asn Thr Tyr Leu Ser Trp Ile Gln Gln Arg Pro Gly Gln Pro
         35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Ala Glu Thr
                 85                  90                  95

Ser Gln Val Pro His Thr Phe Gly Gln Gly Thr Lys Val Glu Ile Lys
                100                 105                 110

<210> SEQ ID NO 60
<211> LENGTH: 106
```

<212> TYPE: PRT
<213> ORGANISM: Artificial Sequence
<220> FEATURE:
<223> OTHER INFORMATION: ACVR2B A09 LC

<400> SEQUENCE: 60

Ile Gln Met Thr Gln Ser Pro Ser Ala Met Ser Ala Ser Val Gly Asp
1               5                   10                  15

Arg Val Thr Ile Thr Cys Arg Ala Ser Gln Gly Ile Ser Asn Tyr Leu
            20                  25                  30

Ala Trp Phe Gln Gln Lys Pro Gly Lys Val Pro Lys Arg Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Gly Phe Thr Leu Thr Ile Thr Ser Leu Gln Pro Glu
65                  70                  75                  80

Asp Phe Ala Thr Tyr Tyr Cys Leu Gln His Lys Ser Tyr Pro Tyr Thr
                85                  90                  95

Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: ACVR2B B11 LC

<400> SEQUENCE: 61

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Tyr
            20                  25                  30

Leu Asn Trp Tyr Gln His Gln Ser Gly Lys Ala Pro Lys Leu Leu Ile
        35                  40                  45

Tyr Gly Ala Phe Arg Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Lys Asn Phe Pro Leu
                85                  90                  95

Thr Phe Gly Gly Gly Thr Lys Val Asp Ile Lys
            100                 105

<210> SEQ ID NO 62
<211> LENGTH: 106
<212> TYPE: PRT
<213> ORGANISM: Artificial Sequence
<220> FEATURE:
<223> OTHER INFORMATION: ACVR2B B12 LC

<400> SEQUENCE: 62

Ile Gln Met Thr Gln Ser Pro Ser Ala Met Ser Ala Ser Val Gly Asp
1               5                   10                  15

Arg Val Thr Ile Thr Cys Arg Ala Ser Gln Gly Ile Ser Asn Tyr Leu
            20                  25                  30

Ala Trp Phe Gln Gln Lys Pro Gly Lys Val Pro Lys Arg Leu Ile Tyr
        35                  40                  45

Ala Ala Ser Ser Leu Gln Ser Gly Val Pro Ser Arg Phe Ser Gly Ser

```
                    50                  55                  60
Gly Ser Gly Thr Glu Phe Thr Leu Thr Ile Thr Ser Leu Gln Pro Glu
 65                  70                  75                  80

Asp Phe Ala Thr Tyr Tyr Cys Leu Gln His Lys Ser Tyr Pro Tyr Thr
                 85                  90                  95

Phe Gly Gln Gly Thr Lys Leu Glu Ile Lys
                100                 105

<210> SEQ ID NO 63
<211> LENGTH: 107
<212> TYPE: PRT
<213> ORGANISM: Artificial Sequence
<220> FEATURE:
<223> OTHER INFORMATION: ACVR2B B08 LC

<400> SEQUENCE: 63

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Asn Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ser Tyr Pro Tyr
                 85                  90                  95

Thr Phe Gly Gln Gly Thr Lys Val Glu Ile Lys
                100                 105

<210> SEQ ID NO 64
<211> LENGTH: 107
<212> TYPE: PRT
<213> ORGANISM: Artificial Sequence
<220> FEATURE:
<223> OTHER INFORMATION: ACVR2B C07 LC

<400> SEQUENCE: 64

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ala Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Lys Ser Tyr Pro Leu
                 85                  90                  95

Ser Phe Gly Gly Gly Thr Lys Val Glu Ile Lys
                100                 105

<210> SEQ ID NO 65
<211> LENGTH: 107
<212> TYPE: PRT
<213> ORGANISM: Artificial Sequence
<220> FEATURE:
```

<223> OTHER INFORMATION: ACVR2B C08 LC

<400> SEQUENCE: 65

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Phe Cys Gln Gln Gly Lys Ser Phe Pro Tyr
                85                  90                  95

Thr Phe Gly Pro Gly Thr Lys Val Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: ACVR2B D11 LC

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Asn Phe
            20                  25                  30

Leu Asn Trp Tyr Gln Gln Lys Pro Gly Lys Ala Pro Lys Leu Leu Ile
        35                  40                  45

Tyr Ser Ala Ser Arg Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: ACVR2B D07 LC

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Val Ser Asn Trp
            20                  25                  30

Leu Ala Trp Tyr Gln Leu Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Thr Gly Ser Glu Thr Glu Phe Thr Leu Thr Ile Ser Ser Leu Gln Pro

```
                65                  70                  75                  80

Asp Asp Phe Ala Thr Tyr Tyr Cys Gln Gln Tyr His Ser Tyr Pro Ile
                85                  90                  95

Thr Phe Gly Gln Gly Thr Arg Leu Glu Ile Lys
            100                 105

<210> SEQ ID NO 68
<211> LENGTH: 106
<212> TYPE: PRT
<213> ORGANISM: Artificial Sequence
<220> FEATURE:
<223> OTHER INFORMATION: ACVR2B F08 LC

<400> SEQUENCE: 68

Ile Gln Met Thr Gln Ser Pro Ser Ala Met Ser Ala Ser Val Gly Asp
1               5                   10                  15

Arg Val Thr Ile Thr Cys Arg Ala Ser Gln Gly Ile Ser Asn Tyr Leu
                20                  25                  30

Ala Trp Phe Gln Gln Lys Pro Gly Lys Val Pro Lys Arg Leu Ile Tyr
            35                  40                  45

Gly Ala Ser Ser Leu Gln Gly Gly Val Pro Ser Arg Phe Ser Gly Ser
        50                  55                  60

Gly Ser Gly Thr Glu Phe Thr Leu Thr Ile Thr Ser Leu Gln Pro Glu
65                  70                  75                  80

Asp Phe Ala Thr Tyr Phe Cys Leu Gln His Lys Ser Tyr Pro Leu Thr
                85                  90                  95

Phe Gly Pro Gly Thr Lys Val Glu Ile Lys
            100                 105
```